US006916472B2

(12) United States Patent
La Du et al.

(10) Patent No.: US 6,916,472 B2
(45) Date of Patent: Jul. 12, 2005

(54) PON3 AND USES THEREOF

(75) Inventors: Bert N. La Du, Ann Arbor, MI (US); Dragomir I. Draganov, Ann Arbor, MI (US); Phillip L. Stetson, Ann Arbor, MI (US); Catherine E. Watson, Ann Arbor, MI (US)

(73) Assignee: Regents of the University of Michigan, Ann Arbor, MI (US)

( * ) Notice: Subject to any disclaimer, the term of this patent is extended or adjusted under 35 U.S.C. 154(b) by 157 days.

(21) Appl. No.: 10/184,194

(22) Filed: Jun. 27, 2002

(65) Prior Publication Data

US 2003/0144228 A1 Jul. 31, 2003

Related U.S. Application Data

(62) Division of application No. 09/574,377, filed on May 19, 2000, now Pat. No. 6,573,370.

(51) Int. Cl.⁷ .......................... A61K 38/46; C12N 9/14
(52) U.S. Cl. ...................................... 424/94.6; 435/195
(58) Field of Search ......................... 424/94.6; 435/195

(56) References Cited

U.S. PATENT DOCUMENTS

| 4,657,760 | A | 4/1987 | Kung et al. .................... 424/85 |
| 4,683,195 | A | 7/1987 | Mullis et al. ................... 435/6 |
| 4,683,202 | A | 7/1987 | Mullis ......................... 435/91 |
| 4,946,778 | A | 8/1990 | Ladner et al. ............. 435/69.6 |
| 4,965,188 | A | 10/1990 | Mullis et al. ................... 435/6 |
| 5,096,815 | A | 3/1992 | Ladner et al. ............. 435/69.1 |
| 5,198,346 | A | 3/1993 | Ladner et al. ............. 435/69.1 |
| 5,206,344 | A | 4/1993 | Katre et al. .................. 530/351 |
| 5,223,409 | A | 6/1993 | Ladner et al. ............. 435/69.7 |
| 5,225,212 | A | 7/1993 | Martin et al. ............... 424/450 |
| 5,629,193 | A | 5/1997 | Hudson et al. ............. 435/325 |
| 5,792,639 | A | 8/1998 | Hudson et al. ............. 435/196 |

FOREIGN PATENT DOCUMENTS

| WO | WO 84/03564 | 9/1984 |
| WO | WO 88/06630 | 9/1988 |
| WO | WO 90/02909 | 3/1990 |
| WO | WO 92/09690 | 6/1992 |
| WO | WO 93/03367 | 2/1993 |
| WO | WO 00/30425 | 5/2002 |

OTHER PUBLICATIONS

Waterson R. Homo sapiens paroxonase 2 mRNA, GeneBank accession number AC 005021, submitted Dec. 21, 1999.*
Machiedo et al., Surg. Gyn. & Obstet., 152:757–759 [1981].
Morris et al., Am. J. Vet. Res., 47:2554–2565 [1986].
Hoffman et al., J. Vet. Int. Med., 6:89–95 [1992].
Wolff, New Eng. J. Med., 324:486–488 [1991].
Ohlsson et al., Nature, 348:550–552 [1990].
K.A. Schulman et al., JAMA, 266:3466–3471 [1991].
Anderson and Young, Quantitative Filter Hybridization, in Nucleic Acid Hybridization [1985].
Wahl, et al., Meth. Enzymol., 152:399–407 [1987].
Gobinda et al., PCR Methods Applic., 2:318–22 [1993].
Ozols, Biochem J., 338:265 [1999].
Mochizuki et al., Gene, 213:149[1998].
Wilson et al., Nature, 368:32 [1994].
Clendenning et al., Genomics, 35:586 [1996].
Primo–Parmo et al., Genomics, 33:498 [1996].
Sorenson et al., PNAS, 92:7187 [1995].
Shih et al., J. Clin. Invest., 97:1630 [1996].
Furlong et al., Chem. Biol. Interact., 87:35 [1993].
La Du et al., Chem. Biol. Interact., 87:25 [1993].
Adkins et al., Am. J. Hum. Gent., 52:598 [1993].
Hassett et al., Biochemistry, 30:10141 [1991].
Triglia et al., Nucleic Acids Res., 16:8186 [1988].
Lagerstrom et al., PCR Methods Applic., 1:111–19 [1991].
Parker et al., Nucleic Acids Res., 19:3055–60 [1991].
Murray et al., Nucl. Acids Res., 17 [1989].
Graham and van der Eb, Virol., 52:456 [1973].
Kacian et al., Proc. Natl. Acad. Sci. USA, 69:3038 [1972].
Gluzman, Cell 23:175 [1981].
Chamberlin et al., Nature, 228:227 [1970].
Wu and Wallace, Genomics, 4:560 [1989].
H.A. Erlich (ed.), PCR Technology, Stockton Press [1989].
Sambrook et al., Molecular Cloning: A Laboratory Manual, Cold Spring Harbor Press, NY, pp. 9.31–9.58 [1989].
Davis et al., Basic Methods in Molecular Biology, [1986].
Wilson et al., Cell, 37:767 [1984].
Ben–Bassat et al., J. Bacteriol., 169:751–757 [1987].
Miller et al., Proc. Natl. Acad. Sci. USA, 84:2718–1722 [1990].
Hochuli et al., J. Chromatogr., 411:177 [1987].
Janknecht et al., Proc. Natl. Acad. Sci. USA, 88:8972.
Stryer (ed.), *Biochemistry*, 2nd ed, WH Freeman and Co. [1981].
Narang, Tetrahedron Lett., 39:3 9 [1983].
Itakura et al., Recombinant DNA, in *Walton* (ed.), *Proceedings of the 3rd Cleveland Symposium on Macromolecules*, Elsevier, Amsterdam, pp. 273–289 [1981].
Itakura et al., Annu. Rev. Biochem., 53:323 [1984].
Itakura et al., Science 198:1056 [1984].
Ike et al., Nucl. Acid Res., 11:477 [1983].
Cwirla et al., Proc. Natl. Acad. Sci. USA, 87:6378–6382 [1990].
Fuchs et al., BioTechnol., 9:1370–1371 [1991].
Goward et al., TIBS 18:136–140 [1992].

(Continued)

*Primary Examiner*—Rebecca E. Prouty
*Assistant Examiner*—Malgorzata A. Walicka
(74) *Attorney, Agent, or Firm*—Medlen & Carroll, LLP

(57) ABSTRACT

The present invention relates to paraoxonase genes, in particular PON3. The present invention provides isolated nucleotide sequence encoding PON3, wild type and mutant PON3 peptides. The present invention also provides methods for using PON3 to screen compounds for the ability to alter PON3 associated activities, methods for generating antibodies useful in the detection of PON3, and methods of treating and preventing oxidative damage, sepsis, chemical toxicity, and other conditions.

7 Claims, 25 Drawing Sheets

OTHER PUBLICATIONS

Marks et al., J. Biol. Chem., 267:16007–16010 [1992].
Griffths et al., EMBO J., 12:725–734 [1993].
Clackson et al., Nature, 352:624–628 [1991].
Barbas et al., Proc. Natl. Acad. Sci., 89:4457–4461 [1992].
Ruf et al., Biochem., 33:1565–1572 [1994].
Wang et al., J. Biol. Chem., 269:3095–3099 [1994].
Balint et al. Gene 137:109–118 [1993].
Grodberg et al., Eur. J. Biochem., 218:597–601 [1993].
Nagashima et al., J. Biol. Chem., 268:2888–2892 [1993].
Lowman et al., Biochem., 30:10832–10838 [1991].
Cunningham et al., Science, 244:1081–1085 [1989].
Gustin et al., Virol., 193:653–660 [1993].
Brown et al., Mol. Cell. Biol., 12:2644–2652 [1992].
Meyers et al., Science, 232:613 [1986].
Caruthers et al., Nucl. Acids Res. Symp. Ser., 7:215–233 [1980].
Crea and Horn, Nucl. Acids Res., 9:2331 [1980].
Matteucci and Caruthers, Tetrahedron Lett., 21:719 [1980].
Chow and Kempe, Nucl. Acids Res., 9:2807–2817 [1981].
Creighton, *Proteins Structures And Molecular Principles,* W H Freeman and Co, New York N.Y. [1983].
Roberge et al., Science, 269:202–204 [1995].
Tjoelker et al., Nature, 374:549–553 [1995].
Granjeaudhae et al., Immunogenetics, 49:964–972 [1999].
Esterbauer et al., Free Radical Res Commun, 6:67–75 [1989].
El–Saadani et al., J Lipid Res, 30:627–630 [1989].
Smith et al., Gene 67:31 [1988].
Köhler and Milstein, Nature, 256:495–497 [1975].
Kozbor et al., Immunol. Tod., 4:72 [1983].
Johnson et al., Am. J. Patholo., 88, 559–574, [1977].
Aviram et al., Arterioscler. Thromb. Vasc. Biol. 18:1617–1624 [1998].
Aviram, Mol. Med. Today 5:381–138 [1999].
Watson et al., J. Clin. Invest 96:2882–2891 [1995].
Shih et al., Nature, 394:284–287 [1998].
Langman and Cole, Clin. Chim Acta, 286:63–80 [1999].
Jakubowski, J. Biol. Chem., 275:3957–2962 [2000].
Billecke, et al., Chem Biol Interact, 119–120:251–256, [1999].
Sorenson et al., Thromb. Vasc. Biol., 19:2214–2225 [1999].
Laemmli, Nature, 227:680–685, [1970].
Kuo and La Du, Drug Metab. Dispos., 23:935 [1995].
Gan et al., Drug Metab Dispos, 19:100–106 [1991].
Augustinsson and Axenfors, Anal. Biochem., 48:428 [1972].
Haley et al. Toxicol. Applied Pharmacol., 157:227–233, [1999].
Cote et al., Proc. Natl. Acad. Sci. USA, 80:2026–2030 [1983].
Kieft et al., J Lipid Res, 32:859–866 [1991].
Hatch, Adv. Lipid Res., 6:1 [1968].
Aurrand–Lioons et al., Immunity, 5:391–405 [1996].
Costa et al., "The role of paraoxonase (PON1) in the detoxication of organophosphates and its human polymorphism," Chem.–Biol. Interactions 119–120:429 [1999].
Zech et al., "Paraoxonase polymorphism in rabbits," Chemico–Biol. Interactions 119–120:283 [1999].
Hegele "Paraoxonase genes and diseases," Ann Med., 31:217 [1999].
Hegele et al. "Genetic variation in paraoxonase-2 is associated with variation in plasma lipoproteins in Canadian Oji–Cree," Clin. Genet. 54:394 [1998].

Rodrigo et al., "Purification and characterization of paroxon hydrolase from rat liver," Biochem J., 321:595 [1997].
Boright et al., "Genetic variation in paraoxonase–1 and paraoxonase–2 is associated with variation in plasma lipoproteins in Alberta Hutterites," Atherosclerosis 139:131 [1998].
La Du "Human serum paroxonase/arylesterase" Pharmacogenetics of Drug Metabolism, Pergamon Press, New York, pp. 51–91.
Li et al., "Paroxonase (Pon1) gene in mice: sequencing, chromosomal localization and developmental expression," Pharmacogenetics 7:137 [1997].
Sorenson et al., "Reconsideration of the catalytic center and mechanism of mammalian paraoxonase/arylesterase," PNAS, 92:7187 [1995].
Humbert et al., "The molecular basis of the human serum paraoxonase activity polymorphism," Nature Genetics 3:73 [1993].
Sorenson et al., "The genetic mapping and gene structure of mouse paraoxonase/arylesterase," Genomics 30:431 [1995].
Sorenson et al., "Properties of the retained N–terminal hydrophobic leader sequence in human serum paraoxonase/arylesterase," Chem Biol. Int. 119–120:599 [1999].
Josse et al., "Human serum paraoxonase (PONI): identification of essential amino acid residues by group–selective labelling and site–directed mutagenesis," Chemico–Biologic. Interactions 119–120:71 [1999].
Josse et al., "Tryptophan residue(s) as major components of the human serum paraoxonase active site," Chemico–Biologic. Interactions 119–120:79 [1999].
Doorn et al., "Evidence that several conserved histidine residues are required for hydrolytic activity of human paraoxonase/arylesterase activity," Chemico–Biologic. Interactions 119–120:235 [1999].
Josse et al., "Identification of residues essential for human paraoxonase (PONI) arylesterase/organophosphatase activities," Biochemistry 38:2816 [1999].
Mackness et al., "Polymorphisms of paraoxonase genes and low density lipoprotein lipid peroxidation," The Lancet 353:468 [1999].
Mackness et al. "Human serum paraoxonase," Gen. Pharmacol., 31:329 [1998](abstract).
Scanlan, "Evolution in Action," Chem. Biol., 2:71 [1995] (abstract).
Wang et al. "Differential expression of a cDNA clone in human liver versus hepatic cancer–highly homologous to aryl–dialkyl phosphatase" Cell Res., 7:79 [1997](abstract).
Furlong et al. "Purification of rabbit and human serum paraoxonase" Biochemistry 30:10133 [1991](abstract).
Smolen et al. "Characteristics of the genetically determined allozymic forms of human serum paraoxonase/arylesterase" Drug Metab. Dispos., 19:107 [1991](abstract).
Scott et al., Science, 249:386–390 [1980].
Roberts et al., Proc. Natl. Acad. Sci. USA, 89:2429–2433 [1992].
Devlin et al., Science, 249: 404–406 [1990].
Huse et al., Science, 246:1275–1281 [1989].
Cole et al., *in Monoclonal Antibodies and Cancer Therapy,* Alan R. Liss, Inc., pp. 77–96 [1985].
LaDu et al., Chem Biol Interact., 119–120:379–88, [1999].

\* cited by examiner

Figure 1

```
ttgtntgtngccacctggctcgccgggaccatggcgaagctcctgctgctgaccctgctg      60
                                M  A  K  L  L  L  T  L  L        10
                                            -  -  -
ggggccagcctcgccttcgtcggggagaggttgctggcgtttagaaacagctttggtgca     120
 G  A  S  L  A  F  V  G  E  R  L  L  A  F  R  N  S  F  G  A      30
                      V                                E
gttcaagaactggagccagtagaaccccagaactgtgtccttattgagggactcgaaaat     180
 V  Q  E  L  E  P  V  E  P  Q  N  C  V  L  I  E  G  L  E  N      50
       V           I                    H
ggctcggaagatattgatatacttcctagtgggctggcttttatctccagtggattaaaa     240
 G  S  E  D  I  D  I  L  P  S  G  L  A  F  I  S  S  G  L  K      70
tatccaggcatgccaaactttgcaccagatgagccaggaaaaaatcttcttgatagatatg    300
 Y  P  G  M  P  N  F  A  P  D  E  P  G  K  I  F  L  I  D  M      90
aatgagaagaacccaagagcacaagagctggaaatcagcaatgga***tttgaaaaagaa    360
 N  E  K  N  P  R  A  Q  E  L  E  I  S  N  G  *  F  E  K  E     110
                                           S
tcattcaatccacatgggatcagcactttcattgataaagaccatactgtgtatctttat    420
 S  F  N  P  H  G  I  S  T  F  I  D  K  D  H  T  V  Y  L  Y     130
                                        P
gttgtgaatcatccccacatgaagtctactgtggagatatttaaatttgaggaacaacaa    480
 V  V  N  H  P  H  M  K  S  T  V  E  I  F  K  F  E  E  Q  Q     150
             Q
cgctctcttgtacacctgaaaactataaaacatgaacttctcaagagtgtgaataacatt    540
 R  S  L  V  H  L  K  T  I  K  H  E  L  L  K  S  V  N  N  I     170
gtggttcttggaccggaacagttctacgccaccagagaccactattttaccaactatgtc    600
 V  V  L  G  P  E  Q  F  Y  A  T  R  D  H  Y  F  T  N  Y  V     190
ttagcacttcttgagatgttttttggatcttcactggacttccgttcttttctacagcccc    660
 L  A  L  L  E  M  F  L  D  L  H  W  T  S  V  L  F  Y  S  P     210
aaagaggtcaaagtggtggccaaaggattcagttctgccaatgggatcacagtctcacta    720
 K  E  V  K  V  V  A  K  G  F  S  S  A  N  G  I  T  V  S  L     230
gataagaagtatgtctatgttgctgatgccacagctaagaatgtgcatgtaatggaaaaa    780
 D  K  K  Y  V  Y  V  A  D  A  T  A  K  N  V  H  V  M  E  K     250
    Q
catgacaactgggatttaactgaactgaaggtaatacacttggacaccttagtggataat    840
 H  D  N  W  D  L  T  E  L  K  V  I  H  L  D  T  L  V  D  N     270
                            Q
ttgtctgttgatcctgccacgggagatatcttggcaggatgccatcctaatggcatgaag    900
 L  S  V  D  P  A  T  G  D  I  L  A  G  C  H  P  N  G  M  K     290
                                              P
cttctgaactataaccctgaggatcctccaggatcagaagtacttcgtatccagaatgtt    960
 L  L  N  Y  N  P  E  D  P  P  G  S  E  V  L  R  I  Q  N  V     310
                                                 V
ttgtctgagaagcccagggtgagcaccgtgtacaccaatgacggctctgtgcttcagggc   1020
 L  S  E  K  P  R  V  S  T  V  Y  T  N  D  G  S  V  L  Q  G     330
```

Figure 1 (Cont.)

```
tccaccgtggcttctgtgtaccaagggaagattctcataggcactatatttcacaaaact  1080
 S   T   V   A   S   V   Y   Q   G   K   I   L   I   G   T   I   F   H   K   T     350 ctgtattgtgtgctctagtctccagctcttccaaaaagtctacctgtttggtaaaagtaa  1140
 L   Y   C   V   L   Stop                                                           355
             D
atctttaaaggtgtgataattggaaccataagtaaataacaaataccaacaaaa                              1194
```

Figure 2

```
                          ----+----+----+----+----+----+----+
                              10        20        30        40        50        60        70
rabPON3_total       MAKLLLLTLLGASLAFVGERLLAFRNSFGAVQELEPVEPQNCVLIEGLENGSEDIDILPSGLAFISSGLK    70
PON3_Ozols.pr       ...LLLTLLGASLAFVGEVLLAFRNSFEAVQEVEPTEPQNCHLIEGLENGSEDIDILPSGLAFISSGLK    66
humanPON3aa         MGKLVALVLLGVGLSLVBEMFLAFRERVNASQEVEPVEPENCHLIEELESGSEDIDILPSGLSFISSELK    70
mus_pon3_aa.P       MGHLVALPLLGACLALIGERLLNFRERVSTTREIKATEPQNCHLIEGLENGSEDIDILPSGLAFISTGLK    70
rab_PON_1_Cle       MAKLTALTLLGLGLALFDGQKSSFQTRFNVHREVTPVELPNCNLVKGIDNGSEDLEILPNGLAFISAGLK    70
hum_pon1_aa.P       MAKLIALTLLGMGLALFRNHQSSYQTRLNALREVQPVELPNCNLVKGIETGSEDMEILPNGLAFISSGLK    70
rPON2aa             MGRLVAVSVLGIALALLGERLLALRNRLKASREIESVDLPNCHLIKGIEAGSEDIDILPNGLAFFSVGLK    70
hPON2aa             MGAWVGCGLAGDRAGFLGERLLALRNRLKASREVESVDLPHCHLIKGIEAGSEDIDILPNGLAFFSVGLK    70
uspatpro            MGRLVAVGLLGIALALLGERLLALRNRLKASREVESVDLPHCHLIKGIEAGSEDIDILPNGLAFLSVGLK    70

----+----+----+----+----+----+----+
                              80        90       100       110       120       130       140
rabPON3_total       YPGMPNFAPDEPGKIFLIDMNEKNPRAQELEISNG.FEKESFNPHGISTFIDKDHTVYLYVVNHPHMKST   139
PON3_Ozols.pr       YPGMPNFAPDEPGKIFLIDMNEKNPRAQELEISSG.FEKESFNPHGISTFIDKDPTVYLYVVNQPHMKST   135
humanPON3aa         YPGMPNFAPDEPGKIFLMDLNEQNPRAQALEISGG.FDKELFNPHGISIFIDKDNTVYLYVVNHPHMKST   139
mus_pon3_aa.P       YPGMPAFAPDKPGRIFLMDLNEQNPEAQALEISGG.LDQESLNPHGISTFIDKDNTAYLYVVNHPNMDST   139
rab_PON_1_Cle       YPGIMSFDPDKPGKILLMDLNEKDPVVLELSITGSTFDLSSFNPHGISTFTDEDNIVYLMVVNHPDSKST   140
hum_pon1_aa.P       YPGIKSFNPNSPGKILLMDLNEEDPTVLELGITGSKFDVSSFNPHGISTFTDEDNAMYLLVVNHPDAKST   140
Rpon2aa             CPGLHSFAPDKPGGILMMDLKEERPRALELRISRG.FDLASFNPHGISTFIDDDDTIYLFVVNHPEFKNT   139
Hpon2aa             FPGLHSFAPDKPGGILMMDLKEEKPRARELRISRG.FDLASFNPHGISTFIDNDDTVYLFVVNHPEFKNT   139
uspatpro            FPGLHSFAPDKPGGILMMVLKEAKPRGRELRISRG.FDLASFNPHGISTFIDNDDTVYLLVVNHPEFKNT   139
```

Figure 2 (Cont.)

```
                         150       160       170       180       190       200       210
                 ----+----|----+----|----+----|----+----|----+----|----+----|----+----|
rabPON3_total    VEIFKFEEQQRSLVHLKTIKHELLKSVNNITVVLGPEQFYATRDHYFTNYVLALLEMFLDLHWTSVLFYSP  209
PON3_Ozols.pr    VEIFKFEEQQRSLVHLKTIKHELLKSVNNITVVLGPEQFYATRDHYFTNYVLALLEMFLDLHWTSVLFYSP  205
humanPON3aa      VEIFKFEEQQRSLVYLKTIKHELLKSVNDIVVLGPEQFYATRDHYFTNSLLSFFEMILDLRWTYVLFYSP   209
mus_pon3_aa.P    VEIFKFEEQQRSLIHLKTLKHELLKSVNDIVVLGPEQFYATRDHYFTSYFLVLLEMILDPHWTSVVFYSP   210
rab_PON_1_Cle    VELFKFQEKEKSLLHLKTIRHKLPSVNDIVAVGPEHFYATNDHTFIDPYLKSWEMHLGLAWSFVTYYSP    210
hum_pon1_aa.P    VELFKFQEEEKSLLHLKTIRHKLLPNLNDIVAVGPEHFYGTNDHTFLDPYLQSWEMYLGLAWSYVVYYSP   209
rPON2aa          VEIFKFEEEENSLLHLKTIRHELLPSVNDVIAVGPAHFYATNDHYFSDPFLKYLETYLNLHWANVIYYSP   209
hPON2aa          VEIFKFEEAENSLLHLKTVKHELLPSVNDITAVGPAHFYATNDHYFSDPFLKYLGTYLNLHWANVVYYSP   209
uspatpro         VEIFNLEEAENSLLHLKTVKHELLPSVNDITAVGPAHFYATNDHYFSDPFLKYLETYLELHWANVVYYRP   209

220       230       240       250       260       270       280
                 ----+----|----+----|----+----|----+----|----+----|----+----|----+----|
rabPON3_total    KEVKVVA.KGFSSANGITVSLD.KKYVYVADATAKNVHVMEKGHDNWDLIELKVIHLDTLVDNLSVDPATG  277
PON3_Ozols.pr    KEVKVVA.KGFSSANGITVSGD.QKYVYVADATAKNVHVMEKGHDNWDLTQLKVIHLVTLVDNLSVDPATG  273
humanPON3aa      REVKVVA.KGFCSANGITVSAD.QKYVYVADVAAKNIHIMEKGHDNWDLTQLKVIQLGTLVDNLSVDPATG  277
mus_pon3_aa.P    KEVKVVA.QGFSSANGITVSLD.QKFVYVADVTAKNIHIMEKGHDNWDLTPVKVIQLGTLVDNLTVAPATG  277
rab_PON_1_Cle    NDVRVVA.EGFDFANGINISPD.GKYVYIAELLAHKIHVYEKHANWTLTPLKSLDFNTLVDNISVDPVTG   278
hum_pon1_aa.P    SEVRVVA.EGFDFANGINISPD.GKYVYIAELLAHKIHVYEKHANWTLTPLKSLDFNTLVDNISVDPETG   278
Rpon2aa          NEVKVVA.DGFDSANGINISPD.KKYIYVADILAXEIHVLDKHSNMNLTQLKVLQLDTLVDNLSVDPSSG   277
Hpon2aa          NEVKVVA.EGFDSANGINISPD.DKYIYVADILAHEIHVLEKHTNMNLTQLKVLELDTLVDNLSIDPSSG   277
uspatpro         NEVKGGSRKDLDSANGINISPGWISFSMLADILAHEIHVWGKHTNMNLTQLKVHTNMNLTQLKVLELDTLVDNLSIDPSSG  279
```

SDS PAGE of Concanavalin A column Purification of Rabbit Serum PON3

Lane 1 Protein standards
Lane 2 Gel filtration column pool
Lanes 3-10 Column fractions Western Blot of Rabbit PON3 Mutants Blue Agarose Fractions of Expression Medium
Lane 1 Purified rabbit serum PON3
Lane 2 Protein standards
Lane 3 rPON3 wt
Lane 4 rPON3 wt
Lane 5 rPON3 E46K* truncated
Lane 6 rPON3 N169D
Lane 7 rPON3 K243H
Lane 8 rPON3 L281W
Lane 9 rPON3 D324N
Lane 10 pcDNA3.1 vector Specific Activities of Rabbit PON3 Mutants with Lovastatin (Lst), Dihydrocomarin (DHC) and Phenyl Acetate (PhAc)

Figure 13

N169D rabbit PON3 mutant

```
                              atggcgaagctcctgctgctgaccctgctg    30
                              M  A  K  L  L  L  T  L  L        10 gggccagcctcgccttcgtcggggagaggttgctggcgtttagaaacagctttggtgca    90
G  A  S  L  A  F  V  G  E  R  L  L  A  F  R  N  S  F  G  A    30 gttcaagaactggagccagtagaaccccagaactgtgtccttattgagggactcgaaaat   150
V  Q  E  L  E  P  V  E  P  Q  N  C  V  L  I  E  G  L  E  N    50 ggctcggaagatattgatatacttcctagtgggctggcttttatctccagtggattaaaa   210
G  S  E  D  I  D  I  L  P  S  G  L  A  F  I  S  S  G  L  K    70 tatccaggcatgccaaactttgcaccagatgagccaggaaaaatcttcttgatagatatg   270
Y  P  G  M  P  N  F  A  P  D  E  P  G  K  I  F  L  I  D  M    90 aatgagaagaacccaagagcacaagagctggaaatcagcaatgga***tttgaaaagaa    330
N  E  K  N  P  R  A  Q  E  L  E  I  S  N  G  *  F  E  K  E   110 tcattcaatccacatgggatcagcactttcattgataaagaccatactgtgtatctttat   390
S  F  N  P  H  G  I  S  T  F  I  D  K  D  H  T  V  Y  L  Y   130 gttgtgaatcatccccacatgaagtctactgtggagatatttaaatttgaggaacaacaa   450
V  V  N  H  P  H  M  K  S  T  V  E  I  F  K  F  E  E  Q  Q   150 cgctctcttgtacacctgaaaactataaaacatgaacttctcaagagtgtgaatgacatt   510
R  S  L  V  H  L  K  T  I  K  H  E  L  L  K  S  V  N  D  I   170
                                                      _ gtggttcttggaccggaacagttctacgccaccagagaccactattttaccaactatgtc   570
V  V  L  G  P  E  Q  F  Y  A  T  R  D  H  Y  F  T  N  Y  V   190 ttagcacttcttgagatgtttttggatcttcactggacttccgttcttttctacagcccc   630
L  A  L  L  E  M  F  L  D  L  H  W  T  S  V  L  F  Y  S  P   210 aaagaggtcaaagtggtggccaaaggattcagttctgccaatgggatcacagtctcacta   690
K  E  V  K  V  V  A  K  G  F  S  S  A  N  G  I  T  V  S  L   230 gataagaagtatgtctatgttgctgatgccacagctaagaatgtgcatgtaatggaaaaa   750
D  K  K  Y  V  Y  V  A  D  A  T  A  K  N  V  H  V  M  E  K   250 catgacaactgggatttaactgaactgaaggtaatacacttggacaccttagtggataat   810
H  D  N  W  D  L  T  E  L  K  V  I  H  L  D  T  L  V  D  N   270 ttgtctgttgatcctgccacgggagatatcttggcaggatgccatcctaatggcatgaag   870
L  S  V  D  P  A  T  G  D  I  L  A  G  C  H  P  N  G  M  K   290 cttctgaactataaccctgaggatcctccaggatcagaagtacttcgtatccagaatgtt   930
L  L  N  Y  N  P  E  D  P  P  G  S  E  V  L  R  I  Q  N  V   310 ttgtctgagaagcccagggtgagcaccgtgtacaccaatgacggctctgtgcttcagggc   990
L  S  E  K  P  R  V  S  T  V  Y  T  N  D  G  S  V  L  Q  G   330
```

Figure 13 (Cont.)

```
tccaccgtggcttctgtgtaccaagggaagattctcataggcactatatttcacaaaact 1050
 S   T   V   A   S   V   Y   Q   G   K   I   L   I   G   T   I   F   H   K   T     350 ctgtattgtgtgctctagtctccagctcttccaaaaagtctacctgtttggtaaaagtaa 1110
 L   Y   C   V   L  Stop                                                             355
atctttaaaggtgtgataattggaaccataagtaaataacaaataccaacaaaa                 1164
```

Figure 14

K243H rabbit PON3 mutant

```
                                    atggcgaagctcctgctgctgaccctgctg    30
                                    M   A   K   L   L   L   T   L   L   10 ggggccagcctcgccttcgtcggggagaggttgctggcgtttagaaacagctttggtgca            90
G   A   S   L   A   F   V   G   E   R   L   L   A   F   R   N   S   F   G   A   30 gttcaagaactggagccagtagaaccccagaactgtgtccttattgagggactcgaaaat          150
V   Q   E   L   E   P   V   E   P   Q   N   C   V   L   I   E   G   L   E   N   50 ggctcggaagatattgatatacttcctagtgggctggcttttatctccagtggattaaaa         210
G   S   E   D   I   D   I   L   P   S   G   L   A   F   I   S   S   G   L   K   70 tatccaggcatgccaaactttgcaccagatgagccaggaaaaatcttcttgatagatatg         270
Y   P   G   M   P   N   F   A   P   D   E   P   G   K   I   F   L   I   D   M   90 aatgagaagaacccaagagcacaagagctggaaatcagcaatgga***tttgaaaaagaa         330
N   E   K   N   P   R   A   Q   E   L   E   I   S   N   G   *   F   E   K   E   110 tcattcaatccacatgggatcagcactttcattgataaagaccatactgtgtatctttat         390
S   F   N   P   H   G   I   S   T   F   I   D   K   D   H   T   V   Y   L   Y   130 gttgtgaatcatccccacatgaagtctactgtggagatatttaaatttgaggaacaacaa         450
V   V   N   H   P   H   M   K   S   T   V   E   I   F   K   F   E   E   Q   Q   150 cgctctcttgtacacctgaaaactataaaacatgaacttctcaagagtgtgaataacatt         510
R   S   L   V   H   L   K   T   I   K   H   E   L   L   K   S   V   N   N   I   170 gtggttcttggaccggaacagttctacgccaccagagaccactatttttaccaactatgtc        570
V   V   L   G   P   E   Q   F   Y   A   T   R   D   H   Y   F   T   N   Y   V   190 ttagcacttcttgagatgttttttggatcttcactggacttccgttctttctacagcccc        630
L   A   L   L   E   M   F   L   D   L   H   W   T   S   V   L   F   Y   S   P   210 aaagaggtcaaagtggtggccaaaggattcagttctgccaatgggatcacagtctcacta         690
K   E   V   K   V   V   A   K   G   F   S   S   A   N   G   I   T   V   S   L   230 gataagaagtatgtctatgttgctgatgccacagctcacaatgtgcatgtaatggaaaaa         750
D   K   K   Y   V   Y   V   A   D   A   T   A   H   N   V   H   V   M   E   K   250 catgacaactgggatttaactgaactgaaggtaatacacttggacaccttagtggataat         810
H   D   N   W   D   L   T   E   L   K   V   I   H   L   D   T   L   V   D   N   270 ttgtctgttgatcctgccacgggagatatcttggcaggatgccatcctaatggcatgaag         870
L   S   V   D   P   A   T   G   D   I   L   A   G   C   H   P   N   G   M   K   290 cttctgaactataaccctgaggatcctccaggatcagaagtacttcgtatccagaatgtt         930
L   L   N   Y   N   P   E   D   P   P   G   S   E   V   L   R   I   Q   N   V   310
```

Figure 14 (Cont.)

```
ttgtctgagaagcccagggtgagcaccgtgtacaccaatgacggctctgtgcttcagggc  990
 L   S   E   K   P   R   V   S   T   V   Y   T   N   D   G   S   V   L   Q   G   330 tccaccgtggcttctgtgtaccaagggaagattctcataggcactatatttcacaaaact 1050
 S   T   V   A   S   V   Y   Q   G   K   I   L   I   G   T   I   F   H   K   T   350 ctgtattgtgtgctctagtctccagctcttccaaaaagtctacctgtttggtaaaagtaa 1110
 L   Y   C   V   L  Stop
                                                              355
atctttaaaggtgtgataattggaaccataagtaaataacaaataccaacaaaa        1164
```

Figure 15

L281W rabbit PON3 mutant

```
                                    atggcgaagctcctgctgctgaccctgctg    30
                                     M  A  K  L  L  L  L  T  L  L     10 ggggccagcctcgccttcgtcggggagaggttgctggcgtttagaaacagctttggtgca          90
 G  A  S  L  A  F  V  G  E  R  L  L  A  F  R  N  S  F  G  A          30 gttcaagaactggagccagtagaaccccagaactgtgtccttattgagggactcgaaaat         150
 V  Q  E  L  E  P  V  E  P  Q  N  C  V  L  I  E  G  L  E  N          50 ggctcggaagatattgatatacttcctagtgggctggcttttatctccagtggattaaaa        210
 G  S  E  D  I  D  I  L  P  S  G  L  A  F  I  S  S  G  L  K          70 tatccaggcatgccaaactttgcaccagatgagccaggaaaaatcttcttgatagatatg        270
 Y  P  G  M  P  N  F  A  P  D  E  P  G  K  I  F  L  I  D  M          90 aatgagaagaacccaagagcacaagagctggaaatcagcaatgga***tttgaaaaagaa        330
 N  E  K  N  P  R  A  Q  E  L  E  I  S  N  G  *  F  E  K  E         110 tcattcaatccacatgggatcagcactttcattgataaagaccatactgtgtatctttat        390
 S  F  N  P  H  G  I  S  T  F  I  D  K  D  H  T  V  Y  L  Y         130 gttgtgaatcatccccacatgaagtctactgtggagatatttaaatttgaggaacaacaa        450
 V  V  N  H  P  H  M  K  S  T  V  E  I  F  K  F  E  E  Q  Q         150 cgctctcttgtacacctgaaaactataaaacatgaacttctcaagagtgtgaataacatt        510
 R  S  L  V  H  L  K  T  I  K  H  E  L  L  K  S  V  N  N  I         170 gtggttcttggaccggaacagttctacgccaccagagaccactattttaccaactatgtc        570
 V  V  L  G  P  E  Q  F  Y  A  T  R  D  H  Y  F  T  N  Y  V         190 ttagcacttcttgagatgttttggatcttcactggacttccgttctttttctacagcccc        630
 L  A  L  L  E  M  F  L  D  L  H  W  T  S  V  L  F  Y  S  P         210 aaagaggtcaaagtggtggccaaaggattcagttctgccaatgggatcacagtctcacta        690
 K  E  V  K  V  V  A  K  G  F  S  S  A  N  G  I  T  V  S  L         230 gataagaagtatgtctatgttgctgatgccacagctaagaatgtgcatgtaatggaaaaa        750
 D  K  K  Y  V  Y  V  A  D  A  T  A  K  N  V  H  V  M  E  K         250 catgacaactgggatttaactgaactgaaggtaatacacttggacaccttagtggataat        810
 H  D  N  W  D  L  T  E  L  K  V  I  H  L  D  T  L  V  D  N         270 ttgtctgttgatcctgccacgggagatatctgggcaggatgccatcctaatggcatgaag        870
 L  S  V  D  P  A  T  G  D  I  W  A  G  C  H  P  N  G  M  K         290 cttctgaactataaccctgaggatcctccaggatcagaagtacttcgtatccagaatgtt        930
 L  L  N  Y  N  P  E  D  P  P  G  S  E  V  L  R  I  Q  N  V         310
```

Figure 15 (Cont.)

```
ttgtctgagaagcccagggtgagcaccgtgtacaccaatgacggctctgtgcttcagggc  990
 L  S  E  K  P  R  V  S  T  V  Y  T  N  D  G  S  V  L  Q  G   330 tccaccgtggcttctgtgtaccaagggaagattctcataggcactatatttcacaaaact 1050
 S  T  V  A  S  V  Y  Q  G  K  I  L  I  G  T  I  F  H  K  T   350 ctgtattgtgtgctctagtctccagctcttccaaaaagtctacctgtttggtaaaagtaa 1110
 L  Y  C  V  L  Stop                                            355
atctttaaaggtgtgataattggaaccataagtaaataacaaataccaacaaaa        1164
```

Figure 16

D324N rabbit PON3 mutant

```
                                  atggcgaagctcctgctgctgaccctgctg   30
                                   M  A  K  L  L  L  T  L  L       10 ggggccagcctcgccttcgtcggggagaggttgctggcgtttagaaacagctttggtgca      90
 G  A  S  L  A  F  V  G  E  R  L  L  A  F  R  N  S  F  G  A       30 gttcaagaactggagccagtagaaccccagaactgtgtccttattgagggactcgaaaat    150
 V  Q  E  L  E  P  V  E  P  Q  N  C  V  L  I  E  G  L  E  N       50 ggctcggaagatattgatatacttcctagtgggctggcttttatctccagtggattaaaa    210
 G  S  E  D  I  D  I  L  P  S  G  L  A  F  I  S  S  G  L  K       70 tatccaggcatgccaaactttgcaccagatgagccaggaaaaatcttcttgatagatatg    270
 Y  P  G  M  P  N  F  A  P  D  E  P  G  K  I  F  L  I  D  M       90 aatgagaagaacccaagagcacaagagctggaaatcagcaatgga***tttgaaaagaa     330
 N  E  K  N  P  R  A  Q  E  L  E  I  S  N  G  *  F  E  K  E      110 tcattcaatccacatgggatcagcactttcattgataaagaccatactgtgtatctttat    390
 S  F  N  P  H  G  I  S  T  F  I  D  K  D  H  T  V  Y  L  Y      130 gttgtgaatcatccccacatgaagtctactgtggagatatttaaatttgaggaacaacaa    450
 V  V  N  H  P  H  M  K  S  T  V  E  I  F  K  F  E  E  Q  Q      150 cgctctcttgtacacctgaaaactataaaacatgaacttctcaagagtgtgaataacatt    510
 R  S  L  V  H  L  K  T  I  K  H  E  L  L  K  S  V  N  N  I      170 gtggttcttggaccggaacagttctacgccaccagagaccactatttaccaactatgtc    570
 V  V  L  G  P  E  Q  F  Y  A  T  R  D  H  Y  F  T  N  Y  V      190 ttagcacttcttgagatgttttggatcttcactggacttccgttcttttctacagcccc    630
 L  A  L  L  E  M  F  L  D  L  H  W  T  S  V  L  F  Y  S  P      210 aaagaggtcaaagtggtggccaaaggattcagttctgccaatgggatcacagtctcacta    690
 K  E  V  K  V  V  A  K  G  F  S  S  A  N  G  I  T  V  S  L      230 gataagaagtatgtctatgttgctgatgccacagctaagaatgtgcatgtaatggaaaaa    750
 D  K  K  Y  V  Y  V  A  D  A  T  A  K  N  V  H  V  M  E  K      250 catgacaactgggatttaactgaactgaaggtaatacacttggacaccttagtggataat    810
 H  D  N  W  D  L  T  E  L  K  V  I  H  L  D  T  L  V  D  N      270 ttgtctgttgatcctgccacgggagatatcttggcaggatgccatcctaatggcatgaag    870
 L  S  V  D  P  A  T  G  D  I  L  A  G  C  H  P  N  G  M  K      290 cttctgaactataaccctgaggatcctccaggatcagaagtacttcgtatccagaatgtt    930
 L  L  N  Y  N  P  E  D  P  P  G  S  E  V  L  R  I  Q  N  V      310
```

Figure 16 (Cont.)

```
ttgtctgagaagcccagggtgagcaccgtgtacaccaataacggctctgtgcttcagggc  990
 L  S  E  K  P  R  V  S  T  V  Y  T  N  N  G  S  V  L  Q  G   330 tccaccgtggcttctgtgtaccaagggaagattctcataggcactatatttcacaaaact 1050
 S  T  V  A  S  V  Y  Q  G  K  I  L  I  G  T  I  F  H  K  T   350 ctgtattgtgtgctctagtctccagctcttccaaaaagtctacctgtttggtaaaagtaa 1110
 L  Y  C  V  L  Stop                                           355
atctttaaaggtgtgataattggaaccataagtaaataacaaataccaacaaaa        1164
```

Figure 17

E46K truncated rabbit PON3 mutant

```
                              atggcgaagctcctgctgctgaccctgctg   30
                               M  A  K  L  L  L  T  L  L      10 ggggccagcctcgccttcgtcggggagaggttgctggcgtttagaaacagctttggtgca   90
 G  A  S  L  A  F  V  G  E  R  L  L  A  F  R  N  S  F  G  A  30 gttcaagaactggagccagtagaaccccagaactgtgtccttattaagggactcgaaaat  150
 V  Q  E  L  E  P  V  E  P  Q  N  C  V  L  I  K  G  L  E  N  50 ggctcggaagatattgatatacttcctagtgggctggcttttatctccagtggattaaaa  210
 G  S  E  D  I  D  I  L  P  S  G  L  A  F  I  S  S  G  L  K  70 tatccaggcatgccaaactttgcaccagatgagccaggaaaaatcttcttgatagatatg  270
 Y  P  G  M  P  N  F  A  P  D  E  P  G  K  I  F  L  I  D  M  90 aatgagaagaacccaagagcacaagagctggaaatcagcaatgga***tttgaaaaagaa  330
 N  E  K  N  P  R  A  Q  E  L  E  I  S  N  G  *  F  E  K  E  110 tcattcaatccacatgggatcagcactttcattgataaagaccatactgtgtatctttat  390
 S  F  N  P  H  G  I  S  T  F  I  D  K  D  H  T  V  Y  L  Y  130 gttgtgaatcatccccacatgaagtctactgtggagatatttaaatttgaggaacaacaa  450
 V  V  N  H  P  H  M  K  S  T  V  E  I  F  K  F  E  E  Q  Q  150 cgctctcttgtacacctgaaaactataaaacatgaacttctcaagagtgtgaataacatt  510
 R  S  L  V  H  L  K  T  I  K  H  E  L  L  K  S  V  N  N  I  170 gtggttcttggaccggaacagttctacgccaccagagaccactattttaccaactatgtc  570
 V  V  L  G  P  E  Q  F  Y  A  T  R  D  H  Y  F  T  N  Y  V  190 ttagcacttcttgagatgttttggatcttcactggacttccgttcttttctacagcccc  630
 L  A  L  L  E  M  F  L  D  L  H  W  T  S  V  L  F  Y  S  P  210 aaagaggtcaaagtggtggccaaaggattcagttctgccaatgggatcacagtctcacta  690
 K  E  V  K  V  V  A  K  G  F  S  S  A  N  G  I  T  V  S  L  230 gataagaagtatgtctatgttgctgatgccacagctaagaatgtgcatgtaatggaaaaa  750
 D  K  K  Y  V  Y  V  A  D  A  T  A  K  N  V  H  V  M  E  K  250 catgacaactgggatttaactgaactgaaggtaatacacttggacaccttagtggataat  810
 H  D  N  W  D  L  T  E  L  K  V  I  H  L  D  T  L  V  D  N  270 ttgtctgttgatcctgccacgggagatatcttggcaggatgccatcctaatggcatgaag  870
 L  S  V  D  P  A  T  G  D  I  L  A  G  C  H  P  N  G  M  K  290 cttctgaactataaccctgaggatcctccaggatcagaagtacttcgtatccagaatgtt  930
 L  L  N  Y  N  P  E  D  P  P  G  S  E  V  L  R  I  Q  N  V  310
```

Figure 17 (Cont.)

```
ttgtctgagaagcccagggtgagcaccgtgtaaaccaatgacggctctgtgcttcagggc    990
 L   S   E   K   P   R   V   S   T   V  Stop                   319 tccaccgtggcttctgtgtaccaagggaagattctcataggcactatatttcacaaaact  1050 ctgtattgtgtgctctagtctccagctcttccaaaaagtctacctgtttggtaaaagtaa  1110 atctttaaaggtgtgataattggaaccataagtaaataacaaataccaacaaaa        1164
```

PON3 AND USES THEREOF

CROSS REFERENCE TO RELATED APPLICATIONS

This application is a divisional of the U.S. Ser. No. 09/574,377 filed May 19, 2000, now U.S. Pat. No. 6,573,370.

FIELD OF THE INVENTION

The present invention relates to compositions comprising paroxonase 3 genes and polypeptides, in particular to compositions comprising rabbit PON3 genes and polypeptides. The present invention also provides methods for using PON3 genes and peptides in the treatment of endotoxemia, oxidative damage, chemical toxicity, and other conditions.

BACKGROUND OF THE INVENTION

Endotoxic shock is a condition, often fatal, provoked by the release of lipopolysaccharide (LPS) from the outer membrane of most gram negative bacteria (e.g., *Escherichia coli; Salmonella tymphimurium*). One example of a condition involving Endotoxic shock is sepsis. Sepsis is a major cause of morbidity and mortality in humans and other animals. It is estimated that 400,000–500,000 episodes of sepsis resulted in 100,000–175,000 human deaths in the U.S. alone in 1991. Sepsis has become the leading cause of death in intensive care units among patients with non-traumatic illnesses (Machiedo et al., Surg. Gyn. & Obstet., 152:757–759 [1981]). It is also the leading cause of death in young livestock, affecting 7.5–29% of neonatal calves (Morris et al., Am. J. Vet. Res., 47:2554–2565 [1986]), and is a common medical problem in neonatal foals (Hoffman et al., J. Vet. Int. Med., 6:89–95 [1992]). Despite the major advances of the past several decades in the treatment of serious infections, the incidence and mortality due to sepsis continues to rise (Wolff, New Eng. J. Med., 324:486–488 [1991]).

Sepsis is a systemic reaction characterized by arterial hypotension, metabolic acidosis, decreased systemic vascular resistance, tachypnea and organ dysfunction. Sepsis can result from septicemia (i.e., organisms, their metabolic endproducts or toxins in the blood stream), including bacteremia (i.e., bacteria in the blood), as well as toxemia (i.e., toxins in the blood), including endotoxemia (i.e., endotoxin in the blood). The term "bacteremia" includes occult bacteremia observed in young febrile children with no apparent foci of infection. The term "sepsis" also encompasses fungemia (i.e., fungi in the blood), viremia (i.e., viruses or virus particles in the blood), and parasitemia (i.e., helminthic or protozoan parasites in the blood). Thus, septicemia and septic shock (acute circulatory failure resulting from septicemia often associated with multiple organ failure and a high mortality rate) may be caused by a number of organisms.

The systemic invasion of microorganisms presents two distinct problems. First, the growth of the microorganisms can directly damage tissues, organs, and vascular function. Second, toxic components of the microorganisms can lead to rapid systemic inflammatory responses that can quickly damage vital organs and lead to circulatory collapse (i.e., septic shock) and oftentimes, death.

There are three major types of sepsis characterized by the type of infecting organism. Gram-negative sepsis is the most common and has a case fatality rate of about 35%. The majority of these infections are caused by *Escherichia coli, Klebsiella pneumoniae* and *Pseudomonas aeruginosa*. Gram-positive pathogens such as the staphylococci and streptococci are the second major cause of sepsis. The third major group includes the fungi, with fungal infections causing a relatively small percentage of sepsis cases, but with a high mortality rate.

Many of these infections are acquired in a hospital setting and can result from certain types of surgery (e.g., abdominal procedures), immune suppression due to cancer or transplantation therapy, immune deficiency diseases, and exposure through intravenous catheters. Sepsis is also commonly caused by trauma, difficult newborn deliveries, and intestinal torsion (especially in dogs and horses).

Many patients with septicemia or suspected septicemia exhibit a rapid decline over a 24–48 hour period. Thus, rapid methods of diagnosis and treatment delivery are essential for effective patient care. Unfortunately, a confirmed diagnosis as to the type of infection traditionally requires microbiological analysis involving inoculation of blood cultures, incubation for 18–24 hours, plating the causative organism on solid media, another incubation period, and final identification 1–2 days later. Therefore, therapy must be initiated without any knowledge of the type and species of the pathogen, and with no means of knowing the extent of the infection.

It is widely believed that anti-endotoxin antibody treatment administered after sepsis is established may yield little benefit because these antibodies cannot reverse the inflammatory cascade initiated by endotoxin. In addition, the high cost of each antibody (Centoxin II-1A was expected to cost $3700 per 100 mg dose) would limit physicians' use of a product where no clear benefit has been demonstrated (K. A. Schulman et al., JAMA, 266:3466–3471 [1991]). Of course, these endotoxin antibodies only target gram-negative sepsis; no equivalent antibodies exist for the array of gram-positive organisms and fungi.

With new knowledge regarding the effects of endotoxin on host inflammatory responses, other therapies are being attempted. For example, an IL-1 receptor antagonist has been identified that occupies the same receptor site as IL-1, but mediates no biological effect. Blockage of the IL-1 receptor with this molecule can reduce mortality from endotoxin shock. (Ohlsson et al., Nature, 348:550–552 [1990]). While the IL-1 receptor antagonist appears to be well-tolerated, the required dosage is extremely large (over 100 mg of recombinant protein per kg of body weight is infused over a period of hours to days). For human therapy, the 8–10 grams of recombinant protein anticipated to be required is likely to be extremely costly (several thousand dollars).

Clearly, there is a great need for agents capable of preventing and treating sepsis. It would be desirable if such agents could be administered in a cost-effective fashion. Furthermore, approaches are needed to combat all forms of sepsis, not just gram-negative cases.

SUMMARY OF THE INVENTION

The present invention relates to compositions comprising paroxonase 3 genes and polypeptides, in particular to compositions comprising rabbit PON3 genes and polypeptides. The present invention also provides methods for using PON3 genes and peptides in the treatment of endotoxemia, oxidative damage, chemical toxicity, and other conditions.

For example, the present invention provides compositions comprising a nucleic acid sequence comprising at least a portion of a gene encoding rabbit PON-3 (e.g., a portion encoding a biologically active PON-3 polypeptide). In some embodiments, the nucleic acid sequence comprises SEQ ID NO:7 or a portion of SEQ ID NO:7 (e.g., a portion encoding a biologically active PON-3 polypeptide such as the PON-3 functional domains described herein). In certain embodiments, the nucleic acid sequence comprises a truncation of SEQ ID NO:7. In some embodiments, the nucleic acid comprises a PON-3 variant sequence. Although the present invention is not limited by the identity of the variant sequences, in some embodiments the variants include, but are not limit to, SEQ ID NOs:9, 11, 13, 15, and 17 or peptide sequences 10, 12, 14, 16, and 18.

The present invention also provides polypeptides encoded by the above nucleic acid sequences. For example, the present invention provides the polypeptide SEQ ID NO:8. In preferred embodiments of the present invention, the present invention provides biologically active rabbit PON3 polypeptides or polypeptide fragments. In certain embodiments, the polypeptides further comprise non-rabbit PON-3 polypeptide sequences (e.g., a biologically active rabbit PON3 polypeptide is provided as a chimera with a human PON3 polypeptide sequence).

The present invention also provides methods comprising providing: a biologically active PON3 polypeptide or polypeptide fragment (e.g., including, but not limited to any of the above peptides), a host, and a delivery system; and administering the biologically active rabbit PON3 polypeptide or fragment to the host using the delivery system. The present invention is not limited by the nature of the host. For example, host include, but are not limited to humans and non-human mammals. The host may be treated for any number of reasons. In some embodiments, the host is further treated with other PON polypeptides (e.g., PON-1 and/or PON-2 polypeptides), for example, in a mixture with PON-3. While the present invention is not limited by the nature of the host, in preferred embodiments, the host is a host suspected of having sepsis or known to have sepsis and hosts suspected as being susceptible to sepsis.

DESCRIPTION OF THE FIGURES

FIG. 1 shows the nucleotide (SEQ ID NO:7) and polypeptide (SEQ ID NO:8) sequences of rabbit PON3 used in some embodiments of the present invention.

FIG. 13 shows the nucleotide sequence (SEQ ID NO:9) and polypeptide sequence (SEQ ID NO: 10) of the N169 rabbit PON3 mutant used in some embodiments of the present invention.

FIG. 14 shows the nucleotide (SEQ ID NO:11) and polypeptide (SEQ ID NO: 12) sequences of the K243H rabbit PON3 mutant used in some embodiments of the present invention.

FIG. 15 shows the nucleotide (SEQ ID NO:13) and polypeptide (SEQ ID NO:14) sequences of the L281 rabbit PON3 mutant used in some embodiments of the present invention.

FIG. 16 shows the nucleotide (SEQ ID NO:15) and polypeptide (SEQ ID NO:16) sequences of the D324N rabbit PON3 mutant used in some embodiments of the present invention.

FIG. 17 shows the nucleotide (SEQ ID NO:17) and polypeptide (SEQ ID NO:18) sequences of the E46K rabbit PON3 mutant used in some embodiments of the present invention.

GENERAL DESCRIPTION OF THE INVENTION

Figure 2:
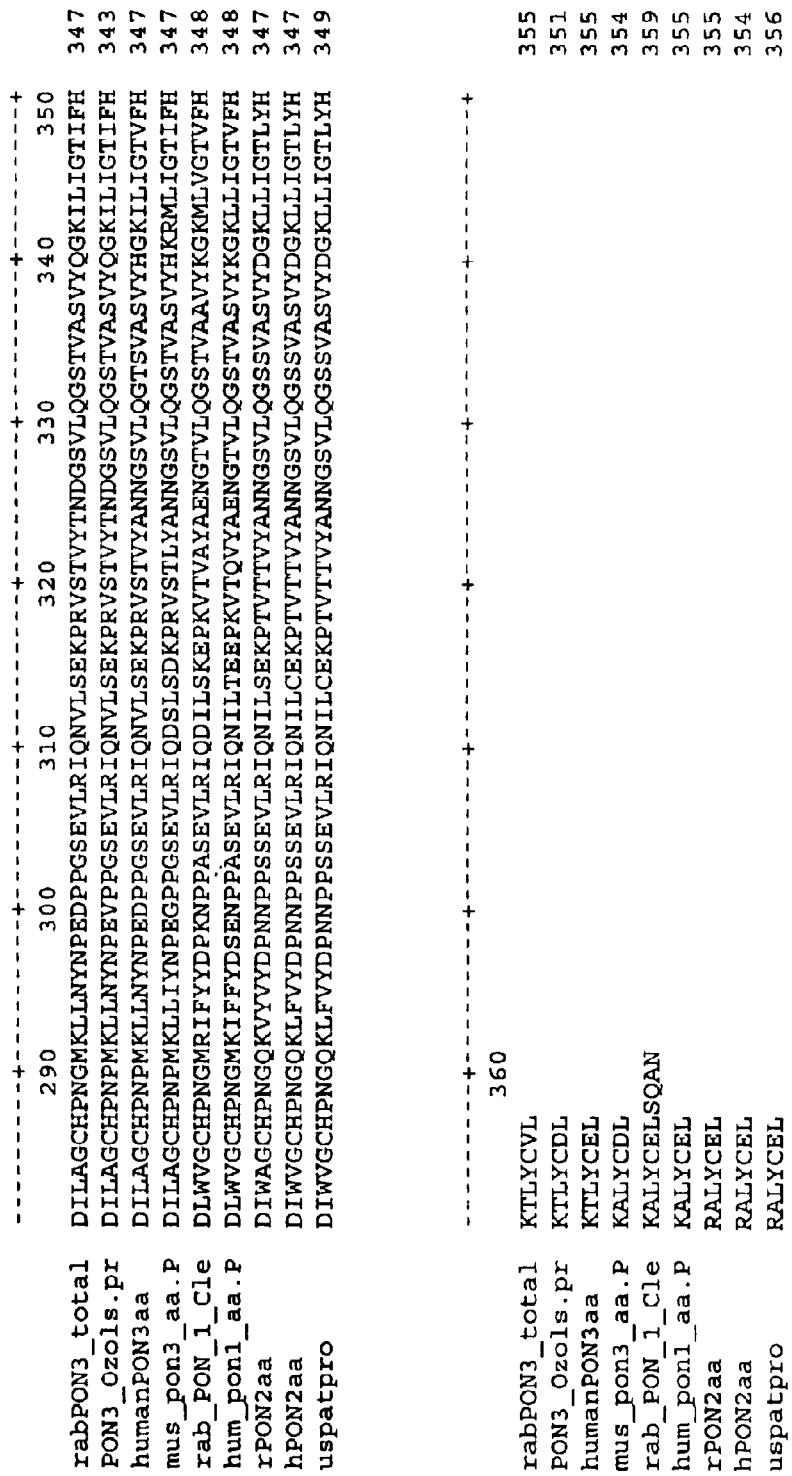
FIG. 2 shows the alignment of the PON3 polypeptide sequence used in some embodiments of the present invention with other known PON3 sequences.

The present invention relates to compositions comprising paroxonase 3 genes and polypeptides, in particular to compositions comprising rabbit PON3 genes and polypeptides. The present invention also provides methods for using PON3 genes and peptides in the treatment of endotoxemia, oxidative damage, chemical toxicity, and other conditions.

In some embodiments, the present invention provides novel nucleic acid sequences of the rabbit Pon3 gene. In other embodiments, the present invention provides mutants, variants, homologs, chimeras, and fusions of rabbit Pon3. In some embodiments, the present invention provides methods of generating such sequences. In additional embodiments, the present invention provides methods of cloning, expressing, purifying, and assaying the biochemical activity of wild type as well as mutants, variants, homologs, chimeras, and fusions of Pon3.

In some embodiments, the present invention provides novel PON3 polypeptides purified from rabbit serum. In other embodiments, the present invention provides mutants, variants, homologs, chimeras, and fusion proteins of rabbit PON3. In some embodiments, the present invention provides methods of assaying the biochemical activity of such proteins. In additional embodiments, the present inventions provides methods of assaying the biochemical activity of additional PON3 polypeptides. In still further embodiments, the present invention provides methods of generating antibodies to PON3. In yet another embodiment, the present invention provides an assay for the screening of drugs that affect lactone metabolism or other biological activities of PON3.

The compositions of the present invention find use in the prevention and treatment of diseases and pathological conditions related to lactone production. Therapeutic treatments for sepsis, oxidative damage, and chemical toxicity are provided. The polypeptides of the present invention provide an easy to produce, low cost, pharmaceutical agent for the prevention and treatment of the aforementioned pathological conditions.

Definitions

To facilitate understanding of the invention, a number of terms are defined below.

As used herein, the term "Pon3" refers to a gene that encodes a "PON3" protein.

The term "gene" refers to a nucleic acid (e.g., DNA) sequence that comprises coding sequences necessary for the production of a polypeptide or precursor (e.g., PON3). The polypeptide can be encoded by a full length coding sequence or by any portion of the coding sequence so long as the desired activity or functional properties (e.g., enzymatic activity, ligand binding, etc.) of the full-length or fragment are retained. The term also encompasses the coding region of a structural gene and the including sequences located adjacent to the coding region on both the 5' and 3' ends for a distance of about 1 kb on either end such that the gene corresponds to the length of the full-length mRNA. The sequences that are located 5' of the coding region and which are present on the mRNA are referred to as 5' untranslated sequences. The sequences that are located 3' or downstream of the coding region and that are present on the mRNA are referred to as 3' untranslated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (mRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In particular, the term "Pon3 gene" (or Pon3) refers to the full-length Pon3 nucleotide sequence (e.g., contained in SEQ ID NO:7), as well as variants, homologs, and mutants of the full length Pon3 nucleotide sequence. However, it is also intended that the term encompass fragments of the Pon3 sequence, as well as other domains within the full-length Pon3 nucleotide sequence. Furthermore, the terms "Pon3 nucleotide sequence" or "Pon3 polynucleotide sequence" encompasses DNA, cDNA, and RNA (e.g., mRNA) sequences.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The term "wild-type" refers to a gene or gene product that has the characteristics of that gene or gene product when isolated from a naturally occurring source. A wild-type gene is that which is most frequently observed in a population and is thus arbitrarily designed the "normal" or "wild-type" form of the gene. In contrast, the terms "modified", "mutant", and "variant" refer to a gene or gene product that displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

DNA molecules are said to have "5' ends" and "3' ends" because mononucleotides are reacted to make oligonucleotides or polynucleotides in a manner such that the 5' phosphate of one mononucleotide pentose ring is attached to the 3' oxygen of its neighbor in one direction via a phosphodiester linkage. Therefore, an end of an oligonucleotides or polynucleotide, referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements that direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

As used herein, the terms "an oligonucleotide having a nucleotide sequence encoding a gene" and "polynucleotide having a nucleotide sequence encoding a gene," means a nucleic acid sequence comprising the coding region of a gene or, in other words, the nucleic acid sequence that encodes a gene product. The coding region may be present in either a cDNA, genomic DNA, or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "regulatory element" refers to a genetic element that controls some aspect of the expression of nucleic acid sequences. For example, a promoter is a regulatory element that facilitates the initiation of transcription of an operably linked coding region. Other regulatory elements include splicing signals, polyadenylation signals, termination signals, etc.

As used herein, the terms "complementary" or "complementarity" are used in reference to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" refers to a degree of complementarity. There may be partial homology or complete homology (i.e., identity). A partially complementary sequence is one that at least partially inhibits a completely complementary sequence from hybridizing to a target nucleic acid and is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous sequence to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that lacks even a partial degree of complementarity (e.g., less than about 30% identity); in the absence of non-specific binding the probe will not hybridize to the second non-complementary target.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.).

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids.

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m = 81.5 + 0.41(\% \text{ G+C})$, when a nucleic acid is in aqueous solution at 1 M NaCl (See e.g., Anderson and Young, Quantitative Filter Hybridization, in *Nucleic Acid Hybridization* [1985]). Table 4 (pg. 97) entitled "Preparation of Standard Hybridisation Solution Containing Formamide" provides instruction for making hybridisation buffer Solution A Mix Together:

| | |
|---|---|
| Deionised formamide | 50 ml |
| 20 × SSC | 25 ml |
| 100 × Denhardt's solution | 1 ml |
| 1 M sodium phosphate buffer, pH 6.8 | 2 ml |
| 20% SDS | 1 ml |
| Dextran sulphate (mol. wt. 500 000) | 10 g | stir until the dextran sulphate has dissolved. Adjust the volume to 95.5 ml.

Solution B

Mix Together:

| | |
|---|---|
| Sonicated DNA (5 mg/ml) | 2 ml |
| Poly (C) [5 mg/ml] | 0.2 ml |
| Poly (A) [5 mg/ml] | 0.2 ml |
| Yeast tRNA (5 mg/ml) | 2 ml |

Add solution b to solution A and store at 4° C.

"The composition of SSC is 0.15 M NaCl, 0.015 M trisodium citrate, pH 7.0." (Page 96) "100× Denhardt's solution contains 2% Ficoll (mol. wt. 400 000), 2% polyvinyl pyrrolidone (mol. wt. 400 000) and 2% bovine serum albumin . . . " (Page 96).

"For a moderately stringent wash, wash the filter twice in 400 ml of 2×SSC, 0.1% SDS at 60° C. for 1 h. For a higher stringency wash, treat the filter for 2×1 h at 65° C. in 0.1×SSC, 0.1% SDS." (Page 97).

Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. Those skilled in the art will recognize that "stringency" conditions may be altered by varying the parameters just described either individually or in concert. With "high stringency" conditions, nucleic acid base pairing will occur only between nucleic acid fragments that have a high frequency of complementary base sequences (e.g., hybridization under "high stringency" conditions may occur between homologs with about 85–100% identity, preferably about 70–100% identity). With medium stringency conditions, nucleic acid base pairing will occur between nucleic acids with an intermediate frequency of complementary base sequences (e.g., hybridization under "medium stringency" conditions may occur between homologs with about 50–70% identity). Thus, conditions of "weak" or "low" stringency are often required with nucleic acids that are derived from organisms that are genetically diverse, as the frequency of complementary sequences is usually less.

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Qβ replicase, MDV-1 RNA is the specific template for the replicase (Kacian et al., Proc. Natl. Acad. Sci. USA, 69:3038 [1972]). Other nucleic acid will not be replicated by this amplification enzyme. Similarly, in the case of T7 RNA polymerase, this amplification enzyme has a stringent specificity for its own promoters (Chamberlin et al., Nature, 228:227 [1970]). In the case of T4 DNA ligase, the enzyme will not ligate the two oligonucleotides or polynucleotides, where there is a mismatch between the oligonucleotide or polynucleotide substrate and the template at the ligation junction (Wu and Wallace, Genomics, 4:560 [1989]). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.), *PCR Technology*, Stockton Press [1989]).

As used herein, the term "amplifiable nucleic acid" is used in reference to nucleic acids that may be amplified by any amplification method. It is contemplated that "amplifiable nucleic acid" will usually comprise "sample template."

As used herein, the term "sample template" refers to nucleic acid originating from a sample that is analyzed for the presence of "target" (defined below). In contrast, "background template" is used in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular gene sequences. It is contemplated that any probe used in the present invention will be labelled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the term "target," when used in reference to the polymerase chain reaction, refers to the region of nucleic acid bounded by the primers used for polymerase chain reaction. Thus, the "target" is sought to be sorted out from other nucleic acid sequences. A "segment" is defined as a region of nucleic acid within the target sequence.

As used herein, the term "polymerase chain reaction" ("PCR") refers to the method of K. B. Mullis U.S. Pat. Nos. 4,683,195, 4,683,202, and 4,965,188, hereby incorporated by reference, that describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing, and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications.

As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "amplification reagents" refers to those reagents (deoxyribonucleotide triphosphates, buffer, etc.), needed for amplification except for primers, nucleic acid template, and the amplification enzyme. Typically, amplification reagents along with other reaction components are placed and contained in a reaction vessel (test tube, microwell, etc.).

As used herein, the term "reverse-transcriptase" or "RT-PCR" refers to a type of PCR where the starting material is mRNA. The starting mRNA is enzymatically converted to complementary DNA or "cDNA" using a reverse transcriptase enzyme. The cDNA is then used as a "template" for a "PCR" reaction.

As used herein, the terms "restriction endonucleases" and "restriction enzymes" refer to bacterial enzymes, each of which cut double-stranded DNA at or near a specific nucleotide sequence.

As used herein, the term "recombinant DNA molecule" as used herein refers to a DNA molecule that is comprised of segments of DNA joined together by means of molecular biological techniques.

As used herein, the term "antisense" is used in reference to RNA sequences that are complementary to a specific RNA sequence (e.g., mRNA). Included within this definition are antisense RNA ("asRNA") molecules involved in gene regulation by bacteria. Antisense RNA may be produced by any method, including synthesis by splicing the gene(s) of interest in a reverse orientation to a viral promoter that permits the synthesis of a coding strand. Once introduced into an embryo, this transcribed strand combines with natural mRNA produced by the embryo to form duplexes. These duplexes then block either the further transcription of the mRNA or its translation. In this manner, mutant phenotypes may be generated. The term "antisense strand" is used in reference to a nucleic acid strand that is complementary to the "sense" strand. The designation (−) (i.e., "negative") is sometimes used in reference to the antisense strand, with the designation (+) sometimes used in reference to the sense (i.e., "positive") strand.

The term "isolated" when used in relation to a nucleic acid, as in "an isolated oligonucleotide" or "isolated polynucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids are nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a rabbit PON3 protein includes, by way of example, such nucleic acid in cells ordinarily expressing a PON3 protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may single-stranded), but may contain both the sense and anti-sense strands (i.e., the oligonucleotide or polynucleotide may be double-stranded).

As used herein, a "portion of a chromosome" refers to a discrete section of the chromosome. Chromosomes are divided into sites or sections by cytogeneticists as follows: the short (relative to the centromere) arm of a chromosome is termed the "p" arm; the long arm is termed the "q" arm. Each arm is then divided into 2 regions termed region 1 and region 2 (region 1 is closest to the centromere). Each region is further divided into bands. The bands may be further divided into sub-bands. For example, the 11p15.5 portion of human chromosome 11 is the portion located on chromosome 11 (11) on the short arm (p) in the first region (1) in the 5th band (5) in sub-band 5 (0.5). A portion of a chromosome may be "altered;" for instance the entire portion may be absent due to a deletion or may be rearranged (e.g., inversions, translocations, expanded or contracted due to changes in repeat regions). In the case of a deletion, an attempt to hybridize (i.e., specifically bind) a probe homologous to a particular portion of a chromosome could result in a negative result (i.e., the probe could not bind to the sample containing genetic material suspected of containing the missing portion of the chromosome). Thus, hybridization of a probe homologous to a particular portion of a chromosome may be used to detect alterations in a portion of a chromosome.

The term "sequences associated with a chromosome" means preparations of chromosomes (e.g., spreads of metaphase chromosomes), nucleic acid extracted from a sample containing chromosomal DNA (e.g., preparations of genomic DNA); the RNA that is produced by transcription of genes located on a chromosome (e.g., hnRNA and mRNA), and cDNA copies of the RNA transcribed from the DNA located on a chromosome. Sequences associated with a chromosome may be detected by numerous techniques including probing of Southern and Northern blots and in situ hybridization to RNA, DNA, or metaphase chromosomes with probes containing sequences homologous to the nucleic acids in the above listed preparations.

As used herein the term "coding region" when used in reference to a structural gene refers to the nucleotide sequences that encode the amino acids found in the nascent polypeptide as a result of translation of a mRNA molecule. The coding region is bounded, in eukaryotes, on the 5' side by the nucleotide triplet "ATG" that encodes the initiator methionine and on the 3' side by one of the three triplets which specify stop codons (i.e., TAA, TAG, TGA).

As used herein, the term "purified" or "to purify" refers to the removal of contaminants from a sample. For example, PON3 polypeptides are purified by removal of contaminating non-PON3 proteins The removal of non-PON3 proteins results in an increase in the percent of PON3 polypeptide in the sample. In another example, recombinant PON3 polypeptides are expressed in bacterial or mammalian host cells and the polypeptides are purified by the removal of host cell proteins; the percent of recombinant PON3 polypeptides is thereby increased in the sample.

The term "recombinant DNA molecule" as used herein refers to a DNA molecule that is comprised of segments of DNA joined together by means of molecular biological techniques.

As used herein the term "portion" when in reference to a nucleotide sequence (as in "a portion of a given nucleotide sequence") refers to fragments of that sequence. The fragments may range in size from four nucleotides to the entire nucleotide sequence minus one nucleotide (10 nucleotides, 20, 30, 40, 50, 100, 200, etc.).

The term "recombinant protein" or "recombinant polypeptide" as used herein refers to a protein molecule that is expressed from a recombinant DNA molecule. For example, "rPON3" refers to recombinant PON3.

The term "native protein" as used herein to indicate that a protein does not contain amino acid residues encoded by vector sequences; that is the native protein contains only those amino acids found in the protein as it occurs in nature. A native protein may be produced by recombinant means or may be isolated from a naturally occurring source.

As used herein the term "biologically active polypeptide" (e.g., biologically active PON3 polypeptide) refers to any polypeptide (e.g., PON3) which maintains a desired biological activity (e.g., hydrolysis of a given lactone).

As used herein the term "portion" when in reference to a protein (as in "a portion of a given protein") refers to fragments of that protein. The fragments may range in size from four amino acid residues to the entire amino acid sequence minus one amino acid (10 amino acids, 20, 30, 40, 50, 100, 200, etc.).

The term "Southern blot," refers to the analysis of DNA on agarose or acrylamide gels to fractionate the DNA according to size followed by transfer of the DNA from the gel to a solid support, such as nitrocellulose or a nylon membrane. The immobilized DNA is then probed with a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (Sambrook et al., Molecular Cloning: A Laboratory Manual, Cold Spring Harbor Press, NY, pp 9.31–9.58 [1989]).

The term "Northern blot," as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (Sambrook, et al., supra, pp 7.39–7.52 [1989]).

The term "Western blot" refers to the analysis of protein (s) (or polypeptides) immobilized onto a support such as nitrocellulose or a membrane. The proteins are run on acrylamide gels to separate the proteins, followed by transfer of the protein from the gel to a solid support, such as nitrocellulose or a nylon membrane. The immobilized proteins are then exposed to antibodies with reactivity against an antigen of interest. The binding of the antibodies may be detected by various methods, including the use of radiolabelled antibodies.

The term "antigenic determinant" as used herein refers to that portion of an antigen that makes contact with a particular antibody (i.e., an epitope). When a protein or fragment of a protein is used to immunize a host animal, numerous regions of the protein may induce the production of antibodies that bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody.

The term "transgene" as used herein refers to a foreign gene that is placed into an organism by introducing the foreign gene into newly fertilized eggs or early embryos. The term "foreign gene" refers to any nucleic acid (e.g., gene sequence) that is introduced into the genome of an animal by experimental manipulations and may include gene sequences found in that animal so long as the introduced gene does not reside in the same location as does the naturally-occurring gene.

As used herein, the term "vector" is used in reference to nucleic acid molecules that transfer DNA segment(s) from one cell to another. The term "vehicle" is sometimes used interchangeably with "vector."

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The terms "overexpression" and "overexpressing" and grammatical equivalents, refers to the transcription and translation of a gene. Such transcription and translation may be in vivo or in vitro.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" refers to the introduction and integration of foreign DNA into the genome of the transfected cell. The term "stable transfectant" refers to a cell that has stably integrated foreign DNA into the genomic DNA.

The term "transient transfection" or "transiently transfected" refers to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of Graham and van der Eb (Graham and van der Eb, Virol., 52:456 [1973]), has been modified by several groups to optimize conditions for particular types of cells. The art is well aware of these numerous modifications.

A "composition comprising a given polynucleotide sequence" as used herein refers broadly to any composition containing the given polynucleotide sequence. The composition may comprise an aqueous solution. Compositions comprising polynucleotide sequences encoding Pon3 (e.g., SEQ ID NO:7) or fragments thereof may be employed as hybridization probes. In this case, the Pon-3-encoding polynucleotide sequences are typically employed in an aqueous solution containing salts (e.g., NaCl), detergents (e.g., SDS), and other components (e.g., Denhardt's solution, dry milk, salmon sperm DNA, etc.).

The term "test compound" refers to any chemical entity, pharmaceutical, drug, and the like that can be or might be used to treat or prevent a disease, illness, sickness, or disorder of bodily function, or otherwise alter the physiological or cellular status of a sample. Test compounds comprise both known and potential therapeutic compounds. A test compound can be determined to be therapeutic by screening using the screening methods of the present invention. A "known therapeutic compound" refers to a therapeutic compound that has been shown (e.g., through animal trials or prior experience with administration to humans) to be effective in such treatment or prevention. In other words, a known therapeutic compound is not limited to a compound efficacious in the treatment of pathological conditions such as sepsis, oxidative damage, or chemical toxicity. A "candidate therapeutic compound" refers to a compound suspected of having therapeutic activity that may be tested to determine if it has therapeutic benefits (e.g., either directly by observing therapeutic benefits in a subject or through a surrogate indicator). Candidate therapeutic compounds include compounds suspected of having therapeutic benefits based on chemical structure as well as members of compound libraries (e.g., libraries of compounds containing known or unknown compounds or structures). Candidate therapeutic compounds can be tested for therapeutic properties using any suitable method (e.g., screening assays) including, but not limited to, the screening methods described herein.

As used herein, the term "sample" is used in its broadest sense. In one sense it can refer to a tissue sample. In another sense, it is meant to include a specimen or culture obtained from any source, as well as biological. Biological samples may be obtained from animals (including humans) and encompass fluids, solids, tissues, and gases. Biological samples include, but are not limited to blood products, such as plasma, serum and the like. These examples are not to be construed as limiting the sample types applicable to the present invention.

DETAILED DESCRIPTION OF THE INVENTION

I. PON Genes.

The present invention provides compositions comprising nucleotide sequences of the rabbit Pon3 gene and variants, homologs, mutants, chimeras, and fusions thereof.

A. Known PON Genes

A number or paraoxonase gene family members have been isolated from a variety of organisms. Table 1 shows the Genbank accession numbers and publication information of known PON sequences.

TABLE 1

PON Genes

| Accession Number | PON Gene | Organism | Publication |
|---|---|---|---|
| M63011 | 1 | Rabbit | Hassett et al., Biochemistry, 30: 10141 [1991] |
| S56546 | 1 | Human | Adkins et al., Am. J. Hum. Gent., 52:598 [1993] |
| S64696 | 1B | Human | La Du et al., Chem. Biol. Interact., 87:25 [1993] |
| S64615 | 1 | Human | Furlong et al., Chem. Biol. Interact., 87:35 [1993] |
| S64616 | 1 | Rabbit | Furlong et al., Chem. Biol. Interact., 87:35 [1993] |
| M63012 | 1 | Human | Hassett et al., Biochemistry, 30: 10141 [1991] |
| U32684 | 1 | Mouse | Shih et al., J. Clin. Invest., 97:1630 [1996] |
| L40488 | 1 | Mouse | Sorenson et al., PNAS, 92:7187 [1995] |
| L48515 | 2 | Dog | Primo-Parmo et al., Genomics, 33:498 [1996] |
| L48513 | 2 | Human | Primo-Parmo et al., Genomics, 33:498 [1996] |
| L48514 | 2 | Mouse | Primo-Parmo et al., Genomics, 33:498 [1996] |
| L76193 | 3 | Mouse | Primo-Panno et al., Genomics, 33:498 [1996] |
| L47573 | 2 | Chicken | Primo-Parmo et al., Genomics, 33:498 [1996] |
| L47572 | 2 | Turkey | Primo-Parmo et al., Genomics, 33:498 [1996] |
| U72636 | 1 | Mouse | Li W-F et al., Unpublished [1996] |
| U55885 | 1 | Human | Hassett et al., Biochemistry, 30: 10141 [1991]; Clendenning et al., Genomics, 35:586 [1996] |
| U55877 | 1 | Human | Clendenning et at., Genomics, 35:586 [1996] |
| U94856 | 1 | Rat | Leviev, et al., Unpublished |
| AF003141 | | C. Elegans | Wilson et al., Nature, 368:32 [1994] |
| 142585 | | Human | Hudson et al., U.S. Pat. No. 5,629,193 |
| AF001601 | 2 | Human | Mochizuki et al., Gene, 213:149 [1998] |
| AF001602 | 2 | Human | Mochizuki et al., Gene, 213:149 [1998] |
| AR022313 | | Human | Hudson et al., U.S. Pat. No. 5,792,639 |
| NM_00035 (AF001601) | 2 | Human | Mochizuki et al., Gene, 213:149 [1998] |

TABLE 1-continued

PON Genes

| Accession Number | PON Gene | Organism | Publication |
|---|---|---|---|
| NM_000446 (S64615) | 1 | Human | Furlong et al., Chem. Biol. Interact., 87:35 [1993] |
| AC005021 | 2 and 3 | Human | Waterston et al., Unpublished BAC Clone |
| MN_008896 (L48514.1) | 2 | Mouse | Primo-Parmo et al., Genomics, 33:498 [1996] |

B. Cloning of the Rabbit Pon3 Gene

In some embodiments of the present invention, the rabbit Pon3 nucleotide sequence is provided. Rabbit Pon3 was cloned as described in Example 1 using RT-PCR. In this illustrative example, the human Pon3 sequence was used as a model for designing primers used in the cloning of the rabbit Pon3 cDNA. A 1191 bp cDNA with 1065 bp open reading frame (SEQ ID No:7), encoding a protein of 39.5 kDa was cloned.

The nucleotide and deduced amino acid sequence (SEQ ID NO: 8) are shown in FIG. 1. The rabbit PON3 nucleic acid sequence is 86% identical to the previously reported human PON3 sequence and 79% identical to the mouse PON3 (Primo-Parmo et al., Genomics, 33: 498 [1996]). The nucleic acid sequence is 58% identical to both the known rabbit PON1 and PON2 sequences. The rabbit PON3 nucleotide sequence is 58% identical at the nucleotide level to the amino acid sequence reported by Human Genome Sciences (U.S. Pat. No. 5,792,639).

A comparison of the deduced polypeptide sequence of PON3 and other PON genes is shown in FIG. 2. The predicted polypeptide is 95% identical to the amino acid sequence of microsomal paraoxonase (MsPON) isolated from rabbit liver (the amino acid sequence of rabbit msPON was described by Ozols; Ozols, Biochem J., 338:265 [1999]). The sequence described by Ozols contains an amino acid sequence similar to the deduced rabbit PON3 sequence except for 17 residues (5% difference). The predicted amino acid sequence of rabbit PON3 is 82% identical to the deduced human PON3 protein and 78% identical to mouse PON3. The predicted amino acid sequence of rabbit PON3 is 58% and 64% identical to the deduced rabbit PON1 and PON2 proteins, respectively. The rabbit PON3 amino acid sequence is 59% identical to the amino acid sequence reported by Human Genome Sciences (U.S. Pat. No. 5,792, 639).

In the mature protein, as previously known for the rabbit and human PON1 (Hassett et al., Biochemistry, 30:10141–10149 [1991]), only the first methionine is processed and the remainder of the leader sequence is retained.

C. Generation of Mutant PON3

In some embodiments, the present invention provides polynucleotide sequences comprising mutant Pon3. Mutants include, but are not limited to, SEQ ID NOs:9, 11, 13, 15, 17). Mutants of Pon3 can be generated by any suitable method. In some embodiments, mutants are generated by site-directed mutagenesis.

In one illustrative example (Example 6) of the present invention, mutants of Pon3 corresponding to SEQ ID NOs:9, 11, 13, 15, 17 are generated by site-directed mutagenesis. In Example 6, two primers (one in the forward orientation and one in the reverse) with the desired mutation incorporated into their sequence were used in separate PCR reactions using primers in the 5'- or 3'-untranslated region. The resulting fragments were purified and combined. A PCR reaction using the two external primers was then carried out on the mixture. The generated product is a full-length Pon3 nucleotide sequence containing the desired mutation. The PCR product was cloned into the pcDNA3.1 vector and sequenced. In this example, four site-directed single amino acid change mutations were generated (N169D; K243H; L281W; and D324N). In some embodiments, truncation mutants of PON3 are provided. In one illustrative example (Example 6), a truncation mutant (E46K; SEQ ID NO:17) was generated.

D. Additional PON3 Genes

The present invention provides nucleic acids corresponding to Pon3 genes from rabbit (SEQ ID NO:7). For example, some embodiments of the present invention provide polynucleotide sequences that are capable of hybridizing to SEQ ID NO: 7 under conditions of medium to high stringency as long as the polynucleotide sequence capable of hybridizing encodes a protein that retains a desired biological activity of the naturally occurring PON3 (e.g., lactonase activity). In preferred embodiments, hybridization conditions are based on the melting temperature ($T_m$) of the nucleic acid binding complex and confer a defined "stringency" as explained above (See e.g., Wahl, et al., Meth. Enzymol., 152:399–407 [1987], incorporated herein by reference).

In other embodiments of the present invention, alleles of PON3 are provided. In preferred embodiments, alleles result from a mutation, (i.e., a change in the nucleic acid sequence) and generally produce altered mRNAs or polypeptides whose structure or function may or may not be altered. Any given gene may have none, one or many allelic forms. Common mutational changes that give rise to alleles are generally ascribed to deletions, additions or substitutions of nucleic acids. Each of these types of changes may occur alone, or in combination with the others, and at the rate of one or more times in a given sequence.

In still other embodiments of the present invention, the nucleotide sequences of the present invention may be engineered in order to alter an PON3 coding sequence for a variety of reasons, including but not limited to, alterations that modify the cloning, processing and/or expression of the gene product. For example, mutations may be introduced using techniques that are well known in the art (e.g., site-directed mutagenesis to insert new restriction sites, to alter glycosylation patterns, to change codon preference, etc.).

In some embodiments of the present invention, the polynucleotide sequence of PON3 is extended utilizing the nucleotide sequences (e.g., SEQ ID NO:7) in various methods known in the art to detect upstream sequences such as promoters and regulatory elements. For example, it is contemplated that restriction-site polymerase chain reaction (PCR) finds use in the present invention. This is a direct method that uses universal primers to retrieve unknown sequence adjacent to a known locus (Gobinda et al., PCR Methods Applic., 2:318–22 [1993]). First, genomic DNA is amplified in the presence of primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

In another embodiment, inverse PCR is used to amplify or extend sequences using divergent primers based on a known region (Triglia et al., Nucleic Acids Res., 16:8186 [1988]). The primers may be designed using Oligo 4.0 (National Biosciences Inc, Plymouth Minn.), or another appropriate program, to be, for example, 22–30 nucleotides in length, to have a GC content of 50% or more, and to anneal to the target sequence at temperatures about 68–72° C. The method uses several restriction enzymes to generate a suitable fragment in the known region of a gene. The fragment is then circularized by intramolecular ligation and used as a PCR template. In yet another embodiment of the present invention, capture PCR (Lagerstrom et al., PCR Methods Applic., 1:111–19 [1991]) is used. This is a method for PCR amplification of DNA fragments adjacent to a known sequence in human and yeast artificial chromosome (YAC) DNA. Capture PCR also requires multiple restriction enzyme digestions and ligations to place an engineered double-stranded sequence into an unknown portion of the DNA molecule before PCR. In still other embodiments, walking PCR is utilized. Walking PCR is a method for targeted gene walking that permits retrieval of unknown sequence (Parker et al., Nucleic Acids Res., 19:3055–60 [1991]). The PROMOTERFINDER kit (Clontech) uses PCR, nested primers and special libraries to "walk in" genomic DNA. This process avoids the need to screen libraries and is useful in finding intron/exon junctions.

Preferred libraries for screening for full length cDNAs include libraries that have been size-selected to include larger cDNAs. Also, random primed libraries are preferred, in that they contain more sequences that contain the 5' and upstream gene regions. A randomly primed library may be particularly useful in cases where an oligo d(T) library does not yield full-length cDNA. Genomic Libraries are useful for obtaining introns and extending 5' sequence.

E. Expression of Cloned PON3

In some embodiments, the present invention provides Pon3 polynucleotide sequences that encode PON3 polypeptide sequences. Other embodiments of the present invention provide mutants, fragments, fusion proteins or functional equivalents of these PON3 proteins. In still other embodiment of the present invention, nucleic acid sequences corresponding to these various PON3 homologs and mutants may be used to generate recombinant DNA molecules that direct the expression of the PON3 homologs and mutants in appropriate host cells. In some embodiments of the present invention, the polypeptide may be a naturally purified product, while in other embodiments it may be a product of chemical synthetic procedures, and in still other embodiments it may be produced by recombinant techniques using a prokaryotic or eukaryotic host (e.g., by bacterial, yeast, higher plant, insect and mammalian cells in culture). In some embodiments, depending upon the host employed in a recombinant production procedure, the polypeptide of the present invention may be glycosylated or may be nonglycosylated. In other embodiments, the polypeptides of the invention may also include an initial methionine amino acid residue.

In one embodiment of the present invention, due to the inherent degeneracy of the genetic code, DNA sequences other than the polynucleotide sequences of SEQ ID NO:7, that encode substantially the same or a functionally equivalent amino acid sequence, may be used to clone and express PON3. In general, such polynucleotide sequences hybridize to SEQ ID NO:7 under conditions of high to medium stringency as described above. As will be understood by those of skill in the art, it may be advantageous to produce PON3-encoding nucleotide sequences possessing non-naturally occurring codons. Therefore, in some preferred embodiments, codons preferred by a particular prokaryotic or eukaryotic host (Murray et al., Nucl. Acids Res., 17 [1989]) can be selected, for example, to increase the rate of PON3 expression or to produce recombinant RNA transcripts having desirable properties, such as a longer half-life, than transcripts produced from naturally occurring sequence.

1. Vectors for Production of PON3

The polynucleotides of the present invention may be employed for producing polypeptides by recombinant techniques. Thus, for example, the polynucleotide may be included in any one of a variety of expression vectors for expressing a polypeptide. In some embodiments of the present invention, vectors include, but are not limited to, chromosomal, nonchromosomal and synthetic DNA sequences (e.g., derivatives of SV40, bacterial plasmids, phage DNA; baculovirus, yeast plasmids, vectors derived from combinations of plasmids and phage DNA, and viral DNA such as vaccinia, adenovirus, fowl pox virus, and pseudorabies). It is contemplated that any vector may be used as long as it is. replicable and viable in the host.

In particular, some embodiments of the present invention provide recombinant constructs comprising one or more of the sequences as broadly described above (e.g., SEQ ID NOs: 7, 9, 11, 13, 15, 17). In some embodiments of the present invention, the constructs comprise a vector, such as a plasmid or viral vector, into which a sequence of the invention has been inserted, in a forward or reverse orientation. In preferred embodiments of the present invention, the appropriate DNA sequence is inserted into the vector using any of a variety of procedures. In general, the DNA sequence is inserted into an appropriate restriction endonuclease site(s) by procedures known in the art.

Large numbers of suitable vectors are known to those of skill in the art, and are commercially available. Such vectors include, but are not limited to, the following vectors: 1) Bacterial—pQE70, pQE60, pQE-9 (Qiagen), pBS, pD10, phagescript, psiX174, pbluescript SK, pBSKS, pNH8A, pNH16a, pNH18A, pNH46A (Stratagene); ptrc99a, pKK223-3, pKK233-3, pDR540, pRIT5 (Pharmacia); and 2) Eukaryotic—pWLNEO, pSV2CAT, pOG44, PXT1, pSG (Stratagene) pSVK3, pBPV, pMSG, and pSVL (Pharmacia). Any other plasmid or vector may be used as long as they are replicable and viable in the host. In some preferred embodiments of the present invention, mammalian expression vectors comprise an origin of replication, a suitable promoter and enhancer, and also any necessary ribosome binding sites, polyadenylation sites, splice donor and acceptor sites, transcriptional termination sequences, and 5' flanking nontranscribed sequences. In other embodiments, DNA sequences derived from the SV40 splice, and polyadenylation sites may be used to provide the required nontranscribed genetic elements.

In certain embodiments of the present invention, the DNA sequence in the expression vector is operatively linked to an appropriate expression control sequence(s) (promoter) to direct mRNA synthesis. Promoters useful in the present invention include, but are not limited to, the LTR or SV40 promoter, the *E. coli* lac or trp, the phage lambda $P_L$ and $P_R$, T3 and T7 promoters, and the cytomegalovirus (CMV) immediate early, herpes simplex virus (HSV) thymidine kinase, and mouse metallothionein-I promoters and other promoters known to control expression of gene in prokaryotic or eukaryotic cells or their viruses. In other embodiments of the present invention, recombinant expression vectors include origins of replication and selectable markers permitting transformation of the host cell (e.g., dihydrofolate reductase or neomycin resistance for eukaryotic cell culture, or tetracycline or ampicillin resistance in *E. coli*).

In some embodiments of the present invention, transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Enhancers useful in the present invention include, but are not limited to, the SV40 enhancer on the late side of the replication origin bp 100 to 270, a cytomegalovirus early promoter enhancer, the polyoma enhancer on the late side of the replication origin, and adenovirus enhancers.

In other embodiments, the expression vector also contains a ribosome binding site for translation initiation and a transcription terminator. In still other embodiments of the present invention, the vector may also include appropriate sequences for amplifying expression.

In one illustrative example (Example 6), PON3 and PON3 mutants are cloned into the mammalian vector pcDNA3.1 (Invitrogen, Carlsbad, Calif.).

In another illustrative example (Example 7), PON3 is cloned into the bacterial expression vector pET24d+ (Novagen). The pET24d+ vector contains a T7 promoter, a selectable marker (the gene for kanamyacin resistance), an affinity tag (His Tag), and a multiple cloning site.

2. Host Cells for Production of PON3

In a further embodiment, the present invention provides host cells containing the above-described constructs. In some embodiments of the present invention, the host cell is a higher eukaryotic cell (e.g., a mammalian or insect cell). In other embodiments of the present invention, the host cell is a lower eukaryotic cell (e.g., a yeast cell). In still other embodiments of the present invention, the host cell can be a prokaryotic cell (e.g., a bacterial cell). Specific examples of host cells include, but are not limited to, *Escherichia coli, Salmonella typhimurium, Bacillus subtilis*, and various species within the genera *Pseudomonas, Streptomyces,* and *Staphylococcus*, as well as *Saccharomycees cerivisiae, Schizosaccharomycees pombe, Drosophila* S2 cells, *Spodoptera* Sf9 cells, Chinese hamster ovary (CHO) cells, COS-7 lines of monkey kidney fibroblasts, (Gluzman, Cell 23:175 [1981]), 293T, C127, 3T3, HeLa and BHK cell lines.

The constructs in host cells can be used in a conventional manner to produce the gene product encoded by the recombinant sequence. In some embodiments, introduction of the construct into the host cell can be accomplished by calcium phosphate transfection, DEAE-Dextran mediated transfection, or electroporation (See e.g., Davis et al., Basic Methods in Molecular Biology, [1986]). Alternatively, in some embodiments of the present invention, the polypeptides of the invention can be synthetically produced by conventional peptide synthesizers.

Proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N.Y., (1989).

In some embodiments of the present invention, following transformation of a suitable host strain and growth of the host strain to an appropriate cell density, the selected promoter is induced by appropriate means (e.g., temperature shift or chemical induction) and cells are cultured for an additional period. In other embodiments of the present invention, cells are typically harvested by centrifugation, disrupted by physical or chemical means, and the resulting crude extract retained for further purification. In still other embodiments of the present invention, microbial cells employed in expression of proteins can be disrupted by any convenient method, including freeze-thaw cycling, sonication, mechanical disruption, or use of cell lysing agents.

In one illustrative embodiment of the present invention, PON3 genes cloned into the mammalian expression vector pcDNA3.1 and expressed in human 293T cells. In another illustrative example, the PON3 gene was cloned into the bacterial expression vector pET24d+ and expressed in *E. coli* BL21(DE3) cells.

3. Purification of PON3

The present invention also provides methods for recovering and purifying PON3 from recombinant cell cultures including, but not limited to, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. In some embodiments of the present invention, the protocol of Example 3 is used to purify recombinant PON3. In this illustrative example (Example 3), PON3 is purified from rabbit serum using a series of chromatography steps.

The present invention further provides polynucleotides having the coding sequence (e.g., SEQ ID NO: 7) fused in frame to a marker sequence that allows for purification of the polypeptide of the present invention. A non-limiting example of a marker sequence is a hexahistidine tag that may be supplied by a vector, preferably a pQE-9 vector, that provides for purification of the polypeptide fused to the marker in the case of a bacterial host, or, for example, the marker sequence may be a hemagglutinin (HA) tag when a mammalian host (e.g., 293T cells) is used. The HA tag corresponds to an epitope derived from the influenza hemagglutinin protein (Wilson et al., Cell, 37:767 [1984]).

4. Truncation Mutants of PON3

In addition, the present invention provides fragments of PON3 (i.e., truncation mutants). In preferred embodiments, the PON3 fragment is biologically active. In some embodiments of the present invention, when expression of a portion of the PON3 protein is desired, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from *E. coli* (Ben-Bassat et al., J. Bacteriol., 169:751–757 [1987]) and *Salmonella typhimurium* and its in vitro activity has been demonstrated on recombinant proteins (Miller et al., Proc. Natl. Acad. Sci. USA, 84:2718–1722 [1990]). Therefore, removal of an N-terminal methionine, if desired, can be achieved either in vivo by expressing such recombinant polypeptides in a host that produces MAP (e.g., *E. coli* or CM89 or *S. cerevisiae*), or in vitro by use of purified MAP.

In one illustrative Example (Example 6), a truncation mutant of PON3 (SEQ ID NO: 17) was engineered using site-directed mutagenesis. The mutant was cloned into the pcDNA3.1 mammalian expression vector and expressed in human 293T cells. The present invention is not limited to the truncation mutant of SEQ ID NO: 17. Indeed, other truncation mutants are contemplated by the present invention.

5. Humanized Rabbit PON3 Peptides

Still other embodiments of the present invention provide humanized mutant forms of rabbit PON3. It is possible to humanize the structure of a peptide having an activity of PON3 for such purposes as enhancing therapeutic or prophylactic efficacy, and to increase the biocompatability of these peptides in humans. A humanized rabbit PON3 peptide is produced, for example, by substituting any of the rabbit PON3 functional domains into the human PON3 polypeptide or by making the appropriate amino acid substitutions as detailed below.

SEQ ID NO:27 represents a functional domain of rabbit PON3 that is defined by amino acids 51–87 of SEQ ID NO:8. SEQ ID NO:27 may be substituted for amino acids 51–87 of human PON3 in order to construct a humanized rabbit PON3 peptide. Alternatively, the same humanized rabbit PON3 peptide may be constructed by making a serine (S) to alanine (A) substitution at position 63 of human PON3 and a glutamic acid (E) to glycine (G) substitution as position 68 of human PON3.

SEQ ID NO:28 represents a functional domain of rabbit PON3 that is defined by amino acids 125–187 of SEQ ID NO:8. SEQ ID NO:28 may be substituted for amino acids 125–187 of human PON3 in order to construct a humanized rabbit PON3 peptide. Alternatively, the same humanized rabbit PON3 peptide may be constructed by making a tyrosine (Y) to histidine (H) substitution at position 154 of human PON3 and a aspartic acid (D) to asparagine (N) substitution at position 168.

SEQ ID NO:29 represents a functional domain of rabbit PON3 that is defined by amino acids 204–228 of SEQ ID NO:8. SEQ ID NO:29 may be substituted for amino acids 204–228 of human PON3 in order to construct a humanized rabbit PON3 peptide. Alternatively, the same humanized rabbit PON3 peptide may be constructed by making an arginine (R) to lysine (K) substitution at position 210 of human PON3 and a cystein (C) to serine (S) substitution at position 220 of human PON3.

SEQ ID NO:30 represents a functional domain of rabbit PON3 that is defined by amino acids 272–316 of SEQ ID NO:8. SEQ ID NO:30 may be substituted for amino acids 272–316 of human PON3 in order to construct a humanized rabbit PON3 peptide. Alternatively, the same humanized rabbit PON3 peptide may be constructed by making a proline (P) to glycine (G) substitution at position 287 of human PON3.

The above functional domains (i.e., SEQ ID NOS:27–30) may be substituted into human PON3 either individually or in any combination. For example, a humanized rabbit PON3 peptide may be constructed by substituting SEQ ID NOS:27 and 28 into human PON3 at the appropriate locations. Another example of a humanize rabbit PON3 peptide is constructed by substituting SEQ ID NOS:27, 28 and 30 into human PON3 at the appropriate location. Additionally, various humanized rabbit PON3 peptides may be constructed by any combination of the single amino acid substitutions detailed above.

Rabbit PON3 has additional regions that may be substituted into corresponding regions of human PON3 in order to construct various humanized rabbit PON3 peptides. Examples of these additional regions include, but are not limited to, four regions of SEQ ID NO:8 as follows; amino acids 1–50, amino acids 88–124, amino acids 188–203, and amino acids 229–271. These four domains may be substituted for the corresponding regions of human PON3 (e.g., human PON3 amino acids 1–50, 88–124, 188–203, and 229–271 respectively) either individually or any combination to form humanized rabbit PON3 peptides. Additionally, any combination of these four regions and the functional domains represented by SEQ ID NOS: 27–30, may be used to make substitutions in human PON3 in order to construct a humanized rabbit PON3 peptide. Humanized rabbit PON3 peptides be constructed by making the appropriate changes to the nucleic acid sequence encoding the peptide, and expressing the nucleic acid in a host or through peptide synthesis or other suitable methods.

6. Fusion Proteins Containing PON3

The present invention also provides fusion proteins incorporating all or part of rabbit PON3. In some embodiments, the fusion proteins have a rabbit PON3 functional domain (e.g. SEQ ID NOS:27–30) with a fusion partner. Accordingly, in some embodiments of the present invention, the coding sequences for the polypeptide (e.g. a rabbit PON3 functional domain) is incorporated as a part of a fusion gene including a nucleotide sequence encoding a different polypeptide. In some embodiments of the present invention, chimeric constructs coding for fusion proteins containing a portion of PON3 (e.g., SEQ ID NOS:27–30) and a portion of another PON gene (See e.g., Table 1, for a list of known PON genes). In some embodiments, the fusion proteins contains a portion of a human PON gene, for example, including but not limited to human PON1, PON2, or PON3. In some embodiments, the fusion proteins have biological activity similar to the wild type PON3 (e.g., have at least one desired biological activity of PON3). In other embodiments, the fusion protein have altered biological activity. Such polypeptides find use in pharmaceutical embodiments discussed below.

In addition to utilizing fusion proteins to alter biological activity, it is widely appreciated that fusion proteins can also facilitate the expression of proteins, such as the rabbit PON3 protein of the present invention. Accordingly, in some embodiments of the present invention, PON3 is generated as a glutathione-S-transferase (i.e., GST fusion protein). It is contemplated that such GST fusion proteins enables easy purification of PON3, such as by the use of glutathione-derivatized matrices (See e.g., Ausabel et al. (eds.), Current Protocols in Molecular Biology, John Wiley & Sons, NY [1991]). In another embodiment of the present invention, a fusion gene coding for a purification leader sequence, such as a poly-(His)/enterokinase cleavage site sequence at the N-terminus of the desired portion of PON3 allows purification of the expressed PON3 fusion protein by affinity chromatography using a $Ni^{2+}$ metal resin. In still another embodiment of the present invention, the purification leader sequence is then subsequently removed by treatment with enterokinase (See e.g., Hochuli et al., J. Chromatogr., 411:177 [1987]; and Janknecht et al., Proc. Natl. Acad. Sci. USA, 88:8972).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment of the present invention, the fusion gene can be synthesized by conventional techniques including automated DNA synthesizers. Alternatively, in other embodiments of the present invention, PCR amplification of gene fragments is carried out using anchor primers that give rise to complementary overhangs between two consecutive gene fragments that can subsequently be annealed to generate a chimeric gene sequence (See e.g., Current Protocols in Molecular Biology, supra).

7. Variants of PON3

Still other embodiments of the present invention provide mutant or variant forms of PON3 (i.e., muteins). It is possible to modify the structure of a peptide having an activity of PON3 for such purposes as enhancing therapeutic or prophylactic efficacy, or stability (e.g., ex vivo shelf life, and/or resistance to proteolytic degradation in vivo). Such modified peptides provide additional peptides having a desired activity of the subject PON3 proteins as defined herein. A modified peptide can be produced in which the amino acid sequence has been altered, such as by amino acid substitution, deletion, or addition.

Moreover, as described above, variant forms (e.g., mutants) of the subject PON3 proteins are also contemplated as finding use in the present invention. For example, it is contemplated that an isolated replacement of a leucine with an isoleucine or valine, an aspartate with a glutamate, a threonine with a serine, or a similar replacement of an amino acid with a structurally related amino acid (i.e., conservative mutations) will not have a major effect on the biological activity of the resulting molecule. Accordingly, some embodiments of the present invention provide variants of PON3 containing conservative replacements. Conservative replacements are those that take place within a family of amino acids that are related in their side chains. Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. In similar fashion, the amino acid repertoire can be grouped as (1) acidic (aspartate, glutamate); (2) basic (lysine, arginine histidine), (3) aliphatic (glycine, alanine, valine, leucine, isoleucine, serine, threonine), with serine and threonine optionally be grouped separately as aliphatic-hydroxyl; (4) aromatic (phenylalanine, tyrosine, tryptophan); (5) amide (asparagine, glutamine); and (6) sulfur -containing (cysteine and methionine) (See e.g., Stryer (ed.), *Biochemistry*, 2nd ed, WH Freeman and Co. [1981]). Whether a change in the amino acid sequence of a peptide results in a functional homolog can be readily determined by assessing the ability of the variant peptide to produce a response in cells in a fashion similar to the wild-type protein. Peptides in which more than one replacement has taken place can readily be tested in the same manner. The present invention further contemplates a method of generating sets of combinatorial mutants of the present PON3 proteins, as well as truncation mutants, and is especially useful for identifying potential variant sequences (i.e., homologs) that possess the biological activity of PON3 (e.g., hydrolysis of particular lactones). In addition, screening such combinatorial libraries is used to generate, for example, novel PON3 homologs that possess novel biological activities all together.

Therefore, in some embodiments of the present invention, PON3 homologs are engineered by the present method to provide more efficient hydrolysis of lactones (See e.g., Example 2 for methods of assaying lactone hydrolysis). In other embodiments of the present invention, combinatorially-derived homologs are generated which have a selective affinity for certain lactones relative to a naturally occurring PON3 (See e.g., Example 2 for methods of assaying lactone hydrolysis). Such proteins, when expressed from recombinant DNA constructs, can be used in therapeutic embodiments of the invention described below.

Still other embodiments of the present invention provide PON3 homologs which have intracellular half-lives dramatically different than the corresponding wild-type protein. For example, the altered protein are rendered either more stable or less stable to proteolytic degradation or other cellular process that result in destruction of, or otherwise inactivate PON3. Such homologs, and the genes that encode them, can be utilized to alter the pharmaceutical activity of PON3 by modulating the half-life of the protein. For instance, a short half-life can give rise to more transient PON3 biological effects. As above, such proteins find use in pharmaceutical applications of the present invention.

In some embodiments of the combinatorial mutagenesis approach of the present invention, the amino acid sequences for a population of PON3 homologs are aligned, preferably to promote the highest homology possible. Such a population of variants can include, for example, PON3 homologs from one or more species, or PON3 homologs from the same species but which differ due to mutation. Amino acids that appear at each position of the aligned sequences are selected to create a degenerate set of combinatorial sequences.

In a preferred embodiment of the present invention, the combinatorial PON3 library is produced by way of a degenerate library of genes encoding a library of polypeptides that each include at least a portion of candidate PON3-protein sequences. For example, a mixture of synthetic oligonucleotides is enzymatically ligated into gene sequences such that the degenerate set of candidate PON3 sequences are expressible as individual polypeptides, or alternatively, as a set of larger fusion proteins (e.g., for phage display) containing the set of PON3 sequences therein.

There are many ways by which the library of potential PON3 homologs can be generated from a degenerate oligonucleotide sequence. In some embodiments, chemical synthesis of a degenerate gene sequence is carried out in an automatic DNA synthesizer, and the synthetic genes are ligated into an appropriate gene for expression. The purpose of a degenerate set of genes is to provide, in one mixture, all of the sequences encoding the desired set of potential PON3 sequences. The synthesis of degenerate oligonucleotides is well known in the art (See e.g., Narang, Tetrahedron Lett., 39:39 [1983]; Itakura et al., Recombinant DNA, in Walton (ed.), *Proceedings of the 3rd Cleveland Symposium on Macromolecules*, Elsevier, Amsterdam, pp 273–289 [1981]; Itakura et al., Annu. Rev. Biochem., 53:323 [1984]; Itakura et al., Science 198:1056 [1984]; Ike et al., Nucl. Acid Res., 11:477 [1983]). Such techniques have been employed in the directed evolution of other proteins (See e.g., Scott et al., Science, 249:386–390 [1980]; Roberts et al., Proc. Natl. Acad. Sci. USA, 89:2429–2433 [1992]; Devlin et al., Science, 249: 404–406 [1990]; Cwirla et al., Proc. Natl. Acad. Sci. USA, 87: 6378–6382 [1990]; as well as U.S. Pat. Nos. 5,223,409, 5,198,346, and 5,096,815, each of which is incorporated herein by reference).

A wide range of techniques are known in the art for screening gene products of combinatorial libraries made by point mutations, and for screening cDNA libraries for gene products having a certain property. Such techniques are generally adaptable for rapid screening of the gene libraries generated by the combinatorial mutagenesis of PON3 homologs. The most widely used techniques for screening large gene libraries typically comprise cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate sequences created by combinatorial mutagenesis techniques.

Accordingly, in one embodiment of the present invention, the candidate PON3 gene products are displayed on the surface of a cell or viral particle, and the ability of particular cells or viral particles to hydrolyze a particular lactone is assayed using the techniques described in Example 2. In other embodiments of the present invention, the gene library is cloned into the gene for a surface membrane protein of a bacterial cell, and the resulting fusion protein detected by panning (WO 88/06630; Fuchs et al., BioTechnol., 9:1370–1371 [1991]; and Goward et al., TIBS 18:136–140 [1992]). In other embodiments of the present invention, fluorescently labeled molecules that bind PON3 (e.g., lactones), can be used to score for potentially functional PON3 homologs. Cells are visually inspected and separated under a fluorescence microscope, or, where the morphology of the cell permits, separated by a fluorescence-activated cell sorter.

In an alternate embodiment of the present invention, the gene library is expressed as a fusion protein on the surface of a viral particle. For example, foreign peptide sequences are expressed on the surface of infectious phage in the filamentous phage system, thereby conferring two significant benefits. First, since these phage can be applied to affinity matrices at very high concentrations, a large number of phage can be screened at one time. Second, since each infectious phage displays the combinatorial gene product on its surface, if a particular phage is recovered from an affinity matrix in low yield, the phage can be amplified by another round of infection. The group of almost identical *E. coli* filamentous phages M13, fd, and fl are most often used in phage display libraries, as either of the phage gIII or gVIII coat proteins can be used to generate fusion proteins without disrupting the ultimate packaging of the viral particle (See e.g., WO 90/02909; WO 92/09690; Marks et al., J. Biol. Chem., 267:16007–16010 [1992]; Griffths et al., EMBO J., 12:725–734 [1993]; Clackson et al., Nature, 352:624–628 [1991]; and Barbas et al., Proc. Natl. Acad. Sci., 89:4457–4461 [1992]).

In another embodiment of the present invention, the recombinant phage antibody system (e.g., RPAS, Pharmacia Catalog number 27-9400-01) is modified for use in expressing and screening of PON3 combinatorial libraries. The pCANTAB 5 phagemid of the RPAS kit contains the gene that encodes the phage gIII coat protein. In some embodiments of the present invention, the PON3 combinatorial gene library is cloned into the phagemid adjacent to the gIII signal sequence such that it is expressed as a gIII fusion protein. In other embodiments of the present invention, the phagemid is used to transform competent *E. coli* TG1 cells after ligation. In still other embodiments of the present invention, transformed cells are subsequently infected with M13KO7 helper phage to rescue the phagemid and its candidate PON3 gene insert. The resulting recombinant phage contain phagemid DNA encoding a specific candidate PON3-protein and display one or more copies of the corresponding fusion coat protein. In some embodiments of the present invention, the phage-displayed candidate proteins that are capable of, for example, hydrolyzing a particular lactone substrate, are selected or enriched by panning. The bound phage is then isolated, and if the recombinant phage express at least one copy of the wild type gIII coat protein, they will retain their ability to infect *E. coli*. Thus, successive rounds of reinfection of *E. coli* and panning will greatly enrich for PON3 homologs, which can then be screened for further biological activities in order to differentiate agonists and antagonists.

In light of the present disclosure, other forms of mutagenesis generally applicable will be apparent to those skilled in the art in addition to the aforementioned rational mutagenesis based on conserved versus non-conserved residues. For example, PON3 homologs can be generated and screened using, for example, alanine scanning mutagenesis and the like (Ruf et al., Biochem., 33:1565–1572 [1994]; Wang et al., J. Biol. Chem., 269:3095–3099 [1994]; Balint et al. Gene 137:109–118 [1993]; Grodberg et al., Eur. J. Biochem., 218:597–601 [1993]; Nagashima et al., J. Biol. Chem., 268:2888–2892 [1993]; Lowman et al., Biochem., 30:10832–10838 [1991]; and Cunningham et al., Science, 244:1081–1085 [1989]), by linker scanning mutagenesis (Gustin et al., Virol., 193:653–660 [1993]; Brown et al., Mol. Cell. Biol., 12:2644–2652 [1992]; McKnight et al., Science, 232:316); or by saturation mutagenesis (Meyers et al., Science, 232:613 [1986]).

8. Chemical Synthesis of PON3

In an alternate embodiment of the invention, the coding sequence of Pon3 is synthesized, whole or in part, using chemical methods well known in the art (See e.g., Caruthers et al., Nucl. Acids Res. Symp. Ser., 7:215–233 [1980]; Crea and Horn, Nucl. Acids Res., 9:2331 [1980]; Matteucci and Caruthers, Tetrahedron Lett., 21:719 [1980]; and Chow and Kempe, Nucl. Acids Res., 9:2807–2817 [1981]). In other embodiments of the present invention, the protein itself is produced using chemical methods to synthesize either an entire PON3 amino acid sequence or a portion thereof. For example, peptides are synthesized by solid phase techniques, cleaved from the resin, and purified by preparative high performance liquid chromatography (See e.g., Creighton, *Proteins Structures And Molecular Principles*, W H Freeman and Co, New York N.Y. [1983]). In other embodiments of the present invention, the composition of the synthetic peptides is confirmed by amino acid analysis or sequencing (See e.g., Creighton, supra).

Direct peptide synthesis can be performed using various solid-phase techniques (Roberge et al., Science, 269:202–204 [1995]) and automated synthesis may be achieved, for example, using ABI 431A Peptide Synthesizer (Perkin Elmer) in accordance with the instructions provided by the manufacturer. Additionally, the amino acid sequence of PON3, or any part thereof, may be altered during direct synthesis and/or combined using chemical methods with other sequences to produce a variant polypeptide.

II. PON-3 Polypeptides

The present invention provides PONs polypeptides as well as variants, homologs, mutants or fusion proteins thereof.

A. Purification of Rabbit PON3

In some embodiments of the present invention, PON3 polypeptides purified from rabbit serum are provided. In one illustrative example (Example 3), PON3 is purified from rabbit serum. Both PON1 and PON3 are present in rabbit serum and arylesterase activity (phenyl acetate hydrolysis) and statinase activity (lovastatin hydrolysis) were both monitored to localize PON1 and PON3, respectively, in the column chromatographic fractions.

In Example 3, rabbit serum statinase activity was purified to apparent homogeneity. During the first step of the purification (Blue Agarose column) all of the statinase (PON3) activity co-eluted with the arylesterase (PON1) activity. However, both activities were almost completely separated by the later anion exchange chromatography step. The peak arylesterase activity was eluted at 87 mM NaCl and the peak statinase at 105 mM NaCl. Statinase activity was further purified through a second DEAE and a Sephacryl 200 gel filtration columns and correlated with the pattern of a 40 kDa protein on SDS-PAGE. Table 3 (See Example 3) shows the purification profile of PON3 statinase activity. PON3 was purified 302-fold in 5 chromatography steps. The overall yield was 1%.

PON3 and two contaminating proteins were transferred to PVDF membrane by western blotting and submitted for N-terminal sequencing. The resolved N-terminal sequences are shown in Table 4 (See Example 3). The N-terminus of the 40 kDa protein is identical with the deduced amino acid sequence of the rabbit PON3 cDNA (the cloning of rabbit PON3 cDNA is described in Example 1), and 96% identical with the sequence of microsomal rabbit PON (msPON Ozols, Biochem J, 338:265–272 [1999]). The two contaminating proteins were identified as a homolog of human platelet activated factor acetyl hydrolase (PAF-AH) precursor (50 kDa contaminant) (Tjoelker et al., Nature, 374:549–553 [1995]). The N-terminus of the 63 kDa protein is 93% identical with the both human VNNI (Granjeaud et al., Immunogenetics, 49:964–972 [1999]) and mouse vanin 1 (Aurrand-Lions et al., Immunity, 5:391–405 [1996]).

The decoded amino acid sequence of rabbit PON3 was aligned with several known PON genes from a variety of organisms. The results are shown in FIG. 2. Comparison of PON3 with other PON genes finds use in several embodiments of the present invention; as discussed herein.

B. Comparison of PON1 and PON3 Lactonase Activity

In some illustrative examples of the present invention, the biochemical properties of PON3 were investigated. An understanding of the biochemical properties of PON3 finds use in screening mutants, homologs, variants, and fusion proteins of PON3 generated in some embodiments of the present invention. In addition, and understanding of the biochemical properties of PON3 allows one select appropriate therapeutic uses for PON3 polypeptides.

Rabbit PON1 was also purified from rabbit serum (described in Example 1) and the lactonase activities of PON1 and PON3 were compared. Methods for performing lactonase assays are described in Example 2. A comparison of purified rabbit serum PON3 and PON1 hydrolytic activities with paraoxon, aromatic esters and lactones is presented in Table 2. Phenyl acetate and paraoxon are very poor substrates for PON3, whereas the rate of hydrolysis was 30–200 fold higher with dihydrocoumarin, 2-coumaronone and some 6 and 5 member ring lactones with aliphatic substituents. In contrast to PON1, PON3 has no activity with unsubstituted lactones as well as with 4 and 7 member ring lactones. PON3 requires at least one methylene group in γ- or δ-position (for the γ- or δ-lactones, respectively) and its lactonase activity increases with the number of carbon atoms in the aliphatic chain (up to 6 for the 7-lactones and up to 7 for the 8 lactones, respectively). These results indicate that although both PON1 and PON3 hydrolyze lactones, the substrate specificity varies widely between them.

In some embodiments of the present invention, the ability of PON3 to preferentially hydrolyze certain classes of lactones is used as a screening assay for the activity of the variants, homologs, and mutants of PON3 described above. In other embodiment, the assay is used to determine the biological activity of pharmaceutical compositions.

TABLE 2

PON3 and PON1 Substrate Specificity

| Substrate | PON3 (μmol/min/mg) | PON1 (μmol/min/mg) | PON1/PON3 Ratio |
|---|---|---|---|
| Phenyl Acetate | 1.0 | 768.7 | 769 |
| Thiophenyl Acetate | 0.48 | 259 | 540 |
| β-Naphtyl Acetate | 4.6 | 138.8 | 30 |
| Paraoxon (at pH 8.0) | <0.0075[1] | 4.76 | 638 |
| Dihydrocoumarin | 220 | 192.3 | 0.9 |
| 2-Coumaronone | 32.4 | 136.6 | 4.0 |
| α-Br-2-Coumaronone | 2.8 | 270.1 | 97 |
| Homogentisic acid lactone | | | |
| γ-Valerolactone | 3.0 | 78.4 | 26 |
| γ-Hexalactone | 4.6 | 96.0 | 21 |
| γ-Heptalactone | 8.6 | 107 | 12 |
| γ-Octalactone | 29 | 104.5 | 3.6 |
| γ-Nonalactone | 60 | 79.6 | 1.3 |
| γ-Decalactone | 50.2 | 92 | 1.8 |
| γ-Undecalactone | 44.2 | 87.4 | 2 |
| γ-phenyl-γ-butyrolactone | 20.4 | 203 | 10 |
| β-methyl-γ-octalactone | 3 | 34.8 | 12 |
| γ-methylene-γ-butyrolactone | 12 | 622 | 52 |
| α-Angelica lactone | 3.4 | 175.1 | 52 |
| δ-Hexalactone | 3.6 | 207 | 58 |
| δ-Nonalactone | 44 | 142 | 3.4 |
| δ-Decalactone | 73 | 134.8 | 1.8 |
| δ-Undecalactone | 90 | 186.8 | 2.1 |
| δ-Dodecalactone | 98.2 | 179.4 | 1.8 |

[1]Negligible to no detectable activity.

C. Association of PON1 and PON3 with HDLs

In one illustrative example of the present invention (Example 4), the association of PON3 with HDLs was screened. Rabbit serum lipoproteins were separated by both gel filtration and ultracentrifugation. The presence of PON1 and PON3 in the various lipoprotein fractions was monitored by statinase activity (PON3) or arylesterase and paraoxonase activity (PON1).

Figure 6:
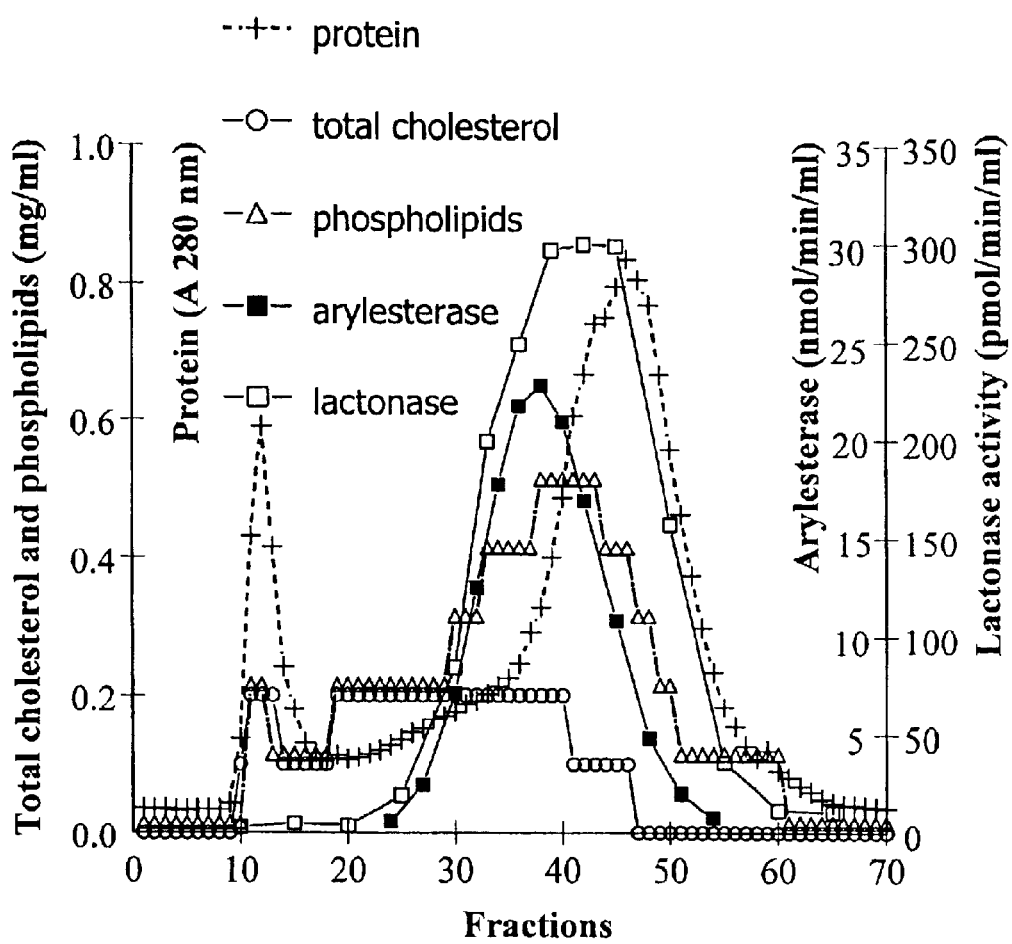
FIG. 6 shows the distribution of PON1 or PON3 associated arylesterase (with phenyl acetate) and statinase (with lovastatin) activities, total cholesterol, and phospholipids in gel filtration fractions.

The majority of both the PON3 and PON1 associated activities are associated with the HDL fraction. FIG. 6 shows the results of the gel filtration experiment described in Example 4. The figure shows distribution of arylesterase (with phenyl acetate) and statinase (with lovastatin) activities, total cholesterol, and phospholipids in the gel filtration fractions. FIG. 6 indicates that statinase and arylesterase activities co-elute with the phospholipid.

Figure 7:
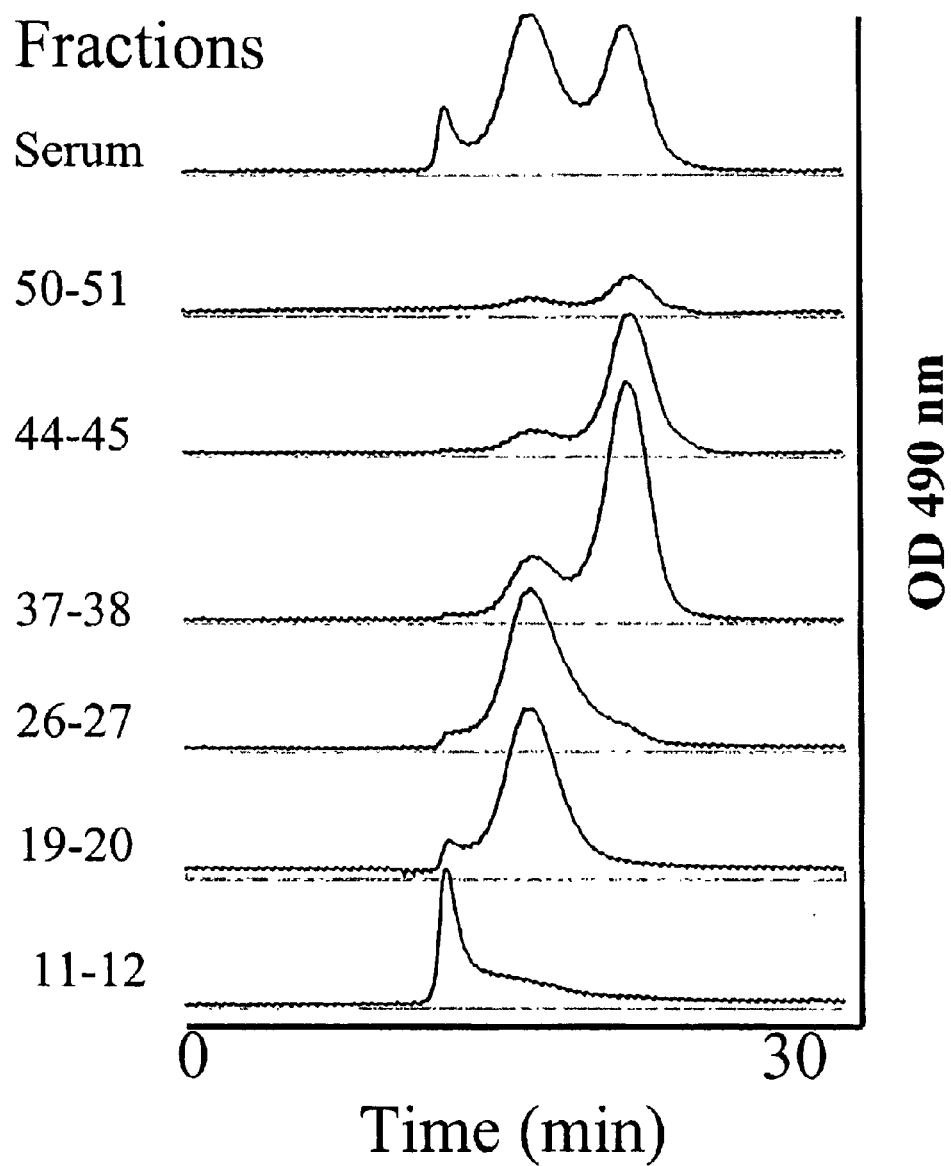
FIG. 7 shows chromatograms of lipoprotein cholesterol distribution of combined and concentrated fractions constituting each lipoprotein or activity peak

FIG. 7 shows chromatograms of lipoprotein cholesterol distribution of combined and concentrated fractions constituting each lipoprotein or activity peak (numbers are indicated in the left upper corner). The fractions containing the majority of the HDL correspond to the peak of the arylesterase and statinase activities (as determined by FIG. 6), indicating that the PON1 and PON3 activities are associated with the HDL fraction.

In some embodiments of the present invention, the association of PON3 with HDLs is used to screen variants, homologs, mutants, and fusions of PON3 for activity. In other embodiments, the assay is used to screen such proteins for their biological activity.

D. PON3 Protects Against LDL Oxidation

In one illustrative example (Example 5) of the present invention, the ability of PON3 to protect against LDL oxidation was assayed. In this example, LDL oxidation was induced by the incubation of the lipoprotein with 2–10 μM $CuSO_4$ in the air, in the absence or presence of PON3 or PON 1, for up to 5 h at 37° C. The kinetics of lipoprotein oxidation was followed by monitoring the conjugated dienes formation at 234 nm (Esterbauer et al., Free Radical Res Commun, 6:67–75 [1989]) using a quartz microtiter plate in a SPECTRAmax® 190 plate reader (Molecular Devices). Lipoprotein oxidation was also determined by the lipid peroxides test, which analyzes lipid peroxides by their capacity to convert iodide to iodine, as measured photometrically at 365 nm (E1-Saadani et al., J Lipid Res, 30:627–630 [1989]).

Figure 8:
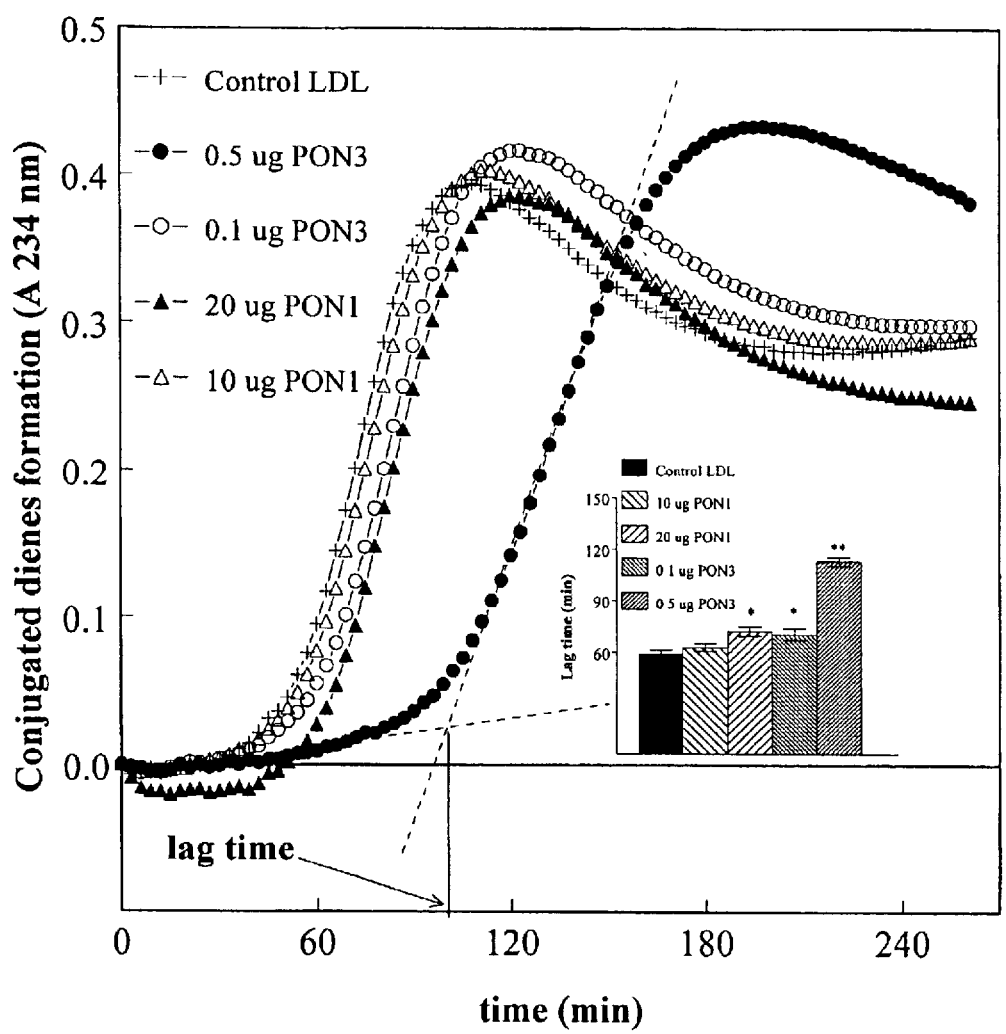
FIG. 8 shows levels of diene formation in the presence and absence of PON3 used in some embodiments of the present invention.
Figure 9:
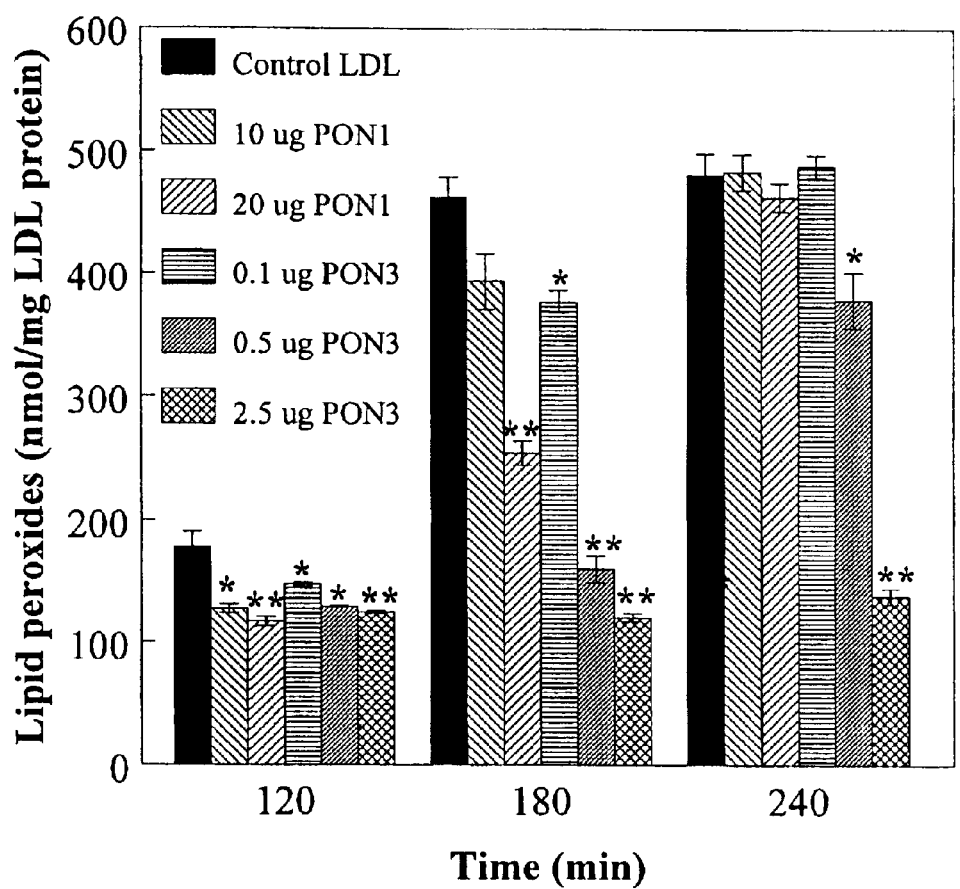
FIG. 9 shows levels of lipid peroxides in the presence and absence of PON3 used in some embodiments of the present invention.

Results are shown in FIG. 8 (diene formation) and FIG. 9 (lipid peroxides). PON3 was significantly better at inhibiting both conjugated diene and lipid peroxide formation than PON1. In fact, PON3 was more than 50 times more potent per μg protein at protecting LDL against copper-induced oxidation compared to PON1.

In some embodiments of the present invention, the association of PON3 with HDLs is used to screen variants, homologs, mutants, and fusions of PON3 for activity. In other embodiments, the assay is used to screen such proteins for their biological activity.

E. Generation of PON3 Antibodies

In some embodiments of the present invention, antibodies are generated to allow for the detection and characterization of PON3 protein. The antibodies may be prepared using various immunogens. In one embodiment, the immunogen is a rabbit PON3 peptide (e.g., an amino acid sequence as depicted in SEQ ID NO:8, or fragments thereof) to generate antibodies that recognize rabbit PON3. Such antibodies include, but are not limited to polyclonal, monoclonal, chimeric, single chain, Fab fragments, and Fab expression libraries.

Various procedures known in the art may be used for the production of polyclonal antibodies directed against PON3. For the production of antibody, various host animals can be immunized by injection with the peptide corresponding to the PON3 epitope including but not limited to rabbits, mice, rats, sheep, goats, etc. In a preferred embodiment, the peptide is conjugated to an immunogenic carrier (e.g., diphtheria toxoid, bovine serum albumin (BSA), or keyhole limpet hemocyanin (KLH)). Various adjuvants may be used to increase the immunological response, depending on the host species, including but not limited to Freund's (complete and incomplete), mineral gels (e.g., aluminum hydroxide), surface active substances (e.g., lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*).

For preparation of monoclonal antibodies directed toward PON3, it is contemplated that any technique that provides for the production of antibody molecules by continuous cell lines in culture finds use with the present invention (See e.g., Harlow and Lane, *Antibodies: A Laboratory Manual, Cold Spring Harbor Laboratory Press,* Cold Spring Harbor, N.Y.). These include but are not limited to the hybridoma technique originally developed by Kohler and Milstein (Kohler and Milstein, Nature, 256:495–497 [1975]), as well as the trioma technique, the human B-cell hybridoma technique (See e.g., Kozbor et al., Immunol. Tod., 4:72 [1983]), and the EBV-hybridoma technique to produce human monoclonal antibodies (Cole et al., in *Monoclonal Antibodies and Cancer Therapy*, Alan R. Liss, Inc., pp. 77–96 [1985]).

In an additional embodiment of the invention, monoclonal antibodies are produced in germ-free animals utilizing technology such as that described in PCT/US90/02545). Furthermore, it is contemplated that human antibodies may be generated by human hybridomas (Cote et al., Proc. Natl. Acad. Sci. USA, 80:2026–2030 [1983]) or by transforming human B cells with EBV virus in vitro (Cole et al., in *Monoclonal Antibodies and Cancer Therapy*, Alan R. Liss, pp. 77–96 [1985]).

In addition, it is contemplated that techniques described for the production of single chain antibodies (U.S. Pat. No. 4,946,778; herein incorporated by reference) find use in producing PON3-specific single chain antibodies. An additional embodiment of the invention utilizes the techniques described for the construction of Fab expression libraries (Huse et al., Science, 246:1275–1281 [1989]) to allow rapid and easy identification of monoclonal Fab fragments with the desired specificity for PON3.

It is contemplated that any technique suitable for producing antibody fragments finds use in generating antibody fragments that contain the idiotype (antigen binding region) of the antibody molecule. For example, such fragments include but are not limited to: F(ab')2 fragment that can be produced by pepsin digestion of the antibody molecule; Fab' fragments that can be generated by reducing the disulfide bridges of the F(ab')2 fragment, and Fab fragments that can be generated by treating the antibody molecule with papain and a reducing agent.

In the production of antibodies, it is contemplated that screening for the desired antibody is accomplished by techniques known in the art (e.g., radioimmunoassay, ELISA (enzyme-linked immunosorbant assay), "sandwich" immunoassays, immunoradiometric assays, gel diffusion precipitin reactions, immunodiffusion assays, in situ immunoassays (e.g., using colloidal gold, enzyme or radioisotope labels, for example), Western blots, precipitation reactions, agglutination assays (e.g., gel agglutination assays, hemagglutination assays, etc.), complement fixation assays, immunofluorescence assays, protein A assays, and immunoelectrophoresis assays, etc.

In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many methods are known in the art for detecting binding in an immunoassay and are within the scope of the present invention. As is well known in the art, the immunogenic peptide should be provided free of the carrier molecule used in any immunization protocol. For example, if the peptide was conjugated to KLH, it may be conjugated to BSA, or used directly, in a screening assay.)

In some embodiments of the present invention, the foregoing antibodies are used in methods known in the art relating to the expression of PON3 (e.g., for Western blotting), measuring levels thereof in appropriate biological samples, etc. The antibodies can be used to detect PON3 in a biological sample from an individual. The biological sample can be a biological fluid, such as, but not limited to, blood, serum, plasma, interstitial fluid, urine, cerebrospinal fluid, and the like, containing cells.

The biological samples are then be tested directly for the presence of rabbit PON3 using an appropriate strategy (e.g., ELISA or radioimmunoassay) and format (e.g., microwells, dipstick (e.g., as described in International Patent Publication WO 93/03367), etc. Alternatively, proteins in the sample can be size separated (e.g., by polyacrylamide gel electrophoresis (PAGE), in the presence or not of sodium dodecyl sulfate (SDS), and the presence of PON3 detected by immunoblotting (Western blotting). Immunoblotting techniques are generally more effective with antibodies generated against a peptide corresponding to an epitope of a protein, and hence, are particularly suited to the present invention.

F. Drug Screening Using PON3

The present invention provides methods and compositions for using PON3 as a target for screening drugs that alter lactone production, metabolism, and clearance, and thus the physiological effects of PON3 (e.g., effects on lactone metabolism in oxidative damage and sepsis). For example, drugs can be identified by screening for compounds that effect lactone metabolism.

In one screening method, the two-hybrid system is used to screen for compounds (e.g., drug) capable of altering (e.g., enhancing) PON3 function (e.g., lactonase activity) in vitro or in vivo. In one embodiment, a GAL4 binding site, linked to a reporter gene such as lacZ, is contacted in the presence and absence of a candidate compound with a GAL4 binding domain linked to a PON3 fragment and a GAL4 transactivation domain II linked to a fragment of an enzyme involved in lactone metabolism. Expression of the reporter gene is monitored and a increase or decrease in the expression is an indication that the candidate compound affects the interaction of PON3 with another enzyme that effects lactone metabolism.

In another screening method, candidate compounds are evaluated for their ability to alter lactone metabolism (e.g. in sepsis, oxidative damage, or chemical toxicity) by contacting PON3, PON3-associated proteins, or fragments thereof, with the candidate compound and determining binding of the candidate compound to the peptide. The protein or protein fragments is/are immobilized using methods known in the art such as binding a GST-PON3 fusion protein to a polymeric bead containing glutathione. A chimeric gene encoding a GST fusion protein is constructed by fusing DNA encoding the polypeptide or polypeptide fragment of interest to the DNA encoding the carboxyl terminus of GST (See e.g., Smith et al., Gene 67:31 [1988]). The fusion construct is then transformed into a suitable expression system (e.g., *E. coli* XA90) in which the expression of the GST fusion protein can be induced with isopropyl-β-D-thiogalactopyranoside (IPTG). Induction with IPTG should yield the fusion protein as a major constituent of soluble, cellular proteins. The fusion proteins can be purified by methods known to those skilled in the art, including purification by glutathione affinity chromatography. Binding of the candidate compound to the proteins or protein fragments is correlated with the ability of the compound to alter lactone metabolism and thus regulate lactone-mediated physiological effects (e.g., sepsis, oxidative damage, and chemical toxicity).

In another screening method, one of the components of the lactone metabolism system, such as PON3 or a fragment of PON3, is immobilized. Polypeptides can be immobilized using methods known in the art, such as adsorption onto a plastic microtiter plate or specific binding of a GST-fusion protein to a polymeric bead containing glutathione. For example, GST-PON3 is bound to glutathione-Sepharose beads. The immobilized peptide is then contacted with another peptide with which it is capable of binding in the presence and absence of a candidate compound. Unbound peptide is then removed and the complex solubilized and analyzed to determine the amount of bound labeled peptide. A decrease in binding is an indication that the candidate compound inhibits the interaction of PON3 with the other peptide. A variation of this method allows for the screening of compounds that are capable of disrupting a previously-formed protein/protein complex. For example, in some embodiments a complex comprising PON3 or a PON3 fragment bound to another peptide is immobilized as described above and contacted with a candidate compound. The dissolution of the complex by the candidate compound correlates with the ability of the compound to disrupt or inhibit the interaction between PON3 and the other peptide.

Another technique for drug screening provides high throughput screening for compounds having suitable binding affinity to PON3 peptides and is described in detail by Geysen (WO 84/03564). Briefly, large numbers of different small peptide test compounds are synthesized on a solid substrate, such as plastic pins or some other surface. The peptide test compounds are then reacted with PON3 peptides and washed. Bound PON3 peptides are then detected by methods well known in the art.

Another technique uses PON3 antibodies, generated as discussed above. Such antibodies capable of specifically binding to PON3 peptides compete with a test compound for binding to PON3. In this manner, the antibodies are used to detect the presence of any peptide that shares one or more antigenic determinants of the PON3 peptide.

The present invention contemplates many other means of screening compounds. The examples provided above are presented merely to illustrate certain techniques available. One of ordinary skill in the art will appreciate that many other screening methods can be used.

III. Therapeutic Uses of PON3

The unique substrate specificity of PON3 (See Table 3) allows for a variety of therapeutic uses for PON3 polypeptides as well as variants, homologs, mutants, and fusion proteins thereof. Several illustrative examples are provided below.

A. Sepsis

In some embodiments of the present invention, PON3 or variants, homologs, mutants, or fusion proteins thereof, are used to treat sepsis. It has been shown that HDL can inactivate bacterial lipopolysacharide (LPS) and thereby prevent endotoxemic symptoms (Johnson et al., Am. J. Patholo., 88, 559–574, [1977]). Moreover, i.p. injection of purified human PON1 in mice before or up to 2 hours after $LD_{100}$ dose of LPS resulted in 60% survival of the pretreated and 30% of post-treated animals (LaDu et al., Chem Biol Interact., 119–120:379–88, [1999]). PON knockout mice are extremely sensitive to LPS. These and other data show that PON1 is able to protect cells from LPS and prevent or greatly reduce the release of cytokines.

Due to the finding that PON3 prefers lipophilic substrates (See Table 2), PON3 therapeutic compositions find use in the inhibition of endotoxinemia, in particular, Sepsis. In some embodiments, PON3 is used as a prophylactic treatment for sepsis. In some embodiments, an effective dose of PON3 is given intravenously prior to surgery or following any procedure or incident that may lead to sepsis. In other embodiments, PON3 is used therapeutically by administering an effective dose of PON3 intravenously to patients exhibiting signs of sepsis. Pharmaceutical composition of PON3 are discussed in Section IV Below.

B. Oxidative Damage

Therapeutic embodiments of the present invention are not limited to the treatment of Sepsis. In some embodiments of the present invention, PON3 or variants, homologs, mutants, or fusion proteins thereof, are used in the treatment and prevention of oxidative damage in atherosclerosis. The oxidative hypothesis of atherosclerosis implies a central role for low density lipoprotein (LDL) oxidation. However, new anthiatherogenic properties have been recognized for high density lipoprotein (HDL), apart from their role in reverse cholesterol transport. Native HDL could protect LDL (and other lipid containing particles, e.g. red blood cells) from oxidation.

The present invention does not target one specific mechanism of oxidative damage in atherosclerosis. Indeed, an understanding of the mechanism of the invention is not necessary in order to produce the therapeutic compounds of the present invention. Different mechanisms of protection are envisioned, and include detoxification of oxidized phospholipids and reduction of hydroperoxides to their corresponding hydroxides. HDL can also inhibit oxidized LDL-induced transduction signals responsible for monocytes adhesion and transmigration. However, if the HDL itself undergoes oxidation it will lose some of its cholesterol effluxing capacity as well as its ability to protect LDL against oxidation, thus becoming atherogenic. The atheroprotective properties of native HDL depend on its constituents such as apoliproteins, e.g. apoAI and apoJ, and HDL-associated enzymes such as paraoxonase 1 (PON1), platelet-activating factor acetyl hydolase (PAF-AH) and lecthin-cholesterol acyltransferase (LCAT)). In particular, PON1 has been shown to protect both HDL and LDL against oxidation (Aviram et al., Arterioscler. Thromb. Vase. Biol. 18:1617–1624 [1998]; Aviram, Mol. Med. Today 5:381–138 [1999]). In addition, PON1 can destroy biologically active lipids in mildly oxidized LDL (Watson et al., J. Clin. Invest 96:2882–2891 [1995]), and can hydrolize lipid peroxides both on oxidized LDL (Aviram, Mol. Med. Today 5: 381–138 [1999]) and in coronary and carotid lesions (Aviram et al., 2000). Upon its interaction with oxidized LDL, PON1 undergoes inactivation (Aviram et al., Arterioscler. Thromb. Vase. Biol. 18:1617–1624 [1998]; Aviram, Mol. Med. Today, 5:381–138 [1999]), but this could be prevented by introducing other antioxidants. PON1 knockout mice fed an atherogenic diet are more susceptible to atherosclerosis than their wild type littermates. In addition, both HDL and LDL isolated from PON knockout mice (Shih et al., Nature, 394:284–287 [1998]) are more susceptible to oxidation than the wild type lipoproteins. Finally, HDL from PON knockout mice does not protect LDL against oxidation.

In addition, elevated levels of homocysteine are an independent risk factor for cardiovascular disease in humans (Langman and Cole, Clin. Chim Acta, 286:63–80 [1999]). Homocysteine is metabolized to homocysteine thiolactone (HTL), which can bind to lysine residues resulting in protein damage, LDL aggregation and macrophage scavenging (Jakuboski, J. Biol. Chem., 275:3957–2962 [2000]). Human PON1 has been shown to hydrolyze HTL.

PON3 is superior to PON1 (at least 50 times better) in the protection of LDL from oxidation in vitro (See Table 9). PON3 can also hydrolyse lactone drugs such as the hydroxymethyl glutaryl co-enzyme A (HMG-CoA) reductase inhibitors lovastatin and simvastatin (See Table 2).

In some embodiments of the present invention, PON3 is used to prevent damage caused by oxidative stress. Therapeutic compositions for these embodiments are described below in Section IV. In some embodiments, PON3 is used therapeutically by injecting an effective dose of PON3 intravenously into a patient with known vascular damage. In other embodiments, PON3 is used prophylactically to prevent restenosis of a vessel by giving an effective dose of the enzyme locally or intravenously during surgical procedures such as angioplasty or stent insertion. In still further embodiments, PON3 is used prophylacticly or therapeutically for preventing oxidative damage including, but not limited to atherosclerosis, neuropathy, and micro- and microangiopathy in systemic diseases such as diabetes.

C. Chemical Toxicity

Therapeutic embodiments of the present invention are not limited to the treatment of Sepsis or oxidative damage in atherosclerosis. In some embodiments of the present invention, PON3 or variants, homologs, mutants, or fusion proteins thereof, are used in the treatment and prevention of chemical toxicity.

Paraoxonase that circulates in the blood is perfectly positioned to hydrolyze toxic chemicals circulating in the blood. These chemicals include environmental toxins, compounds ingested in the diet, as well as drugs. Differences in PON1 (e.g., the Q192R polymorphism which affects the speed at which certain organophosphates are hydrolyzed) might predispose individuals to chemical toxicity. A recent paper investigating the Gulf War syndrome found that soldiers believed to be exposed to such chemicals were more likely to exhibit neurological signs of chemical toxicity if they were phenotypically PON1 R192 or if they had low levels of PON1 Q192 (Haley et al. Toxicol. Applied Pharmacol., 157:227–233, [1999]).

Since PON3 hydrolyzes a number of lactone substrates, it is contemplated that PON3 formulations are efficacious at detoxifying a patient exposed to such chemicals. In some embodiments of the present invention, PON3 is used in the treatment of toxic side effects of HMG-CoA reductase inhibitors such as lovastatin and simvastatin in patients on hemodialysis. In other embodiments, PON3 is administered intravenous as soon as possible after the exposure. In still further embodiments, PON3 is given prophylactically, for example, including, but not limited to, an intravenous injection of an effective dose prior to anticipated exposure.

D. Polypeptide Targeting

The N-terminal leader sequence of human PON1 is retained in the mature protein. This portion of the protein is responsible for the association of PON1 with HDL (Sorenson et al., Thromb. Vase. Biol., 19:2215–2225 [1999]). Rabbit PON3 in the serum is HDL-associated (See Example 4). The N-terminal leader sequence of rabbit PON3 is also retained in the mature protein and the first 10 residues of the retained leader sequence is 80% identical to the same region of human PON1. The present invention does not target one specific mechanism of PON3 secretion into the blood. Indeed, an understanding of the mechanism of the invention is not necessary in order to produce the therapeutic compounds of the present invention. However, this region of PON3 is likely responsible for it's secretion into the blood and its association with HDL.

In accordance with yet a further aspect of the present invention, there is provided a polynucleotide which encodes the fragment of PON3 polypeptide responsible for the secretion of the PON3 and its binding to HDL. In some embodiments, this polynucleotide (polypeptide) enables and/or improves the production of recombinant chimeric proteins or other macromolecules, their secretion and binding to natural or artificial HDL, liposomes or other lipid-rich particles used for therapeutic purposes.

It should be noted that the above uses, as well as other uses can be conducted on a number hosts in a variety of ways. For example, the present invention contemplates ex vivo therapies, wherein cells or tissue from a subject are remove from the subjected, treated with any of the compositions of the present invention and returned to the host. Such ex vivo application find use in both screening assays and in therapeutic applications. The various PON-3 polypeptides of the present invention also find use in combination therapies. For example, mixtures comprising PON-3 peptides or chimeras and other PON polypeptides (e.g., PON-1 and PON-2) may be used in place of the PON-3 formulations described above.

IV. Pharmaceutical Compositions Containing PON3 Nucleic Acid, Peptides, and Analogs The present invention further provides pharmaceutical compositions that may comprise all or portions of PON3 polynucleotide sequences, PON3 polypeptides, inhibitors or antagonists of PON3 bioactivity, including antibodies, alone or in combination with at least one other agent, such as a stabilizing compound, and may be administered in any sterile, biocompatible pharmaceutical carrier, including, but not limited to, saline, buffered saline, dextrose, and water.

The compounds of the present invention find use in treating diseases or altering physiological states as discussed above. Peptides can be administered to the patient intravenously in a pharmaceutically acceptable carrier such as physiological saline. Standard methods for intracellular delivery of peptides can be used (e.g., delivery via liposome). Such methods are well known to those of ordinary skill in the art. The formulations of this invention are useful for parenteral administration, such as intravenous, subcutaneous, intramuscular, and intraperitoneal.

As is well known in the medical arts, dosages for any one patient depends upon many factors, including the patient's size, body surface area, age, the particular compound to be administered, sex, time and route of administration, general health, and interaction with other drugs being concurrently administered.

Accordingly, in some embodiments of the present invention, PON3 polypeptides can be administered to a patient alone, or in combination with other nucleotide sequences, drugs or hormones or in pharmaceutical compositions where it is mixed with excipient(s) or other pharmaceutically acceptable carriers. In one embodiment of the present invention, the pharmaceutically acceptable carrier is pharmaceutically inert.

Depending on the condition being treated, these pharmaceutical compositions may be formulated and administered systemically or locally. Techniques for formulation and administration may be found in the latest edition of "Remington's Pharmaceutical Sciences" (Mack Publishing Co, Easton Pa.). Suitable routes may, for example, include oral or transmucosal administration; as well as parenteral delivery, including intramuscular, subcutaneous, intramedullary, intrathecal, intraventricular, intravenous, intraperitoneal, or intranasal administration.

For injection, the pharmaceutical compositions of the invention may be formulated in aqueous solutions, preferably in physiologically compatible buffers such as Hanks' solution, Ringer's solution, or physiologically buffered saline. For tissue or cellular administration, penetrants appropriate to the particular barrier to be permeated are used in the formulation. Such penetrants are generally known in the art.

In other embodiments, the pharmaceutical compositions of the present invention can be formulated using pharmaceutically acceptable carriers well known in the art in dosages suitable for oral administration. Such carriers enable the pharmaceutical compositions to be formulated as tablets, pills, capsules, liquids, gels, syrups, slurries, suspensions and the like, for oral or nasal ingestion by a patient to be treated.

Pharmaceutical compositions suitable for use in the present invention include compositions wherein the active ingredients are contained in an effective amount to achieve the intended purpose. For example, an effective amount of PON3 may be that amount that supresses or prevents one of the toxic responses discussed above. Determination of effective amounts is well within the capability of those skilled in the art, especially in light of the disclosure provided herein.

In addition to the active ingredients these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

The pharmaceutical compositions of the present invention may be manufactured in a manner that is itself known (e.g., by means of conventional mixing, dissolving, granulating, dragee-making, levigating, emulsifying, encapsulating, entrapping or lyophilizing processes).

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, etc; cellulose such as methyl cellulose, hydroxypropylmethyl-cellulose, or sodium carboxymethylcellulose; and gums including arabic and tragacanth; and proteins such as gelatin and collagen. If desired, disintegrating or solubilizing agents may be added, such as the cross-linked polyvinyl pyrrolidone, agar, alginic acid or a salt thereof such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, (i.e., dosage).

Pharmaceutical preparations which can be used orally include push-fit capsules made of gelatin, as well as soft, sealed capsules made of gelatin and a coating such as glycerol or sorbitol. The push-fit capsules can contain the active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Compositions comprising a compound of the invention formulated in a pharmaceutical acceptable carrier may be prepared, placed in an appropriate container, and labeled for treatment of an indicated condition. For polynucleotide or amino acid sequences of PON3, conditions indicated on the label may include treatment of the conditions discussed above.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM–50 mM histidine, 0.1%–2% sucrose, 2%–7% mannitol at a pH range of 4.5 to 5.5 that is combined with buffer prior to use.

For any compound used in the method of the invention, the therapeutically effective dose can be estimated initially from cell culture assays. Then, preferably, dosage can be formulated in animal models (particularly murine models) to achieve a desirable circulating concentration range that adjusts PON3 levels.

A therapeutically effective dose refers to that amount of PON which ameliorates or prevents symptoms of the disease state. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, and it can be expressed as the ratio $LD_{50}/ED_{50}$. Compounds which exhibit large therapeutic indices are preferred. The data obtained from these cell culture assays and additional animal studies can be used in formulating a range of dosage for human use. The dosage of such compounds lies preferably within a range of circulating concentrations that include the $ED_{50}$ with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors which may be taken into account include the severity of the disease state; age, weight, and gender of the patient; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature (See e.g., U.S. Pat. Nos. 4,657,760; 5,206,344; or 5,225,212, all of which are herein incorporated by reference).

Experimental

The following examples are provided in order to demonstrate and further illustrate certain preferred embodiments and aspects of the present invention and are not to be construed as limiting the scope thereof.

In the experimental disclosure which follows, the following abbreviations apply: eq (equivalents); M (Molar); μM (micromolar); N (Normal); mol (moles); mmol (millimoles); μmol (micromoles); nmol (nanomoles); g (grams); mg (milligrams); μg (micrograms); ng (nanograms); 1 or L (liters); ml (milliliters); μl (microliters); cm (centimeters); mm (millimeters); μm (micrometers); nm (nanometers); ° C. (degrees Centigrade); U (units), mU (milliunits); min. (minutes); sec. (seconds); % (percent); kb (kilobase); bp (base pair); PCR (polymerase chain reaction); BSA (bovine serum albumin); Invitrogen (Invitrogen, Carlsbad, Calif.); Midland Certified Reagent Company (Midland Certified Reagent Company, Midland, Tex.); Sigma (Sigma Chemical Co., St. Louis, Mo.); Boehringer Mannheim (Boehringer Mannheim, Corp., Indianapolis, Ind.); Qiagen (Qiagen, Valencia, Calif.); Stratagene (Stratagene Inc., La Jolla, Calif.); Molecular Devices (Molecular Devices, Sunnyvale, Calif.); Pierce (Pierce, Rockford, Ill.); Varian (Varian, Australia); National Biosciences (National Biosciences Inc, Plymouth Minn.); Merck (Merck & Co., Inc., West Point, Pa.); Pharmacia (Pharmacia, Peapack, N.J.); Wako Chemicals USA (Wako Chemicals USA, Inc., Richmond, Va.); Biorad (Biorad, Richmond, Calif.); Applied Biosystems (Applied Biosystems Inc., Foster City, Calif.); and NEB (New England Biolabs, Beverly, Mass.).

EXAMPLE 1

Cloning of Rabbit PON3

The nucleotide sequence of rabbit PON3 was obtained by RT-PCR of total liver RNA isolated from New Zealand White rabbits. Total rabbit liver mRNA was isolated using the RNA Easy Kit (Qiagen) following the supplier's protocol. RT-PCR was performed with the Titan One-tube RT-PCR System (Boehringer Mannheim) according to the manufacturer's instructions. Primers for the human PON3, Px3-6 (5'-GGCATAGAACTGTTCTGGTCCAAGAACC-3'; SEQ ID NO:1) and Px3-17 (5'-GCTTCTGAAGATATTGATATACTCCCCAGTGGGC-3'; SEQ ID NO:2) were purchased from Midland Certified Reagent Company. The RT-PCR products were separated on a 1% agarose gel. Bands of the expected size (as deduced by their similarity to the human PON3) were excised and submitted for sequencing in the University of Michigan DNA Sequencing Core Laboratory. Based on the obtained sequence, primers RPx3-4 (5'-CTCATCTGGTGC-AAAGTTTGG-3'; SEQ ID NO:3) and Rpx3-1 (5'-ACAACAACGCTCTCTTGTAC-3'; SEQ ID NO:4) were designed and than purchased from Gibco BRL, and used for amplification of the 5'- and 3'-ends of rabbit PON3's cDNA using a 5'3'RACE Kit (Boehringer Mannheim) according to the manufacturer's instructions. Based on the results from sequencing these fragments new primers RPx3-5 (5'-ATCGGAATTCCATGG- CGAAGCTCCTGC-3'; SEQ ID NO:5) and Rpx3-6 (5'-AGGCCTCGAGCTGGA-GACTAGAGCAC-3'; SEQ ID NO:6) were designed and used to amplify the full length cDNA. The PCR product (approximately 1200 bp) was cloned in the pCRII vector with TOPOTA Cloning Kit (Invitrogen) and sequenced. The sequence of rabbit PON3 clone (SEQ ID NO: 7) was submitted to GenBank and has accession number AF220944. Nucleotide and deduced amino acid sequences of PON3 are shown in FIG. 1.

The PON3 deduced amino acid sequence was aligned with other PON sequences using the DNA Star program. Sequences included are: rabPON3 total (rabbit PON3; SEQ ID NO:22); PON3 Ozols (MsPON from Ozols, Biochem J, 338:265 [1999]; SEQ ID NO:23); humanPON3aa (hPON3 from Primo-Parmo et at., Genomics, 33:498 [1996]; SEQ ID NO:24); mus PON 3 aa (SEQ ID NO:25); rab PON1 Clem (Furlong el al., Chem. Biol. Interact., 87:35 [1993]; SEQ ID NO:26); humpon1aa (Hasset et al., Biochemistry 30:10141 [1991]; SEQ ID NO:31); rPON2aa (SEQ ID NO:32); hPON2aa (Primo-Parmo et al., Genomics, 33:498 [1996]; SEQ ID NO:33); uspatpro (from Hudson et al., U.S. Pat. No. 5,629,193, [1997]; SEQ ID NO:34). The results are shown in FIG. 2.

EXAMPLE 2

Enzymatic Activities

This example describes a number of the enzymatic assays utilized to measure lactonase activity.

A. Esterase Activity

Esterase activities with substrates: phenyl acetate, S-phenyl thioacetate, α-naphtyl acetate and paraoxon were measured as described by Kuo and La Du (Kuo and La Du, Drug Metab. Dispos., 23:335 [1995]; Qan et al., Drug Metab Dispos, 19:100–106 [1991]. For example, arylesterase activity is measured using a molar difference extinction coefficient (difference in extinction coefficients of phenol vs. phenol acetate) of 1,310 $M^{-1}$ $cm^{-1}$, at 270 nm with 1.0 mM phenyl acetate in 50 mM Tris/HCl (pH 8.0):1.0 mM $CaCl_2$ buffer (Gan et al., supra). For the hydrolysis of thiophenyl acetate, the substrate is dissolved in methanol, and the reaction cuvettes contain 1.0 mM substrate in 50 mM Tris/HCl (pH 8.0):1.0 mM $CaCl_2$ buffer. The product, thiophenol, reacts with 5,5'-dithiobis(2-nitrobenzoic acid), and activity is calculated from a molar difference extinction coefficient of 13,600 $M^{-1}$ $cm^{-1}$ at 412 nm (Augustinsson and Axenfors, Anal. Biochem., 48:428 [1972]). For the hydrolysis of α-naphtyl acetate, substrates are dissolved in ethylene glycol monomethyl ether, and the reaction cuvettes contain 0.5 mM substrate in 50 mM Tris/HCl (pH 8.0):1.0 mM $CaCl_2$ buffer. Enzymatic activities are calculated from the molar extinction coefficients of 23,170 $M^{-1}$ $cm^{-1}$ at 235 nm. PON activity is measured with 1.0 mM paraoxon in 50 mM glycine:NaOH buffer (pH 10.5):1.0 mM $CaCl_2$ with or without 1.0 M NaCl. Enzymatic activities were calculated from a molar extinction coefficient of 18,290 $M^{-1}$ $cm^{-1}$ at 412 nm (Gan et al., supra). All enzymatic assays are performed at 25° C. For each assay, 5 µl of purified PON (1.5–2.5 µg of enzyme protein) is added to an assay cuvette. For all substrates, one unit of enzymatic activity is defined as 1 µmol of substrate hydrolyzed/min.

B. Hydrolysis of Aromatic Lactones

Hydrolysis of aromatic lactones was monitored by the increase in UV absorbance at 270 nm (dihydrocoumarin), 274 nm (2-coumaranone), and 290 nm (homogentisic acid lactone). Lactones were purchased from Sigma. In a typical experiment a cuvette contained 1 mM substrate (from a 100 MM stock solution, dissolved in methanol) in 50 mM Tris/HCl (pH 8.0), 1 mM CaCl2 and 5–20 µl enzyme source in a total volume of 1 ml. The molar difference extinction coefficients (difference in extinction coefficients of substrate and product) used to calculate the rate of hydrolysis were 1295, 876, and 816 $M^{-1}$ $cm^{-1}$ for dihydrocoumarin, 2-coumaranone and homogentisic acid lactone, respectively.

C. Hydrolysis of Non-Aromatic Lactones

The hydrolysis of other lactones was followed by a calorimetric assay with phenol red (Billecke, et al., Chem Biol Interact, 119–120:251–256, [1999]). The reaction cuvette contained 1 mM substrate (from a 100 mM stock solution, dissolved in methanol) in 2 mM HEPES at starting pH 8.0, 1 mM CaCl2, 0.004% (106 µM) phenol red, 0.005% bovine albumin, and 5–20 µl enzyme solution in a total volume of 1 ml. The rate of acid production was followed by monitoring the increase in absorbance at 422 nm as the color changed from red to yellow. The rate of hydrolysis was derived from a calibration curve obtained using known amounts of HCl.

All the above assays (Sections, A, B, and C) were performed at 25° C. using a dual beam Cary 3E UVN is Spectrophotometer (Varian). Reference cuvettes containing the appropriate buffer plus substrate were used in each assay to correct for any spontaneous hydrolysis.

D. Hydrolysis of Statin Lactones

The hydrolysis of the statin lactones (mevastatin, lovastatin and simvastatin) was analyzed by high performance liquid chromatography (HPLC) using a Beckman System Gold HPLC with a Model 126 Programmable Solvent Module, a Model 168 Diode Array Detector set at 238 nm, a Model 7125 Rheodyne manual injector valve with a 20 µl loop, and a Beckman ODS Ultrasphere column (C 18, 250×4.6 mm, 5 µm). Lovastatin (Mevacor) and simvastatin were purchased as 20 mg tablets from Merck, from which the lactones were extracted with chloroform, evaporated to dryness and redissolved in methanol. Mevastatin was purchased from Sigma.

In a final volume of 1 ml, 10–200 µl of enzyme solution and 10 µl of substrate solution in methanol (0.5 mg/ml) were incubated at 25° C. in 50 mM Tris/HCl (pH 7.6), 1 mM $CaCl_2$. Aliquots (100 µl) were removed at specified times and added to acetonitrile (100 µl), vortexed, and centrifuged for one minute at maximum speed (Beckman microfuge). The supernatants were poured into new tubes, capped and stored on ice until HPLC analysis.

Samples were eluted isocratically at a flow rate of 1.0 ml/min with a mobile phase consisting of the following: A=acetic acid/acetonitrile/water (2:249:249, v/v/v) and B=acetonitrile, in A/B ratios of 50/50, 45/55 and 40/60 for mevastatin, lovastatin and simvastatin, respectively. Under the above conditions the retention times for the carboxylic acid formed and the lactone substrate were as follows: 4.5/6.4 min (mevastatin), 4.4/5.6 min (lovastatin) and 5.4/7.7 min (simvastatin), respectively. Response factors for the acid products were calculated from the peak heights after complete alkaline hydrolysis of the lactones in 0.02 M NAOH for 2–24 hours at 25° C.

EXAMPLE 3

Purification and Characterization of Rabbit Serum PON3

A. Purification of Rabbit Serum PON3

Rabbit Serum PON3 was purified using a modified version of previously developed procedure (Kuo and La Du, et al., supra; Gan et al., supra). Both PON1 and PON3 are present in Rabbit serum and arylesterase activity (phenyl acetate hydrolysis) and statinase activity (lovastatin hydrolysis) were both monitored to localize PON1 and PON3, respectively, in the column chromatographic fractions.

Rabbit serum was mixed batchwise with the affinity resin Cibacron Blue 3 GA agarose, in 3M NaCl, 50 mM Tris/HCl pH8.0, 1 mM $CaCl_2$ and 5 µM EDTA. The mixture was poured into a column and washed with the above buffer until the A280 is below 0.3. The column was washed (and the protein eluted) with two column volumes of 25 mM Tris/HCl pH8, 1 mM $CaCl_2$, 20% glycerol and 0.1% sodium deoxycholate. This step preferentially binds HDL-associated protein over serum albumin and therefore removes a major portion of the unwanted proteins. Fractions containing PON3 (as determined by enzymatic activity or western blot) were pooled and applied to a DEAE Bio Gel anion exchange column equilibrated with 25 mM Tris/HCl pH8, 1 mM $CaCl_2$, 20% glycerol and 0.2% tergitol. The column was developed with a linear NaCl gradient (0–175 mM). Fractions containing the PON3 were pooled and re-chromatographed on the DEAE column as above. The DEAE column removes many of the other contaminating proteins including Apolipoprotein AI. Fractions containing PON3 were pooled, concentrated 10-fold (for example using a Centricon 10) and applied to a Sephacryl 200 gel column and eluted with 25 mM Tris/HCl pH8, 1 mM CaCl$_2$, 20% glycerol and 0.2% tergitol. PON3 fractions are pooled and run through a Concanavalin A Sepharose 4B column. PON3 does not bind to the column, while other contaminants do. PON3 was eluted with 25 mM Tris/HCl pH 7.2 and 1 mM CaCl$_2$, then washed in a Centricon with 25 mM Tris/HCl pH8, 1 mM CaCl$_2$, 20% glycerol and 0.2% tergitol to remove residual Concanavalin A fragments.

The PON1 and PON3 associated activities co-eluted in the first step, but were almost completely separated on the DEAE anion exchange column. PON 1 was purified further by pooling the fractions with highest arylesterase activity from a second DEAE column, followed by a Concanavalin A column, eluted with a 0–200 mM α-D-mannopyranoside gradient in 25 mM Tris/HCl buffer (PH 7.2), 1 mM CaCl$_2$. Finally, the PON1 preparation was washed with TCGT buffer using a 50 kDa cutoff centricon ultrafiltration unit to adjust the buffer and to remove residual Concanavalin A fragments.

Figure 3:
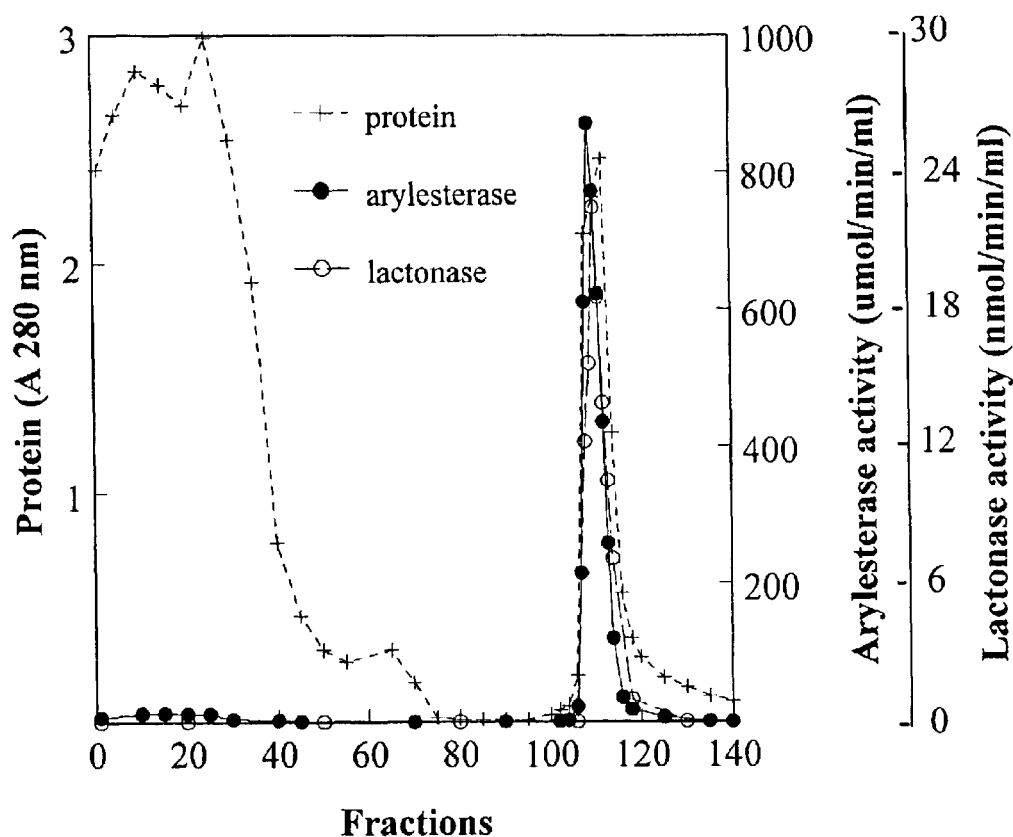
FIG. 3 shows lovastatinase and arylesterase activity of partially pure PON3 used in some embodiments of the present invention following one purification step.
Figure 4:
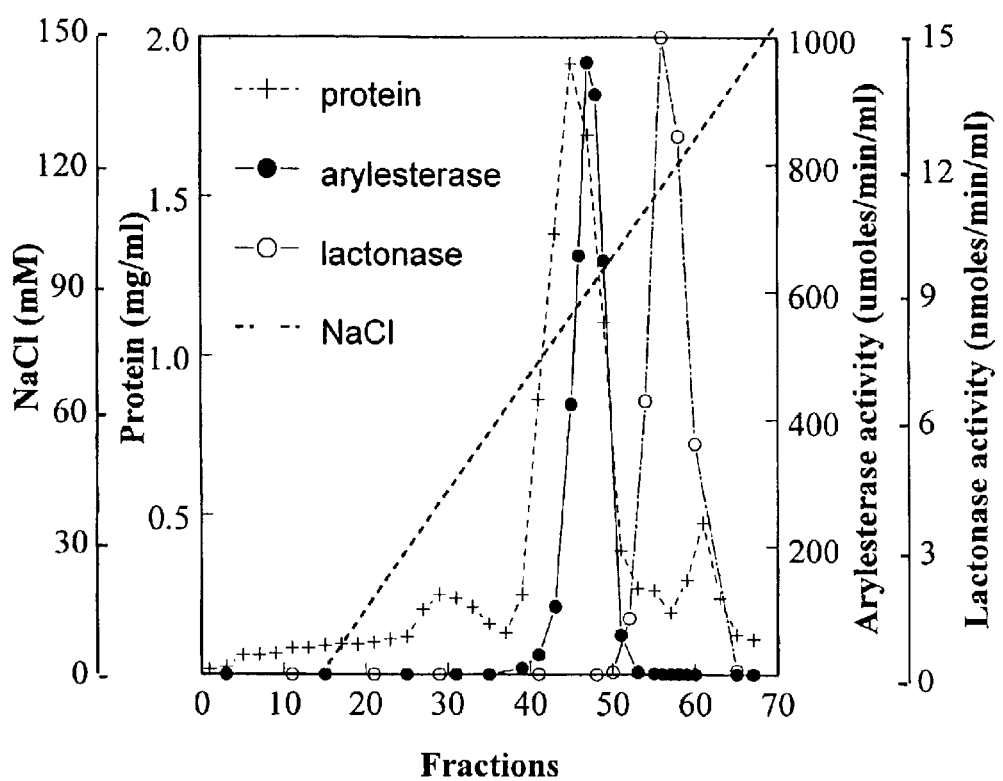
FIG. 4 shows lovastatinase and arylesterase activity of partially pure PON3 used in some embodiments of the present invention following several purification steps.

The results of the purification are shown in Table 3. The Table lists the yield and fold purification at each step in the purification. The specific activity given is based on lovastatin activity. The purification had a 1% yield of a 302 fold purified activity. FIG. 3 shows lovastatinase and arylesterase activity after the first purification step. The two activities co-eluted after this step. FIG. 4 shows the activities after the 1st DEAE anion exchange column. The activities are separated by this step. This Example demonstrated the purification of PON3 by following its statinase activity during purification.

The resolved N-terminal sequences are shown in Table 4. The N-terminus of the 40 kDa protein is identical with the deduced amino acid sequence of the cloned rabbit PON3 cDNA, and 96% identical with the sequence of microsomal rabbit PON (msPON; Ozols, Biochem J, 338:265–272 [1999]).

The N-terminus of the 50 kDa protein is 73% identical with the deduced sequence (residues 22–36) of the human platelet activated factor acetyl hydrolase (PAF-AH) precursor (Tjoelker, et al., Nature, 374:549–553 [1995]). The N-terminal amino acid of the purified human PAF-AH has an isolecine at position 42 and the estimated size of the enzyme on SDS-PAGE was 44–45 kDa (Tjoelker, et al., Nature, 374:549–553 [1995]). Thus, 20 additional amino acids in the rabbit analogue of PAF-AH would explain the observed difference in the molecular mass.

The N-terminus of the 63 kDa protein is 93% identical with the both human VNNI (Granjeaud, et al., Immunogenetics, 49:964–972 [1999]) and mouse vanin 1 (Aurrand-Lioons et al., Immunity, 5:391–405 [1996]). Both PAF-AH and vanin proteins are N-glycosylated (Tjoelker, et al., Nature, 374:549–553 [1995]; Granjeaud, et al., Immunogenetics, 49:964–972 [1999]) and retained by a Concanavalin A column used as a final step in the purification of PON3.

This Example demonstrates that the purified statinase activity is PON3. The identity of several contaminating proteins is also described.

TABLE 3

Purification of Rabbit Serum PON3

|  | Volume (ml) | Protein (mg) | Activity (nmol/min) | S.A. (nmol/min/mg) | % Yield | Fold Purification |
|---|---|---|---|---|---|---|
| Serum | 155 | 7000 | 2294 | 0.33 | 100 | 1 |
| BA | 72 | 108 | 835 | 7.8 | 37 | 24 |
| DEAE 1 | 40 | 10 | 326 | 32.6 | 14 | 99 |
| DEAE 2 | 21 | 7.1 | 321 | 45.8 | 14 | 139 |
| GFC | 5.8 | 0.75 | 92 | 125.8 | 4 | 382 |
| ConA | 6 | 0.24 | 31 | 130.0 | 1.4 | 395 |

B. Protein Concentration Assay

Protein concentrations were determined by its UV-absorption at 280 nm or, in samples containing Tergitol NP-10, by using the BCA protein assay according to the manufacturer's protocol (Pierce).

C. SDS PAGE

Figure 5:
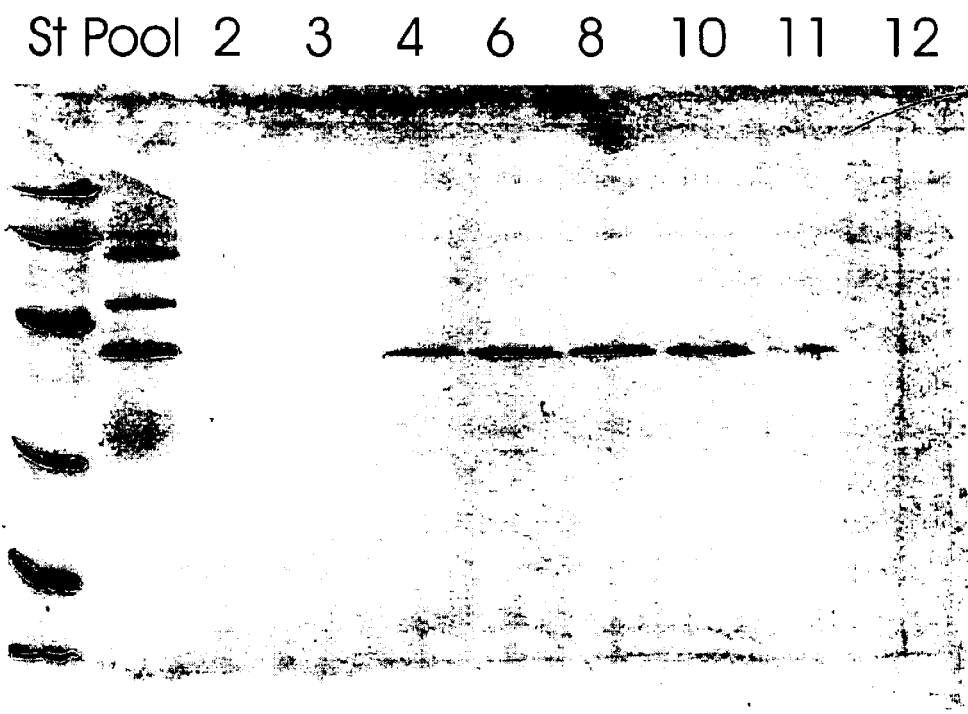
FIG. 5 shows an SDS-PAGE gel of purified rabbit serum PON3 used in some embodiments of the present invention.

SDS-PAGE was performed as previously described (Laemmli, Nature, 227:680–685, [1970]). Proteins were visualized with Coomassie Blue. FIG. 5 shows an SDS-PAGE gel of the final concavalin A purification step. Lane 1 shows molecular weight markers. Lane two shows the pooled fractions from the previous Sephacryl 200 gel filtration column. Lane 3–5 show fractions from the concavalin a column. The 40 kDa band is PON3. Two other band, at 50 kDa and 63 kDa, copurified with PON3 activity throughout the purification.

D. Protein Sequencing

PON3 and the two contaminating proteins were transferred to PVDF membrane by Western blotting and submitted for N-terminal sequencing. The N-terminal peptide sequencing was performed at the University of Michigan Protein Sequencing Core Laboratory using the Model 494 HT Protein Sequencer (Applied Biosystems).

TABLE 4

N-Terminal Sequence of PON3 Purified from Rabbit Serum

| Molecular Mass | Sequence | Protein |
|---|---|---|
| 40 kDa | AKLLLLTLLGASLAFVGERLLAFRRN (SEQ ID NO:19) | PON3 |
| 50 kDa | LDWQDVNPVAHIKSS (SEQ ID NO:20) | PAF-AH |
| 63 kDa | XDTFIAAVYEHAVILP (SEQ ID NO:21) | Vanin - 1 |

EXAMPLE 4

Association of PON3 with HDLs

This Example demonstrates the association of PON3 with HDLs. Rabbit serum lipoproteins were separated by both gel filtration and ultracentrifugation. The presence of PON1 and PON3 in the various lipoprotein fractions was monitored by statinase activity (PON3) or arylesterase and paraoxonase activity (PON1).

A. Separation of Rabbit Serum Lipoproteins by Gel Filtration

Serum was loaded onto a Biogel-A15 column (36×1.8 cm) and eluted with 50 mM Tris HCl (pH 8.0), 1 MM $CaCl_2$. Fractions were collected and analyzed on a Hitachi 912 autoanalyzer (Roche) for total cholesterol and phospholipids using commercially available kits from Wako Chemicals USA. Fractions constituting each lipoprotein peak were combined, concentrated and analyzed by a high performance gel filtration (HPGC) to determine the lipoprotein cholesterol distribution as described elsewhere (Kieft et al., J Lipid Res, 32:859–866 [1991]).

B. Lipoprotein Separation by Ultracentrifugation of Serum

Fractions were prepared by sequentially floating up the very low density-intermediate density lipoproteins (VLDL-IDL), LDL and HDL classes based on their densities (Hatch, Adv. Lipid Res., 6:1 [1968]). The fractions were dialyzed against phosphate buffered saline containing 1 mM $CaCl_2$ at 4° C. in the dark for 24 hr, then kept at 40° C. in the dark until analysis. Aliquots were analyzed by high performance gel filtration (HPGC) to confirm identity and determine purity as described (Kieft et al., J Lipid Res, 32:859–866 [1991]).

C. Association of PON Proteins with HDLs

The presence of PON1 or PON3 was assayed using by statinase activity (PON3) or arylesterase and paraoxonase activity (PON1) as described in Example 2. The majority of both the PON3 and PON1 associated activities are associated with the HDL fraction.

FIG. 6 shows the results of the gel filtration experiment described in section A above. The figure shows distribution of arylesterase (with phenyl acetate) and statinase (with lovastatin) activities, total cholesterol, and phospholipids in the gel filtration fractions. FIG. 6 indicates that Paraoxonase activities co-elute with the total cholesterol.

FIG. 7 (data is summarized in Table 5) shows chromatograms of lipoprotein cholesterol distribution (solid line) of combined and concentrated fractions constituting each lipoprotein or activity peak (numbers are indicated in the left upper corner. The mean retention times of the lipoprotein cholesterol from a reference rabbit serum (shown with dashed line on each panel) were 8.4 min, 16 min and 20.5 min for the VLDL, LDL, and HDL fraction, respectively. Fraction 37–51 contained the majority of the HDL. These fractions also correspond to the peak of the arylesterase and statinase activities (FIG. 6), indicating that the paraoxonase activities are associated with the HDL fraction.

TABLE 5

Association of PON3 and PON1 activity with HDL

|  | Serum | VLDL | LDL | HDL |
|---|---|---|---|---|
| Density g/ml | 1.006 | <1.019 | 1.019–1.063 | 1.063–1.210 |
| Arylesterase |  |  |  |  |
| Total activity (μmol/min) | 17,600 | 3.3 | 6.7 | 2,200 |
| Specific activity (μmol/min/mg) | 14.2 | 0.63 | 11.2 | 382 |
| Recovery (%) | 100 | 0.02 | 0.04 | 13 |
| Paraoxonase |  |  |  |  |
| Total activity (nmol/min) | 47,000 | 7.5 | 17.5 | 6,450 |
| Specific activity (nmol/min/mg) | 38 | 3.6 | 29.4 | 1,120 |
| Recovery (%) | 100 | 0.02 | 0.04 | 14 |
| Lactonase |  |  |  |  |
| Total activity (nmol/min) | 408 | 0 | 0.6 | 89 |
| Specific activity (nmol/min/mg) | 0.33 | 0 | 1 | 15.5 |
| Recovery (%) | 100 | 0 | 0.14 | 22 |
| HPGC profile |  |  |  |  |

EXAMPLE 5

PON3 Protects LDLs Against Lipid Peroxidation

LDL were isolated by ultracentrifugation as described above (Example 4). LDL oxidation was induced by the incubation of the lipoprotein (0.1 mg protein/ml) with 2–10 μM $CuSO_4$ in the air, in the absence or presence of PON3 or PON1, for up to 5 h at 37° C. The kinetics of lipoprotein oxidation was followed by monitoring the conjugated dienes formation at 234 nm (Esterbauer et al., Free Radical Res Commun, 6:67–75 [1989]) using a quartz microtiter plate in a SPECTRAmax 190 plate reader (Molecular Devices). Lipoprotein oxidation was also determined by the lipid peroxides test, which analyzes lipid peroxides by their capacity to convert iodide to iodine, as measured photometrically at 365 nm (El-Saadani et al., J Lipid Res, 30:627–630 [1989]).

Results are shown in FIG. 8 (diene formation) and FIG. 9 (lipid peroxides). PON3 was significantly better at inhibiting both conjugated diene and lipid peroxide formation than PON1. In fact, PON3 was more than 50 times more potent per μg protein at protecting LDL against copper-induced oxidation compared to PON1.

EXAMPLE 6

Expression of rPON3 in Mammalian Cells

This example describes the expression of wild type rabbit PON3 and PON3 mutants in mammalian tissue culture cells. The lactonase activity of the mutants and wild type rPON3 was also investigated.

A. Cloning and Expression of Wild Type PON3

Unique restriction enzyme sites (EcoRI and XhoI) were engineered onto the two ends of the rPON3 cDNA. The rPON3 gene was cloned into EcoRI/XhoI sites of the pcDNA3.1 expression vector (Invitrogen, Carlsbad, Calif.). The resulting vector prPON3/pcDNA3.1 was transfected into human 293T cells. The cells were grown in media for 2–6 days. rPON3 was expressed in the media.

B. Site Directed Mutagenesis

Mutations were made within the PON3 sequence to identify enzymatic and structurally important residues. Two primers (one in the forward orientation and one in the reverse) with the desired mutation incorporated into their sequence were used in separate PCR reactions using primers in the 5'- or 3'-untranslated region. The resulting fragments were purified and combined. A PCR reaction using the two external primers was then carried out on the mixture. The generated product is a full-length PON3 sequence containing the desired mutation. The PCR product was cloned into pcDNA3.1 as described above, and sequenced. The mutant clones were expressed in 293T cells and analyzed. Four site-directed single amino acid change mutations were generated (N169D [SEQ ID NO:10; FIG. 13]; K243H [SEQ ID NO:12; FIG. 14]; L281W [SEQ ID NO:14; FIG. 15]; and D324N [SEQ ID NO:16; FIG. 16]). In addition, a truncation mutant (E46K [SEQ ID NO:18; FIG. 17]) was generated.

C. Expression of wt and Mutant rPON3

Figure 10:
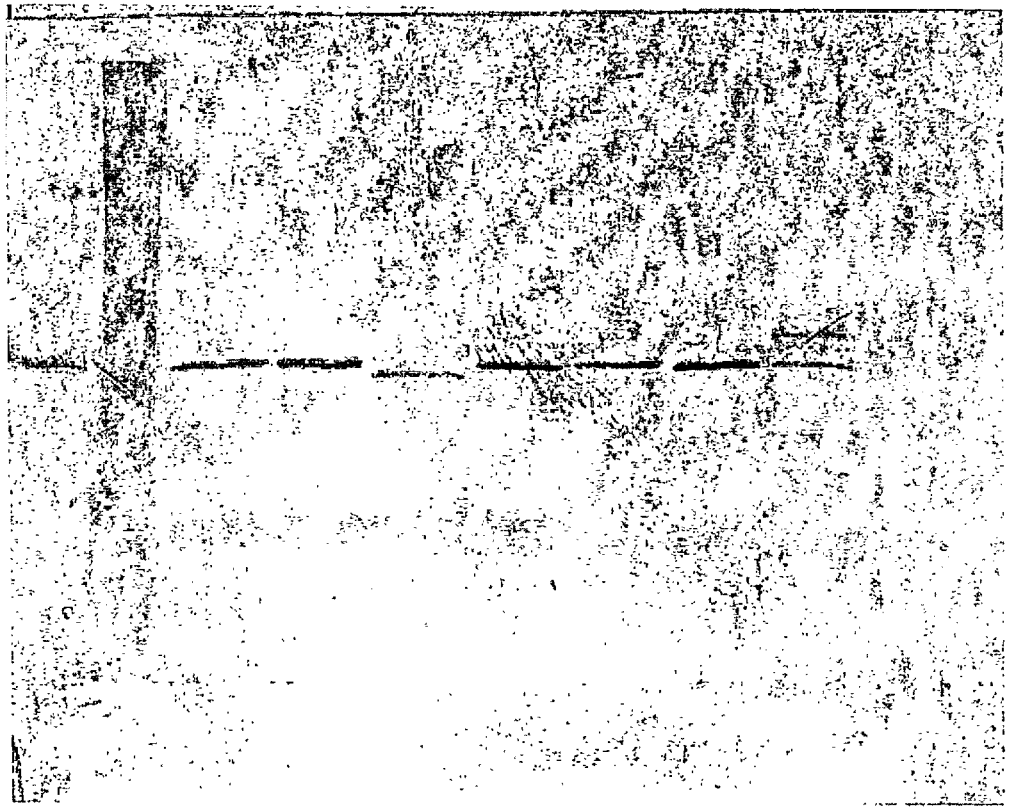
FIG. 10 shows a photograph of a western blot of wild type and mutant PON3 used in some embodiments of the present invention expressed in mammalian cells.

The clones containing wt and mutant rPON3 were transfected into 293T cells. Expression media from the cells was concentrated and run on a SDS-PAGE gel. The proteins were transferred to a membrane and probed with a cross-reactive (human PON1) antibody. A photograph of the western blot is shown in FIG. 10. The wild type PON3 and all mutants were shown to be expressed. Mutant E46K runs slightly smaller than anticipated due to an inadvertent second mutation in the clone that causes a truncation of the protein at amino acid 320. Mutant D324N appears to be glycosylated, unlike the PON3 wild type or other mutants. D324N is a site shown to be glycosylated in other PON proteins.

D. Lactonase Activity

Figure 11:
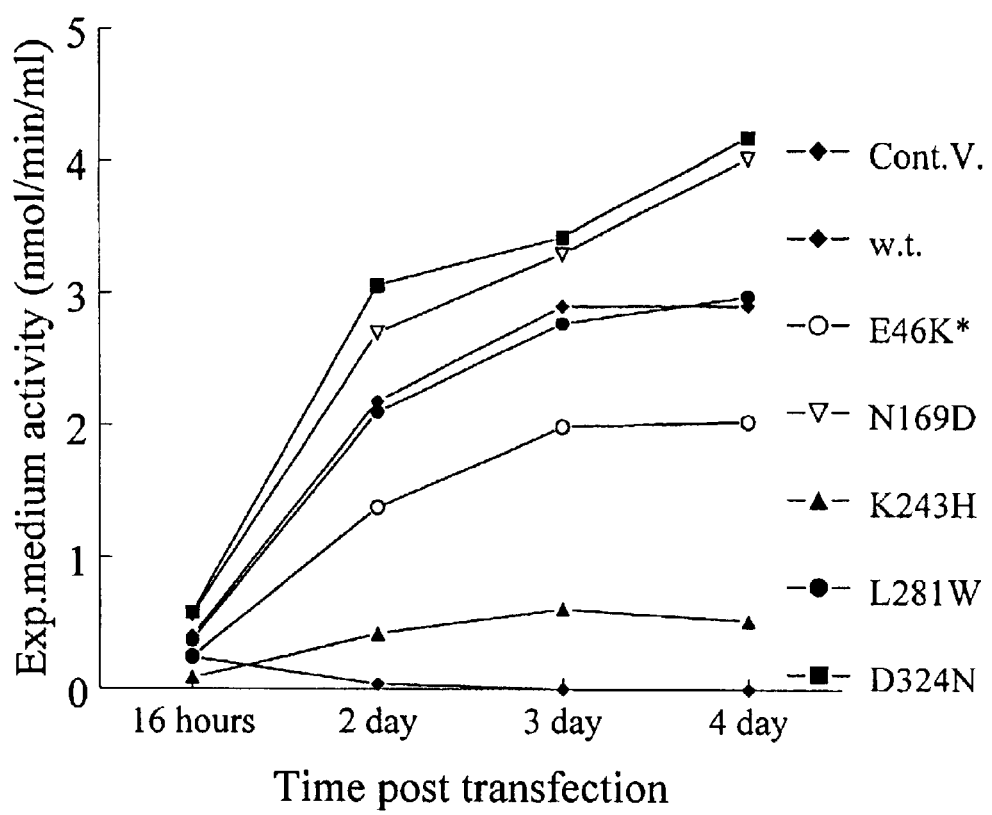
FIG. 11 shows the ability of wild type and mutant rPON3 used in some embodiments of the present invention expressed in mammalian cells to hydrolyze the lactone Lovastatin for up to 4 days post transfection.

Expression media from the transient transfection of mutant clones into 293T cells was analyzed for activity towards the lactone Lovastatin up to 4 days post transfection. Results are shown in FIG. 11. The results indicate that all mutants have some lactonase activity.

Figure 12:
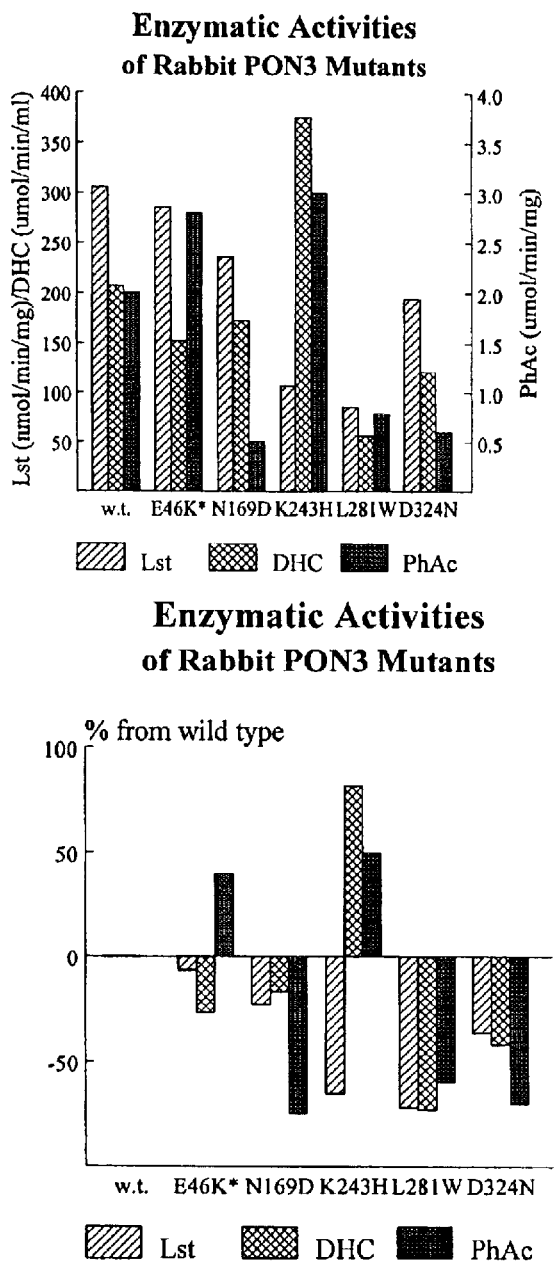
FIG. 12 shows the specific activity of the wild type and mutant rPON3 polypeptides used in some embodiments of the present invention for the hydrolysis of the lactone Lovastatin.

Specific activities were calculated based on quantitation of the western blot in FIG. 10. Results are shown in FIG. 12. Mutants K243H and L281W appear to have about ⅓ the specific activity compared to the wild type, while the remaining mutants have at least 75% of the specific activity of the wild type. Mutant E46K is missing 25 amino acids from the C-terminus, yet retains lactonase activity. This mutation removes the third cysteine residue thought to be part of the disulfide bond.

EXAMPLE 7

Expression of PON3 in Bacteria

This Example describes the expression of rabbit PON3 protein in bacteria. The endogenous NcoI site at the translation start site, and an engineered XhoI site in the 3' UTR were used to clone the rPON3 cDNA into the bacterial expression vector pET24d+. The resulting vector (prPON3/pET24d) was transformed into bacterial BL21(DE3) cells. LB broth supplemented with 30 mg/ml Kanamycin was inoculated with a single colony and the bacteria were grown at 37° C. When the culture reached an OD600 of 0.7, IPTG (1 mM) was added and growth continued. Samples of the culture were taken at the time of induction and 1, 2, 4, and 16 hours post-induction. Samples were electrophoresed through a 10% SDS-PAGE gel and Western blotted with a human PON1 antibody. An inducible, 40 kDa band was visible in the 1, 2, 4, and 16 time point lanes that aligned with a rPON3 standard. The samples were also assayed and found to have 257, 8663, 6178, 5872, and 8436 U/ml statinase activity for time points 0, 1, 2, 4, and 16 respectively.

All publications and patents mentioned in the above specification are herein incorporated by reference. Various modifications and variations of the described compositions and methods of the invention will be apparent to those skilled in the art without departing from the scope and spirit of the invention. Although the invention has been described in connection with specific preferred embodiments, it should be understood that the invention should not be unduly limited to such specific embodiments. Indeed, various modifications of the described modes for carrying out the invention which are obvious to those skilled in medicine, pharmacology, histology, diagnostics, and molecular biology or related fields are intended to be within the scope of the following claims.

What is claimed is:

1. A method for providing a paraoxonase-3 polypeptide to a subject, comprising:
   a) providing:
      i) a biologically active rabbit paraoxonase-3 polypeptide or polypeptide fragment thereof, wherein said paraoxonase-3 polypeptide has the amino acid sequence of SEQ ID NQ:8, and wherein said polypeptide fragment is a fragment of SEQ ID NO:8, and wherein said fragment has paraoxonase activity;
      ii) a subject; and
      iii) a delivery system;
   b) administering said biologically active rabbit paraoxonase-3 polypeptide or fragment thereof to said subject using said delivery system.

2. The method of claim 1, wherein said subject comprises a subject suspected of having sepsis.

3. The method of claim 1, wherein said subject comprises a subject which is susceptible to sepsis.

4. The method of claim 1, wherein said subject comprises a subject suspected of having oxidative damage, wherein said oxidative damage is atherosclerosis.

5. The method of claim 1, wherein said subject comprises a subject which is susceptible to atherosclerosis.

6. The method of claim 1, wherein said subject comprises a subject suspected of having been exposed to toxic chemicals.

7. The method of claim 1, wherein said subject comprises a subject which is susceptible to damage by toxic chemicals.

* * * * *

SEQUENCE LISTING

<160> NUMBER OF SEQ ID NOS: 34

<210> SEQ ID NO 1
<211> LENGTH: 28
<212> TYPE: DNA
<213> ORGANISM: Artificial Sequence
<220> FEATURE:
<223> OTHER INFORMATION: Synthetic

<400> SEQUENCE: 1
ggcatagaac tgttctggtc caagaacc                28

<210> SEQ ID NO 2
<211> LENGTH: 34
<212> TYPE: DNA
<213> ORGANISM: Artificial Sequence
<220> FEATURE:
<223> OTHER INFORMATION: Synthetic

<400> SEQUENCE: 2
gcttctgaag atattgatat actccccagt gggc         34

<210> SEQ ID NO 3
<211> LENGTH: 21
<212> TYPE: DNA
<213> ORGANISM: Artificial Sequence
<220> FEATURE:
<223> OTHER INFORMATION: Synthetic

<400> SEQUENCE: 3
ctcatctggt gcaaagtttg g         21

<210> SEQ ID NO 4
<211> LENGTH: 20
<212> TYPE: DNA
<213> ORGANISM: Artificial Sequence
<220> FEATURE:
<223> OTHER INFORMATION: Synthetic

<400> SEQUENCE: 4
acaacaacgc tctcttgtac         20

<210> SEQ ID NO 5
<211> LENGTH: 27
<212> TYPE: DNA
<213> ORGANISM: Artificial Sequence
<220> FEATURE:
<223> OTHER INFORMATION: Synthetic

<400> SEQUENCE: 5
atcggaattc catggcgaag ctcctgc         27

<210> SEQ ID NO 6
<211> LENGTH: 26
<212> TYPE: DNA
<213> ORGANISM: Artificial Sequence
<220> FEATURE:
<223> OTHER INFORMATION: Synthetic

<400> SEQUENCE: 6
aggcctcgag ctggagacta gagcac         26

<210> SEQ ID NO 7
<211> LENGTH: 1191
<212> TYPE: DNA
<213> ORGANISM: Oryctolagus cuniculus
<220> FEATURE:
<221> NAME/KEY: misc_feature
<222> LOCATION: (5)..(5)
<223> OTHER INFORMATION: The n at this position can be a, c, t, or g.
<220> FEATURE:
<221> NAME/KEY: misc_feature
<222> LOCATION: (9)..(9)
<223> OTHER INFORMATION: The n at this position can be a, c, t, or g.

<400> SEQUENCE: 7
ttgtntgtng ccacctggct cgccgggacc atggcgaagc tcctgctgct gaccctgctg         60
ggggccagcc tcgccttcgt cggggagagg ttgctggcgt ttagaaacag ctttggtgca        120
gttcaagaac tggagccagt agaacccag aactgtgtcc ttattgaggg actcgaaaat        180
ggctcggaag atattgatat acttcctagt gggctggctt ttatctccag tggattaaaa        240
tatccaggca tgccaaactt tgcaccagat gagccaggaa aaatcttctt gatagatatg        300

-continued

```
aatgagaaga acccaagagc acaagagctg gaaatcagca atggatttga aaaagaatca    360
ttcaatccac atgggatcag cactttcatt gataaagacc atactgtgta tctttatgtt    420
gtgaatcatc cccacatgaa gtctactgtg agatatttta aatttgagga acaacaacgc    480
tctcttgtac acctgaaaac tataaaacat gaacttctca agagtgtgaa taacattgtg    540
gttcttggac cggaacagtt ctacgccacc agagaccact attttaccaa ctatgtctta    600
gcacttcttg agatgttttt ggatcttcac tggacttccg ttcttttcta cagccccaaa    660
gaggtcaaag tggtggccaa aggattcagt tctgccaatg ggatcacagt ctcactagat    720
aagaagtatg tctatgttgc tgatgccaca gctaagaatg tgcatgtaat ggaaaaacat    780
gacaactggg atttaactga actgaaggta atacacttgg acaccttagt ggataatttg    840
tctgttgatc ctgccacggg agatatcttg gcaggatgcc atcctaatgg catgaagctt    900
ctgaactata accctgagga tcctccagga tcagaagtac ttcgtatcca gaatgttttg    960
tctgagaagc ccagggtgag caccgtgtac accaatgacg ctctgtgct tcagggctcc    1020
accgtggctt ctgtgtacca agggaagatt ctcataggca ctatatttca caaaactctg    1080
tattgtgtgc tctagtctcc agctcttcca aaaagtctac ctgtttggta aaagtaaatc    1140
tttaaaggtg tgataattgg aaccataagt aaataacaaa taccaacaaa a             1191
```

<210> SEQ ID NO 8
<211> LENGTH: 354
<212> TYPE: PRT
<213> ORGANISM: Oryctolagus cuniculus

<400> SEQUENCE: 8

```
Met Ala Lys Leu Leu Leu Thr Leu Leu Gly Ala Ser Leu Ala Phe
1               5                   10                  15

Val Gly Glu Arg Leu Leu Ala Phe Arg Asn Ser Phe Gly Ala Val Gln
            20                  25                  30

Glu Leu Glu Pro Val Glu Pro Gln Asn Cys Val Leu Ile Glu Gly Leu
        35                  40                  45

Glu Asn Gly Ser Glu Asp Ile Asp Ile Leu Pro Ser Gly Leu Ala Phe
    50                  55                  60

Ile Ser Ser Gly Leu Lys Tyr Pro Gly Met Pro Asn Phe Ala Pro Asp
65                  70                  75                  80

Glu Pro Gly Lys Ile Phe Leu Ile Asp Met Asn Glu Lys Asn Pro Arg
                85                  90                  95

Ala Gln Glu Leu Glu Ile Ser Asn Gly Phe Glu Lys Glu Ser Phe Asn
            100                 105                 110

Pro His Gly Ile Ser Thr Phe Ile Asp Lys Asp His Thr Val Tyr Leu
        115                 120                 125

Tyr Val Val Asn His Pro His Met Lys Ser Thr Val Glu Ile Phe Lys
    130                 135                 140

Phe Glu Glu Gln Gln Arg Ser Leu Val His Leu Lys Thr Ile Lys His
145                 150                 155                 160

Glu Leu Leu Lys Ser Val Asn Asn Ile Val Val Leu Gly Pro Glu Gln
                165                 170                 175

Phe Tyr Ala Thr Arg Asp His Tyr Phe Thr Asn Tyr Val Leu Ala Leu
            180                 185                 190

Leu Glu Met Phe Leu Asp Leu His Trp Thr Ser Val Leu Phe Tyr Ser
        195                 200                 205

Pro Lys Glu Val Lys Val Val Ala Lys Gly Phe Ser Ser Ala Asn Gly
    210                 215                 220
```

Ile Thr Val Ser Leu Asp Lys Lys Tyr Val Tyr Val Ala Asp Ala Thr
225                 230                 235                 240

Ala Lys Asn Val His Val Met Glu Lys His Asp Asn Trp Asp Leu Thr
            245                 250                 255

Glu Leu Lys Val Ile His Leu Asp Thr Leu Val Asp Asn Leu Ser Val
        260                 265                 270

Asp Pro Ala Thr Gly Asp Ile Leu Ala Gly Cys His Pro Asn Gly Met
    275                 280                 285

Lys Leu Leu Asn Tyr Asn Pro Glu Asp Pro Pro Gly Ser Glu Val Leu
    290                 295                 300

Arg Ile Gln Asn Val Leu Ser Glu Lys Pro Arg Val Ser Thr Val Tyr
305                 310                 315                 320

Thr Asn Asp Gly Ser Val Leu Gln Gly Ser Thr Val Ala Ser Val Tyr
                325                 330                 335

Gln Gly Lys Ile Leu Ile Gly Thr Ile Phe His Lys Thr Leu Tyr Cys
            340                 345                 350

Val Leu

<210> SEQ ID NO 9
<211> LENGTH: 1161
<212> TYPE: DNA
<213> ORGANISM: Oryctolagus cuniculus

<400> SEQUENCE: 9
atggcgaagc tcctgctgct gaccctgctg ggggccagcc tcgccttcgt cggggagagg      60
ttgctggcgt ttagaaacag ctttggtgca gttcaagaac tggagccagt agaaccccag     120
aactgtgtcc ttattgaggg actcgaaaat ggctcggaag atattgatat acttcctagt     180
gggctggctt ttatctccag tggattaaaa tatccaggca tgccaaactt tgcaccagat     240
gagccaggaa aaatcttctt gatagatatg aatgagaaga acccaagagc acaagagctg     300
gaaatcagca tggatttgaa aaagaatca ttcaatccac atgggatcag cactttcatt      360
gataaagacc atactgtgta tctttatgtt gtgaatcatc cccacatgaa gtctactgtg     420
gagatattta aatttgagga caacaacgc tctcttgtac acctgaaaac tataaaacat      480
gaacttctca gagtgtgaa tgacattgtg gttcttggac cggaacagtt ctacgccacc      540
agagaccact attttaccaa ctatgtctta gcacttcttg agatgttttt ggatcttcac     600
tggacttccg ttcttttcta cagccccaaa gaggtcaaag tggtggccaa aggattcagt     660
tctgccaatg ggatcacagt ctcactagat aagaagtatg tctatgttgc tgatgccaca     720
gctaagaatg tgcatgtaat ggaaaaacat gacaactggg atttaactga actgaaggta     780
atacacttgg acaccttagt ggataatttg tctgttgatc ctgccacggg agatatcttg     840
gcaggatgcc atcctaatgg catgaagctt ctgaactata cctgagga tcctccagga      900 tcagaagtac ttcgtatcca gaatgttttg tctgagaagc ccagggtgag caccgtgtac     960
accaatgacg gctctgtgct tcagggctcc accgtggctt ctgtgtacca agggaagatt    1020
ctcataggca ctatatttca caaaactctg tattgtgtgc tctagtctcc agctcttcca    1080
aaaagtctac ctgtttggta aaagtaaatc tttaaaggtg tgataattgg aaccataagt    1140
aaataacaaa taccaacaaa a                                              1161

<210> SEQ ID NO 10
<211> LENGTH: 353
<212> TYPE: PRT

<213> ORGANISM: Oryctolagus cuniculus

<400> SEQUENCE: 10

```
Met Ala Lys Leu Leu Leu Thr Leu Leu Gly Ala Ser Leu Ala Phe
1               5                   10                  15

Val Gly Glu Arg Leu Leu Ala Phe Arg Asn Ser Phe Gly Ala Val Gln
                20                  25                  30

Glu Leu Glu Pro Val Glu Pro Gln Asn Cys Val Leu Ile Glu Gly Leu
            35                  40                  45

Glu Asn Gly Ser Glu Asp Ile Asp Ile Leu Pro Ser Gly Leu Ala Phe
    50                  55                  60

Ile Ser Ser Gly Leu Lys Tyr Pro Gly Met Pro Asn Phe Ala Pro Asp
65                  70                  75                  80

Glu Pro Gly Lys Ile Phe Leu Ile Asp Met Asn Glu Lys Asn Pro Arg
                85                  90                  95

Ala Gln Glu Leu Glu Ile Ser Asn Gly Phe Glu Lys Glu Ser Phe Asn
            100                 105                 110

Pro His Gly Ile Ser Thr Phe Ile Asp Lys Asp His Thr Val Tyr Leu
        115                 120                 125

Tyr Val Val Asn His Pro His Met Lys Ser Thr Val Glu Ile Phe Lys
    130                 135                 140

Phe Glu Glu Gln Gln Arg Ser Leu Val His Leu Lys Thr Ile Lys His
145                 150                 155                 160

Glu Leu Leu Lys Ser Val Asn Asp Val Val Leu Gly Pro Glu Gln Phe
                165                 170                 175

Tyr Ala Thr Arg Asp His Tyr Phe Thr Asn Tyr Val Leu Ala Leu Leu
            180                 185                 190

Glu Met Phe Leu Asp Leu His Trp Thr Ser Val Leu Phe Tyr Ser Pro
        195                 200                 205

Lys Glu Val Lys Val Ala Lys Gly Phe Ser Ser Ala Asn Gly Ile
    210                 215                 220

Thr Val Ser Leu Asp Lys Lys Tyr Val Tyr Val Ala Asp Ala Thr Ala
225                 230                 235                 240

Lys Asn Val His Val Met Glu Lys His Asp Asn Trp Asp Leu Thr Glu
                245                 250                 255

Leu Lys Val Ile His Leu Asp Thr Leu Val Asp Asn Leu Ser Val Asp
            260                 265                 270

Pro Ala Thr Gly Asp Ile Leu Ala Gly Cys His Pro Asn Gly Met Lys
        275                 280                 285

Leu Leu Asn Tyr Asn Pro Glu Asp Pro Pro Gly Ser Glu Val Leu Arg
    290                 295                 300

Ile Gln Asn Val Leu Ser Glu Lys Pro Arg Val Ser Thr Val Tyr Thr
305                 310                 315                 320

Asn Asp Gly Ser Val Leu Gln Gly Ser Thr Val Ala Ser Val Tyr Gln
                325                 330                 335

Gly Lys Ile Leu Ile Gly Thr Ile Phe His Lys Thr Leu Tyr Cys Val
            340                 345                 350

Leu
```

<210> SEQ ID NO 11
<211> LENGTH: 1161
<212> TYPE: DNA
<213> ORGANISM: Oryctolagus cuniculus

<400> SEQUENCE: 11

```
atggcgaagc tcctgctgct gaccctgctg ggggccagcc tcgccttcgt cggggagagg      60
ttgctggcgt ttagaaacag ctttggtgca gttcaagaac tggagccagt agaaccccag     120
aactgtgtcc ttattgaggg actcgaaaat ggctcggaag atattgatat acttcctagt     180
gggctggctt ttatctccag tggattaaaa tatccaggca tgccaaactt tgcaccagat     240
gagccaggaa aaatcttctt gatagatatg aatgagaaga acccaagagc acaagagctg     300
gaaatcagca atggatttga aaagaatca ttcaatccac atgggatcag cactttcatt     360
gataaagacc atactgtgta tctttatgtt gtgaatcatc cccacatgaa gtctactgtg     420
gagatattta aatttgagga caacaacgc tctcttgtac acctgaaaac tataaaacat     480
gaacttctca agagtgtgaa taacattgtg gttcttggac cggaacagtt ctacgccacc     540
agagaccact attttaccaa ctatgtctta gcacttcttg agatgttttt ggatcttcac     600
tggacttccg ttctttcta cagccccaaa gaggtcaaag tggtggccaa aggattcagt     660
tctgccaatg ggatcacagt ctcactagat aagaagtatg tctatgttgc tgatgccaca     720
gctaagaatg tgcatgtaat ggaaaaacat gacaactggg atttaactga actgcacgta     780
atacacttgg acaccttagt ggataatttg tctgttgatc ctgccacggg agatatcttg     840
gcaggatgcc atcctaatgg catgaagctt ctgaactata accctgagga tcctccagga     900
tcagaagtac ttcgtatcca gaatgttttg tctgagaagc ccagggtgag caccgtgtac     960
accaatgacg ctctgtgct caggctcc accgtggctt ctgtgtacca agggaagatt    1020
ctcataggca ctatatttca caaactctg tattgtgtgc tctagtctcc agctcttcca    1080
aaaagtctac ctgtttggta aaagtaaatc tttaaaggtg tgataattgg aaccataagt    1140
aaataacaaa taccaacaaa a                                              1161
```

<210> SEQ ID NO 12
<211> LENGTH: 354
<212> TYPE: PRT
<213> ORGANISM: Oryctolagus cuniculus

<400> SEQUENCE: 12

```
Met Ala Lys Leu Leu Leu Thr Leu Leu Gly Ala Ser Leu Ala Phe
1               5                   10                  15

Val Gly Glu Arg Leu Leu Ala Phe Arg Asn Ser Phe Gly Ala Val Gln
            20                  25                  30

Glu Leu Glu Pro Val Glu Pro Gln Asn Cys Val Leu Ile Glu Gly Leu
        35                  40                  45

Glu Asn Gly Ser Glu Asp Ile Asp Ile Leu Pro Ser Gly Leu Ala Phe
    50                  55                  60

Ile Ser Ser Gly Leu Lys Tyr Pro Gly Met Pro Asn Phe Ala Pro Asp
65                  70                  75                  80

Glu Pro Gly Lys Ile Phe Leu Ile Asp Met Asn Glu Lys Asn Pro Arg
                85                  90                  95

Ala Gln Glu Leu Glu Ile Ser Asn Gly Phe Glu Lys Glu Ser Phe Asn
            100                 105                 110

Pro His Gly Ile Ser Thr Phe Ile Asp Lys Asp His Thr Val Tyr Leu
        115                 120                 125

Tyr Val Val Asn His Pro His Met Lys Ser Thr Val Glu Ile Phe Lys
    130                 135                 140

Phe Glu Glu Gln Gln Arg Ser Leu Val His Leu Lys Thr Ile Lys His
145                 150                 155                 160
```

```
Glu Leu Leu Lys Ser Val Asn Ile Val Val Leu Gly Pro Glu Gln
            165                 170                 175

Phe Tyr Ala Thr Arg Asp His Tyr Phe Thr Asn Tyr Val Leu Ala Leu
            180                 185                 190

Leu Glu Met Phe Leu Asp Leu His Trp Thr Ser Val Leu Phe Tyr Ser
            195                 200                 205

Pro Lys Glu Val Lys Val Ala Lys Gly Phe Ser Ser Ala Asn Gly
210                 215                 220

Ile Thr Val Ser Leu Asp Lys Lys Tyr Val Tyr Val Ala Asp Ala Thr
225                 230                 235                 240

Ala His Asn Val His Val Met Glu Lys His Asp Asn Trp Asp Leu Thr
            245                 250                 255

Glu Leu Lys Val Ile His Leu Asp Thr Leu Val Asp Asn Leu Ser Val
            260                 265                 270

Asp Pro Ala Thr Gly Asp Ile Leu Ala Gly Cys His Pro Asn Gly Met
            275                 280                 285

Lys Leu Leu Asn Tyr Asn Pro Glu Asp Pro Pro Gly Ser Glu Val Leu
290                 295                 300

Arg Ile Gln Asn Val Leu Ser Glu Lys Pro Arg Val Ser Thr Val Tyr
305                 310                 315                 320

Thr Asn Asp Gly Ser Val Leu Gln Gly Ser Thr Val Ala Ser Val Tyr
            325                 330                 335

Gln Gly Lys Ile Leu Ile Gly Thr Ile Phe His Lys Thr Leu Tyr Cys
            340                 345                 350

Val Leu
```

<210> SEQ ID NO 13
<211> LENGTH: 1161
<212> TYPE: DNA
<213> ORGANISM: Oryctolagus cuniculus

<400> SEQUENCE: 13

```
atggcgaagc tcctgctgct gaccctgctg ggggccagcc tcgccttcgt cggggagagg     60
ttgctggcgt ttagaaacag ctttggtgca gttcaagaac tggagccagt agaacccag    120
aactgtgtcc ttattgaggg actcgaaaat ggctcggaag atattgatat acttcctagt    180
gggctggctt ttatctccag tggattaaaa tatccaggca tgccaaactt tgcaccagat    240
gagccaggaa aaatcttctt gatagatatg aatgagaaga cccaagagc acagagctg     300
gaaatcagca atggatttga aaagaatca ttcaatccac atgggatcag cactttcatt    360
gataaagacc atactgtgta tctttatgtt gtgaatcatc cccacatgaa gtctactgtg    420
gagatattta aatttgagga caacaacgc tctcttgtac acctgaaaac tataaaacat    480
gaacttctca agagtgtgaa taacattgtg gttcttggac cggaacagtt ctacgccacc    540
agagaccact attttaccaa ctatgtctta gcacttcttg atgttttt ggatcttcac      600
tggacttccg ttcttttcta cagccccaaa gaggtcaaag tggtggccaa aggattcagt    660
tctgccaatg ggatcacagt ctcactagat aagaagtatg tctatgttgc tgatgccaca    720
gctaagaatg tgcatgtaat ggaaaaacat gacaactggg atttaactga actgaaggta    780
atacacttgg acaccttagt ggataatttg tctgttgatc ctgccacggg agatatctgg    840
gcaggatgcc atcctaatgg catgaagctt ctgaactata accctgagga tcctccagga    900
tcagaagtac ttcgtatcca gaatgttttg tctgagaagc ccagggtgag caccgtgtac    960
accaatgacg gctctgtgct tcagggctcc accgtggctt ctgtgtacca agggaagatt    1020
```

```
ctcataggca ctatatttca caaaactctg tattgtgtgc tctagtctcc agctcttcca    1080
aaaagtctac ctgtttggta aaagtaaatc tttaaggtg tgataattgg aaccataagt    1140
aaataacaaa taccaacaaa a                                              1161
```

<210> SEQ ID NO 14
<211> LENGTH: 354
<212> TYPE: PRT
<213> ORGANISM: Oryctolagus cuniculus

<400> SEQUENCE: 14

```
Met Ala Lys Leu Leu Leu Thr Leu Leu Gly Ala Ser Leu Ala Phe
1               5                   10                  15

Val Gly Glu Arg Leu Leu Ala Phe Arg Asn Ser Phe Gly Ala Val Gln
            20                  25                  30

Glu Leu Glu Pro Val Glu Pro Gln Asn Cys Val Leu Ile Glu Gly Leu
        35                  40                  45

Glu Asn Gly Ser Glu Asp Ile Asp Ile Leu Pro Ser Gly Leu Ala Phe
    50                  55                  60

Ile Ser Ser Gly Leu Lys Tyr Pro Gly Met Pro Asn Phe Ala Pro Asp
65                  70                  75                  80

Glu Pro Gly Lys Ile Phe Leu Ile Asp Met Asn Glu Lys Asn Pro Arg
                85                  90                  95

Ala Gln Glu Leu Glu Ile Ser Asn Gly Phe Glu Lys Glu Ser Phe Asn
            100                 105                 110

Pro His Gly Ile Ser Thr Phe Ile Asp Lys Asp His Thr Val Tyr Leu
        115                 120                 125

Tyr Val Val Asn His Pro His Met Lys Ser Thr Val Glu Ile Phe Lys
    130                 135                 140

Phe Glu Glu Gln Gln Arg Ser Leu Val His Leu Lys Thr Ile Lys His
145                 150                 155                 160

Glu Leu Leu Lys Ser Val Asn Asn Ile Val Val Leu Gly Pro Glu Gln
                165                 170                 175

Phe Tyr Ala Thr Arg Asp His Tyr Phe Thr Asn Tyr Val Leu Ala Leu
            180                 185                 190

Leu Glu Met Phe Leu Asp Leu His Trp Thr Ser Val Leu Phe Tyr Ser
        195                 200                 205

Pro Lys Glu Val Lys Val Val Ala Lys Gly Phe Ser Ser Ala Asn Gly
    210                 215                 220

Ile Thr Val Ser Leu Asp Lys Lys Tyr Val Tyr Val Ala Asp Ala Thr
225                 230                 235                 240

Ala Lys Asn Val His Val Met Glu Lys His Asp Asn Trp Asp Leu Thr
                245                 250                 255

Glu Leu Lys Val Ile His Leu Asp Thr Leu Val Asp Asn Leu Ser Val
            260                 265                 270

Asp Pro Ala Thr Gly Asp Ile Trp Ala Gly Cys His Pro Asn Gly Met
        275                 280                 285

Lys Leu Leu Asn Tyr Asn Pro Glu Asp Pro Pro Gly Ser Glu Val Leu
    290                 295                 300

Arg Ile Gln Asn Val Leu Ser Glu Lys Pro Arg Val Ser Thr Val Tyr
305                 310                 315                 320

Thr Asn Asp Gly Ser Val Leu Gln Gly Ser Thr Val Ala Ser Val Tyr
                325                 330                 335

Gln Gly Lys Ile Leu Ile Gly Thr Ile Phe His Lys Thr Leu Tyr Cys
```

Val Leu

<210> SEQ ID NO 15
<211> LENGTH: 1161
<212> TYPE: DNA
<213> ORGANISM: Oryctolagus cuniculus

<400> SEQUENCE: 15

| | | | | | |
|---|---|---|---|---|---|
| atggcgaagc | tcctgctgct | gaccctgctg | ggggccagcc | tcgccttcgt | cggggagagg | 60 |
| ttgctggcgt | ttagaaacag | ctttggtgca | gttcaagaac | tggagccagt | agaaccccag | 120 |
| aactgtgtcc | ttattgaggg | actcgaaaat | ggctcggaag | atattgatat | acttcctagt | 180 |
| gggctggctt | ttatctccag | tggattaaaa | tatccaggca | tgccaaactt | tgcaccagat | 240 |
| gagccaggaa | aaatcttctt | gatagatatg | aatgagaaga | acccaagagc | acaagagctg | 300 |
| gaaatcagca | atggatttga | aaagaatca | ttcaatccac | atgggatcag | cactttcatt | 360 |
| gataaagacc | atactgtgta | tctttatgtt | gtgaatcatc | cccacatgaa | gtctactgtg | 420 |
| gagatattta | aatttgagga | caacaacgc | tctcttgtac | acctgaaaac | tataaaacat | 480 |
| gaacttctca | agagtgtgaa | taacattgtg | gttcttggac | cggaacagtt | ctacgccacc | 540 |
| agagaccact | attttaccaa | ctatgtctta | gcacttcttg | agatgttttt | ggatcttcac | 600 |
| tggacttccg | ttcttttcta | cagccccaaa | gaggtcaaag | tggtggccaa | aggattcagt | 660 |
| tctgccaatg | ggatcacagt | ctcactagat | aagaagtatg | tctatgttgc | tgatgccaca | 720 |
| gctaagaatg | tgcatgtaat | ggaaaaacat | gacaactggg | atttaactga | actgaaggta | 780 |
| atacacttgg | acaccttagt | ggataatttg | tctgttgatc | ctgccacggg | agatatcttg | 840 |
| gcaggatgcc | atcctaatgg | catgaagctt | ctgaactata | accctgagga | tcctccagga | 900 |
| tcagaagtac | ttcgtatcca | gaatgttttg | tctgagaagc | ccagggtgag | caccgtgtac | 960 |
| accaataacg | gctctgtgct | tcagggctcc | accgtggctt | ctgtgtacca | agggaagatt | 1020 |
| ctcataggca | ctatatttca | caaactctg | tattgtgtgc | tctagtctcc | agctcttcca | 1080 |
| aaaagtctac | ctgtttggta | aagtaaaatc | tttaaaggtg | tgataattgg | aaccataagt | 1140 |
| aaataacaaa | taccaacaaa | a | | | | 1161 |

<210> SEQ ID NO 16
<211> LENGTH: 354
<212> TYPE: PRT
<213> ORGANISM: Oryctolagus cuniculus

<400> SEQUENCE: 16

Met Ala Lys Leu Leu Leu Thr Leu Leu Gly Ala Ser Leu Ala Phe
1               5                   10                  15

Val Gly Glu Arg Leu Leu Ala Phe Arg Asn Ser Phe Gly Ala Val Gln
            20                  25                  30

Glu Leu Glu Pro Val Glu Pro Gln Asn Cys Val Leu Ile Glu Gly Leu
        35                  40                  45

Glu Asn Gly Ser Glu Asp Ile Asp Ile Leu Pro Ser Gly Leu Ala Phe
    50                  55                  60

Ile Ser Ser Gly Leu Lys Tyr Pro Gly Met Pro Asn Phe Ala Pro Asp
65                  70                  75                  80

Glu Pro Gly Lys Ile Phe Leu Ile Asp Met Asn Glu Lys Asn Pro Arg
                85                  90                  95

Ala Gln Glu Leu Glu Ile Ser Asn Gly Phe Glu Lys Glu Ser Phe Asn 100                 105                 110
Pro His Gly Ile Ser Thr Phe Ile Asp Lys Asp His Thr Val Tyr Leu
        115                 120                 125

Tyr Val Val Asn His Pro His Met Lys Ser Thr Val Glu Ile Phe Lys
    130                 135                 140

Phe Glu Glu Gln Gln Arg Ser Leu Val His Leu Lys Thr Ile Lys His
145                 150                 155                 160

Glu Leu Leu Lys Ser Val Asn Asn Ile Val Val Leu Gly Pro Glu Gln
                165                 170                 175

Phe Tyr Ala Thr Arg Asp His Tyr Phe Thr Asn Tyr Val Leu Ala Leu
            180                 185                 190

Leu Glu Met Phe Leu Asp Leu His Trp Thr Ser Val Leu Phe Tyr Ser
        195                 200                 205

Pro Lys Glu Val Lys Val Ala Lys Gly Phe Ser Ser Ala Asn Gly
    210                 215                 220

Ile Thr Val Ser Leu Asp Lys Lys Tyr Val Tyr Val Ala Asp Ala Thr
225                 230                 235                 240

Ala Lys Asn Val His Val Met Glu Lys His Asp Asn Trp Asp Leu Thr
                245                 250                 255

Glu Leu Lys Val Ile His Leu Asp Thr Leu Val Asp Asn Leu Ser Val
            260                 265                 270

Asp Pro Ala Thr Gly Asp Ile Leu Ala Gly Cys His Pro Asn Gly Met
        275                 280                 285

Lys Leu Leu Asn Tyr Asn Pro Glu Asp Pro Pro Gly Ser Glu Val Leu
    290                 295                 300

Arg Ile Gln Asn Val Leu Ser Glu Lys Pro Arg Val Ser Thr Val Tyr
305                 310                 315                 320

Thr Asn Asn Gly Ser Val Leu Gln Gly Ser Thr Val Ala Ser Val Tyr
                325                 330                 335

Gln Gly Lys Ile Leu Ile Gly Thr Ile Phe His Lys Thr Leu Tyr Cys
            340                 345                 350

Val Leu

<210> SEQ ID NO 17
<211> LENGTH: 1161
<212> TYPE: DNA
<213> ORGANISM: Oryctolagus cuniculus

<400> SEQUENCE: 17
atggcgaagc tcctgctgct gaccctgctg ggggccagcc tcgccttcgt cggggagagg      60
ttgctggcgt ttagaaacag ctttggtgca gttcaagaac tggagccagt agaaccccag     120
aactgtgtcc ttattaaggg actcgaaaat ggctcggaag atattgatat acttcctagt     180
gggctggctt ttatctccag tggattaaaa tatccaggca tgccaaactt tgcaccagat     240
gagccaggaa aaatcttctt gatagatatg aatgagaaga cccaagagc acaagagctg     300 gaaatcagca atggatttga aaagaatca ttcaatccac atgggatcag cactttcatt     360
gataaagacc atactgtgta tctttatgtt gtgaatcatc cccacatgaa gtctactgtg     420
gagatattta aatttgagga acaacaacgc tctcttgtac acctgaaaac tataaaacat     480
gaacttctca gagtgtgaa taacattgtg gttcttggac cggaacagtt ctacgccacc     540
agagaccact attttaccaa ctatgtctta gcacttcttg agatgttttt ggatcttcac     600
tggacttccg ttctttttcta cagcccccaaa gaggtcaaag tggtggccaa aggattcagt     660

-continued

```
tctgccaatg ggatcacagt ctcactagat aagaagtatg tctatgttgc tgatgccaca        720
gctaagaatg tgcatgtaat ggaaaaacat gacaactggg atttaactga actgaaggta        780
atacacttgg acaccttagt ggataatttg tctgttgatc ctgccacggg agatatcttg        840
gcaggatgcc atcctaatgg catgaagctt ctgaactata accctgagga tcctccagga        900
tcagaagtac ttcgtatcca gaatgttttg tctgagaagc ccagggtgag caccgtgtaa        960
accaatgacg gctctgtgct tcagggctcc accgtggctt ctgtgtacca agggaagatt       1020
ctcataggca ctatatttca caaactctg tattgtgtgc tctagtctcc agctcttcca       1080
aaaagtctac ctgtttggta aagtaaatc tttaaaggtg tgataattgg aaccataagt        1140
aaataacaaa taccaacaaa a                                                 1161
```

<210> SEQ ID NO 18
<211> LENGTH: 319
<212> TYPE: PRT
<213> ORGANISM: Oryctolagus cuniculus

<400> SEQUENCE: 18

```
Met Ala Lys Leu Leu Leu Thr Leu Leu Gly Ala Ser Leu Ala Phe
1               5                   10                  15

Val Gly Glu Arg Leu Leu Ala Phe Arg Asn Ser Phe Gly Ala Val Gln
            20                  25                  30

Glu Leu Glu Pro Val Glu Pro Gln Asn Cys Val Leu Ile Lys Gly Leu
        35                  40                  45

Glu Asn Gly Ser Glu Asp Ile Asp Ile Leu Pro Ser Gly Leu Ala Phe
    50                  55                  60

Ile Ser Ser Gly Leu Lys Tyr Pro Gly Met Pro Asn Phe Ala Pro Asp
65                  70                  75                  80

Glu Pro Gly Lys Ile Phe Leu Ile Asp Met Asn Glu Lys Asn Pro Arg
                85                  90                  95

Ala Gln Glu Leu Glu Ile Ser Asn Gly Phe Glu Lys Glu Ser Phe Asn
            100                 105                 110

Pro His Gly Ile Ser Thr Phe Ile Asp Lys Asp His Thr Val Tyr Leu
        115                 120                 125

Tyr Val Val Asn His Pro His Met Lys Ser Thr Val Glu Ile Phe Lys
    130                 135                 140

Phe Glu Glu Gln Gln Arg Ser Leu Val His Leu Lys Thr Ile Lys His
145                 150                 155                 160

Glu Leu Leu Lys Ser Val Asn Asn Ile Val Val Leu Gly Pro Glu Gln
                165                 170                 175

Phe Tyr Ala Thr Arg Asp His Tyr Phe Thr Asn Tyr Val Leu Ala Leu
            180                 185                 190

Leu Glu Met Phe Leu Asp Leu His Trp Thr Ser Val Leu Phe Tyr Ser
        195                 200                 205

Pro Lys Glu Val Lys Val Ala Lys Gly Phe Ser Ser Ala Asn Gly
    210                 215                 220

Ile Thr Val Ser Leu Asp Lys Lys Tyr Val Tyr Val Ala Asp Ala Thr
225                 230                 235                 240

Ala Lys Asn Val His Val Met Glu Lys His Asp Asn Trp Asp Leu Thr
                245                 250                 255

Glu Leu Lys Val Ile His Leu Asp Thr Leu Val Asp Asn Leu Ser Val
            260                 265                 270

Asp Pro Ala Thr Gly Asp Ile Leu Ala Gly Cys His Pro Asn Gly Met
        275                 280                 285
```

```
Lys Leu Leu Asn Tyr Asn Pro Glu Asp Pro Pro Gly Ser Glu Val Leu
    290                 295                 300

Arg Ile Gln Asn Val Leu Ser Glu Lys Pro Arg Val Ser Thr Val
305                 310                 315
```

<210> SEQ ID NO 19
<211> LENGTH: 26
<212> TYPE: PRT
<213> ORGANISM: Artificial Sequence
<220> FEATURE:
<223> OTHER INFORMATION: Synthetic

<400> SEQUENCE: 19

```
Ala Lys Leu Leu Leu Thr Leu Leu Gly Ala Ser Leu Ala Phe Val
1               5                   10                  15

Gly Glu Arg Leu Leu Ala Phe Arg Arg Asn
            20                  25
```

<210> SEQ ID NO 20
<211> LENGTH: 15
<212> TYPE: PRT
<213> ORGANISM: Artificial Sequence
<220> FEATURE:
<223> OTHER INFORMATION: Synthetic

<400> SEQUENCE: 20

```
Leu Asp Trp Gln Asp Val Asn Pro Val Ala His Ile Lys Ser Ser
1               5                   10                  15
```

<210> SEQ ID NO 21
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: SITE
<222> LOCATION: (1)..(1)
<223> OTHER INFORMATION: Xaa at this position can be any amino acid.

<400> SEQUENCE: 21

```
Xaa Asp Thr Phe Ile Ala Ala Val Tyr Glu His Ala Val Ile Leu Pro
1               5                   10                  15
```

<210> SEQ ID NO 22
<211> LENGTH: 354
<212> TYPE: PRT
<213> ORGANISM: Oryctolagus cuniculus

<400> SEQUENCE: 22

```
Met Ala Lys Leu Leu Leu Thr Leu Leu Gly Ala Ser Leu Ala Phe
1               5                   10                  15

Val Gly Glu Arg Leu Leu Ala Phe Arg Asn Ser Phe Gly Ala Val Gln
            20                  25                  30

Glu Leu Glu Pro Val Glu Pro Gln Asn Cys Val Leu Ile Glu Gly Leu
        35                  40                  45

Glu Asn Gly Ser Glu Asp Ile Asp Ile Leu Pro Ser Gly Leu Ala Phe
    50                  55                  60

Ile Ser Ser Gly Leu Lys Tyr Pro Gly Met Pro Asn Phe Ala Pro Asp
65                  70                  75                  80

Glu Pro Gly Lys Ile Phe Leu Ile Asp Met Asn Glu Lys Asn Pro Arg
                85                  90                  95
```

```
Ala Gln Glu Leu Glu Ile Ser Asn Gly Phe Glu Lys Glu Ser Phe Asn
            100                 105                 110

Pro His Gly Ile Ser Thr Phe Ile Asp Lys Asp His Thr Val Tyr Leu
            115                 120                 125

Tyr Val Val Asn His Pro His Met Lys Ser Thr Val Glu Ile Phe Lys
130                 135                 140

Phe Glu Glu Gln Gln Arg Ser Leu Val His Leu Lys Thr Ile Lys His
145                 150                 155                 160

Glu Leu Leu Lys Ser Val Asn Asn Ile Val Val Leu Gly Pro Glu Gln
                165                 170                 175

Phe Tyr Ala Thr Arg Asp His Tyr Phe Thr Asn Tyr Val Leu Ala Leu
            180                 185                 190

Leu Glu Met Phe Leu Asp Leu His Trp Thr Ser Val Leu Phe Tyr Ser
            195                 200                 205

Pro Lys Glu Val Lys Val Ala Lys Gly Phe Ser Ser Ala Asn Gly
            210                 215                 220

Ile Thr Val Ser Leu Asp Lys Lys Tyr Val Tyr Val Ala Asp Ala Thr
225                 230                 235                 240

Ala Lys Asn Val His Val Met Glu Lys His Asp Asn Trp Asp Leu Thr
                245                 250                 255

Glu Leu Lys Val Ile His Leu Asp Thr Leu Val Asp Asn Leu Ser Val
                260                 265                 270

Asp Pro Ala Thr Gly Asp Ile Leu Ala Gly Cys His Pro Asn Gly Met
            275                 280                 285

Lys Leu Leu Asn Tyr Asn Pro Glu Asp Pro Pro Gly Ser Glu Val Leu
            290                 295                 300

Arg Ile Gln Asn Val Leu Ser Glu Lys Pro Arg Val Ser Thr Val Tyr
305                 310                 315                 320

Thr Asn Asp Gly Ser Val Leu Gln Gly Ser Thr Val Ala Ser Val Tyr
                325                 330                 335

Gln Gly Lys Ile Leu Ile Gly Thr Ile Phe His Lys Thr Leu Tyr Cys
            340                 345                 350

Val Leu

<210> SEQ ID NO 23
<211> LENGTH: 350
<212> TYPE: PRT
<213> ORGANISM: Oryctolagus cuniculus

<400> SEQUENCE: 23

Leu Leu Leu Thr Leu Gly Ala Ser Leu Ala Phe Val Gly Glu Val
1               5                   10                  15

Leu Leu Ala Phe Arg Asn Ser Phe Glu Ala Val Gln Glu Val Glu Pro
                20                  25                  30

Thr Glu Pro Gln Asn Cys His Leu Ile Glu Gly Leu Glu Asn Gly Ser
            35                  40                  45

Glu Asp Ile Asp Ile Leu Pro Ser Gly Leu Ala Phe Ile Ser Ser Gly
50                  55                  60

Leu Lys Tyr Pro Gly Met Pro Asn Phe Ala Pro Asp Glu Pro Gly Lys
65                  70                  75                  80

Ile Phe Leu Ile Asp Met Asn Glu Lys Asn Pro Arg Ala Gln Glu Leu
                85                  90                  95

Glu Ile Ser Ser Gly Phe Glu Lys Glu Ser Phe Asn Pro His Gly Ile
            100                 105                 110
```

```
Ser Thr Phe Ile Asp Lys Asp Pro Thr Val Tyr Leu Tyr Val Val Asn
        115                 120                 125

Gln Pro His Met Lys Ser Thr Val Glu Ile Phe Lys Phe Glu Glu Gln
    130                 135                 140

Gln Arg Ser Leu Val His Leu Lys Thr Ile Lys His Glu Leu Leu Lys
145                 150                 155                 160

Ser Val Asn Asn Ile Val Val Leu Gly Pro Glu Gln Phe Tyr Ala Thr
                165                 170                 175

Arg Asp His Tyr Phe Thr Asn Tyr Val Leu Ala Leu Leu Glu Met Phe
            180                 185                 190

Leu Asp Leu His Trp Thr Ser Val Leu Phe Tyr Ser Pro Lys Glu Val
            195                 200                 205

Lys Val Val Ala Lys Gly Phe Ser Ser Ala Asn Gly Ile Thr Val Ser
210                 215                 220

Gly Asp Gln Lys Tyr Val Tyr Val Ala Asp Ala Thr Ala Lys Asn Val
225                 230                 235                 240

His Val Met Glu Lys His Asp Asn Trp Asp Leu Thr Gln Leu Lys Val
                245                 250                 255

Ile His Leu Val Thr Leu Val Asp Asn Leu Ser Val Asp Pro Ala Thr
                260                 265                 270

Gly Asp Ile Leu Ala Gly Cys His Pro Asn Pro Met Lys Leu Leu Asn
            275                 280                 285

Tyr Asn Pro Glu Val Pro Pro Gly Ser Glu Val Leu Arg Ile Gln Asn
            290                 295                 300

Val Leu Ser Glu Lys Pro Arg Val Ser Thr Val Tyr Thr Asn Asp Gly
305                 310                 315                 320

Ser Val Leu Gln Gly Ser Thr Val Ala Ser Val Tyr Gln Gly Lys Ile
                325                 330                 335

Leu Ile Gly Thr Ile Phe His Lys Thr Leu Tyr Cys Asp Leu
                340                 345                 350

<210> SEQ ID NO 24
<211> LENGTH: 354
<212> TYPE: PRT
<213> ORGANISM: Homo sapiens

<400> SEQUENCE: 24

Met Gly Lys Leu Val Ala Leu Val Leu Leu Gly Val Gly Leu Ser Leu
1               5                   10                  15

Val Glu Glu Met Phe Leu Ala Phe Arg Glu Arg Val Asn Ala Ser Gln
            20                  25                  30

Glu Val Glu Pro Val Glu Pro Glu Asn Cys His Leu Ile Glu Glu Leu
            35                  40                  45

Glu Ser Gly Ser Glu Asp Ile Asp Ile Leu Pro Ser Gly Leu Ser Phe
    50                  55                  60

Ile Ser Ser Glu Leu Lys Tyr Pro Gly Met Pro Asn Phe Ala Pro Asp
65                  70                  75                  80

Glu Pro Gly Lys Ile Phe Leu Met Asp Leu Asn Glu Gln Asn Pro Arg
                85                  90                  95

Ala Gln Ala Leu Glu Ile Ser Gly Gly Phe Asp Lys Glu Leu Phe Asn
            100                 105                 110

Pro His Gly Ile Ser Ile Phe Ile Asp Lys Asp Asn Thr Val Tyr Leu
        115                 120                 125

Tyr Val Val Asn His Pro His Met Lys Ser Thr Val Glu Ile Phe Lys
    130                 135                 140
```

```
Phe Glu Glu Gln Gln Arg Ser Leu Val Tyr Leu Lys Thr Ile Lys His
145                 150                 155                 160

Glu Leu Lys Ser Val Asn Asp Ile Val Leu Gly Pro Glu Gln
            165                 170                 175

Phe Tyr Ala Thr Arg Asp His Tyr Phe Thr Asn Ser Leu Leu Ser Phe
            180                 185                 190

Phe Glu Met Ile Leu Asp Leu Arg Trp Thr Tyr Val Leu Phe Tyr Ser
            195                 200                 205

Pro Arg Glu Val Lys Val Val Ala Lys Gly Phe Cys Ser Ala Asn Gly
210                 215                 220

Ile Thr Val Ser Ala Asp Gln Lys Tyr Val Tyr Val Ala Asp Val Ala
225                 230                 235                 240

Ala Lys Asn Ile His Ile Met Glu Lys His Asp Asn Trp Asp Leu Thr
                245                 250                 255

Gln Leu Lys Val Ile Gln Leu Gly Thr Leu Val Asp Asn Leu Thr Val
            260                 265                 270

Asp Pro Ala Thr Gly Asp Ile Leu Ala Gly Cys His Pro Asn Pro Met
            275                 280                 285

Lys Leu Leu Asn Tyr Asn Pro Glu Asp Pro Gly Ser Glu Val Leu
290                 295                 300

Arg Ile Gln Asn Val Leu Ser Glu Lys Pro Arg Val Ser Thr Val Tyr
305                 310                 315                 320

Ala Asn Asn Gly Ser Val Leu Gln Gly Thr Ser Val Ala Ser Val Tyr
            325                 330                 335

His Gly Lys Ile Leu Ile Gly Thr Val Phe His Lys Thr Leu Tyr Cys
            340                 345                 350

Glu Leu

<210> SEQ ID NO 25
<211> LENGTH: 354
<212> TYPE: PRT
<213> ORGANISM: Mus musculus

<400> SEQUENCE: 25

Met Gly His Leu Val Ala Leu Pro Leu Leu Gly Ala Cys Leu Ala Leu
1               5                   10                  15

Ile Gly Glu Arg Leu Leu Asn Phe Arg Glu Arg Val Ser Thr Thr Arg
                20                  25                  30

Glu Ile Lys Ala Thr Glu Pro Gln Asn Cys His Leu Ile Glu Gly Leu
            35                  40                  45

Glu Asn Gly Ser Glu Asp Ile Asp Ile Leu Pro Ser Gly Leu Ala Phe
        50                  55                  60

Ile Ser Thr Gly Leu Lys Tyr Pro Gly Met Pro Ala Phe Ala Pro Asp
65                  70                  75                  80

Lys Pro Gly Arg Ile Phe Leu Met Asp Leu Asn Glu Gln Asn Pro Glu
                85                  90                  95

Ala Gln Ala Leu Glu Ile Ser Gly Gly Leu Asp Gln Glu Ser Leu Asn
            100                 105                 110

Pro His Gly Ile Ser Thr Phe Ile Asp Lys Asp Asn Thr Ala Tyr Leu
        115                 120                 125

Tyr Val Val Asn His Pro Asn Met Asp Ser Thr Val Glu Ile Phe Lys
130                 135                 140

Phe Glu Glu Gln Gln Arg Ser Leu Ile His Leu Lys Thr Leu Lys His
145                 150                 155                 160
```

```
Glu Leu Leu Lys Ser Val Asn Asp Ile Val Leu Gly Pro Glu Gln
                165                 170                 175

Phe Tyr Ala Thr Arg Asp His Tyr Phe Thr Ser Tyr Phe Leu Val Leu
            180                 185                 190

Leu Glu Met Ile Leu Asp Pro His Trp Thr Ser Val Val Phe Tyr Ser
        195                 200                 205

Pro Lys Glu Val Lys Val Ala Gln Gly Phe Ser Ser Ala Asn Gly
    210                 215                 220

Ile Thr Val Ser Leu Asp Gln Lys Phe Val Tyr Val Ala Asp Val Thr
225                 230                 235                 240

Ala Lys Asn Ile His Ile Met Glu Lys His Asp Asn Trp Asp Leu Thr
                245                 250                 255

Pro Val Lys Val Ile Gln Leu Gly Thr Leu Val Asp Asn Leu Thr Val
                260                 265                 270

Ala Pro Ala Thr Gly Asp Ile Leu Ala Gly Cys His Pro Asn Pro Met
            275                 280                 285

Lys Leu Leu Ile Tyr Asn Pro Glu Gly Pro Pro Gly Ser Glu Val Leu
        290                 295                 300

Arg Ile Gln Asp Ser Leu Ser Asp Lys Pro Arg Val Ser Thr Leu Tyr
305                 310                 315                 320

Ala Asn Asn Gly Ser Val Leu Gln Gly Ser Thr Val Ala Ser Val Tyr
                325                 330                 335

His Lys Arg Met Leu Ile Gly Thr Ile Phe His Lys Ala Leu Tyr Cys
                340                 345                 350

Asp Leu

<210> SEQ ID NO 26
<211> LENGTH: 359
<212> TYPE: PRT
<213> ORGANISM: Oryctolagus cuniculus

<400> SEQUENCE: 26

Met Ala Lys Leu Thr Ala Leu Thr Leu Leu Gly Leu Gly Leu Ala Leu
1               5                   10                  15

Phe Asp Gly Gln Lys Ser Ser Phe Gln Thr Arg Phe Asn Val His Arg
            20                  25                  30

Glu Val Thr Pro Val Glu Leu Pro Asn Cys Asn Leu Val Lys Gly Ile
        35                  40                  45

Asp Asn Gly Ser Glu Asp Leu Glu Ile Leu Pro Asn Gly Leu Ala Phe
    50                  55                  60

Ile Ser Ala Gly Leu Lys Tyr Pro Gly Ile Met Ser Phe Asp Pro Asp
65                  70                  75                  80

Lys Pro Gly Lys Ile Leu Leu Met Asp Leu Asn Glu Lys Asp Pro Val
                85                  90                  95

Val Leu Glu Leu Ser Ile Thr Gly Ser Thr Phe Asp Leu Ser Ser Phe
            100                 105                 110

Asn Pro His Gly Ile Ser Thr Phe Thr Asp Glu Asp Asn Ile Val Tyr
        115                 120                 125

Leu Met Val Val Asn His Pro Asp Ser Lys Ser Thr Val Glu Leu Phe
    130                 135                 140

Lys Phe Gln Glu Lys Glu Lys Ser Leu Leu His Leu Lys Thr Ile Arg
145                 150                 155                 160

His Lys Leu Leu Pro Ser Val Asn Asp Ile Val Ala Val Gly Pro Glu
                165                 170                 175
```

His Phe Tyr Ala Thr Asn Asp His Thr Phe Ile Asp Pro Tyr Leu Lys
                180                 185                 190

Ser Trp Glu Met His Leu Gly Leu Ala Trp Ser Phe Val Thr Tyr Tyr
        195                 200                 205

Ser Pro Asn Asp Val Arg Val Val Ala Glu Gly Phe Asp Phe Ala Asn
        210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asn Thr Leu Val Asp Asn Ile Ser
            260                 265                 270

Val Asp Pro Val Thr Gly Asp Leu Trp Val Gly Cys His Pro Asn Gly
        275                 280                 285

Met Arg Ile Phe Tyr Tyr Asp Pro Lys Asn Pro Pro Ala Ser Glu Val
        290                 295                 300

Leu Arg Ile Gln Asp Ile Leu Ser Lys Glu Pro Lys Val Thr Val Ala
305                 310                 315                 320

Tyr Ala Glu Asn Gly Thr Val Leu Gln Gly Ser Thr Val Ala Ala Val
                325                 330                 335

Tyr Lys Gly Lys Met Leu Val Gly Thr Val Phe His Lys Ala Leu Tyr
            340                 345                 350

Cys Glu Leu Ser Gln Ala Asn
        355

<210> SEQ ID NO 27
<211> LENGTH: 37
<212> TYPE: PRT
<213> ORGANISM: Artificial Sequence
<220> FEATURE:
<223> OTHER INFORMATION: Synthetic

<400> SEQUENCE: 27

Gly Ser Glu Asp Ile Asp Ile Leu Pro Ser Gly Leu Ala Phe Ile Ser
1               5                   10                  15

Ser Gly Leu Lys Tyr Pro Gly Met Pro Asn Phe Ala Pro Asp Glu Pro
            20                  25                  30

Gly Lys Ile Phe Leu
        35

<210> SEQ ID NO 28
<211> LENGTH: 63
<212> TYPE: PRT
<213> ORGANISM: Artificial Sequence
<220> FEATURE:
<223> OTHER INFORMATION: Synthetic
<220> FEATURE:
<221> NAME/KEY: SITE
<222> LOCATION: (1)..(1)
<223> OTHER INFORMATION: Xaa at this position can be His or Pro.
<220> FEATURE:
<221> NAME/KEY: SITE
<222> LOCATION: (10)..(10)
<223> OTHER INFORMATION: Xaa at this position can be His or Gln.

<400> SEQUENCE: 28

Xaa Thr Val Tyr Leu Tyr Val Val Asn Xaa Pro His Met Lys Ser Thr
1               5                   10                  15

Val Glu Ile Phe Lys Phe Glu Glu Gln Gln Arg Ser Leu Val His Leu
            20                  25                  30

-continued

```
Lys Thr Ile Lys His Glu Leu Leu Lys Ser Val Asn Asn Ile Val Val
            35                  40                  45

Leu Gly Pro Glu Gln Phe Tyr Ala Thr Arg Asp His Tyr Phe Thr
    50                  55                  60
```

<210> SEQ ID NO 29
<211> LENGTH: 25
<212> TYPE: PRT
<213> ORGANISM: Artificial Sequence
<220> FEATURE:
<223> OTHER INFORMATION: Synthetic

<400> SEQUENCE: 29

```
Ser Val Leu Phe Tyr Ser Pro Lys Glu Val Lys Val Val Ala Lys Gly
1               5                   10                  15

Phe Ser Ser Ala Asn Gly Ile Thr Val
            20                  25
```

<210> SEQ ID NO 30
<211> LENGTH: 45
<212> TYPE: PRT
<213> ORGANISM: Artificial Sequence
<220> FEATURE:
<223> OTHER INFORMATION: Synthetic
<220> FEATURE:
<221> NAME/KEY: SITE
<222> LOCATION: (16)..(16)
<223> OTHER INFORMATION: Xaa at this position can be Asn or Pro.
<220> FEATURE:
<221> NAME/KEY: SITE
<222> LOCATION: (27)..(27)
<223> OTHER INFORMATION: Xaa at this position can be Asp or Val.

<400> SEQUENCE: 30

```
Ser Val Asp Pro Ala Thr Gly Asp Ile Leu Ala Gly Cys His Pro Xaa
1               5                   10                  15

Gly Met Lys Leu Leu Asn Tyr Asn Pro Glu Xaa Pro Pro Gly Ser Glu
            20                  25                  30

Val Leu Arg Ile Gln Asn Val Leu Ser Glu Lys Pro Arg
        35                  40                  45
```

<210> SEQ ID NO 31
<211> LENGTH: 355
<212> TYPE: PRT
<213> ORGANISM: Homo sapiens

<400> SEQUENCE: 31

```
Met Ala Lys Leu Ile Ala Leu Thr Leu Leu Gly Met Gly Leu Ala Leu
1               5                   10                  15

Phe Arg Asn His Gln Ser Ser Tyr Gln Thr Arg Leu Asn Ala Leu Arg
            20                  25                  30

Glu Val Gln Pro Val Glu Leu Pro Asn Cys Asn Leu Val Lys Gly Ile
        35                  40                  45

Glu Thr Gly Ser Glu Asp Met Glu Ile Leu Pro Asn Gly Leu Ala Phe
    50                  55                  60

Ile Ser Ser Gly Leu Lys Tyr Pro Gly Ile Lys Ser Phe Asn Pro Asn
65              70                  75                  80

Ser Pro Gly Lys Ile Leu Leu Met Asp Leu Asn Glu Glu Asp Pro Thr
            85                  90                  95

Val Leu Glu Leu Gly Ile Thr Gly Ser Lys Phe Asp Val Ser Ser Phe
            100                 105                 110
```

```
Asn Pro His Gly Ile Ser Thr Phe Thr Asp Glu Asp Asn Ala Met Tyr
        115                 120                 125

Leu Leu Val Val Asn His Pro Asp Ala Lys Ser Thr Val Glu Leu Phe
        130                 135                 140

Lys Phe Gln Glu Glu Lys Ser Leu Leu His Leu Lys Thr Ile Arg
145                 150                 155                 160

His Lys Leu Leu Pro Asn Leu Asn Asp Ile Val Ala Val Gly Pro Glu
                165                 170                 175

His Phe Tyr Gly Thr Asn Asp His Thr Phe Leu Asp Pro Tyr Leu Gln
            180                 185                 190

Ser Trp Glu Met Tyr Leu Gly Leu Ala Trp Ser Tyr Val Val Tyr Tyr
        195                 200                 205

Ser Pro Ser Glu Val Arg Val Val Ala Glu Gly Phe Asp Phe Ala Asn
210                 215                 220

Gly Ile Asn Ile Ser Pro Asp Gly Lys Tyr Val Tyr Ile Ala Glu Leu
225                 230                 235                 240

Leu Ala His Lys Ile His Val Tyr Glu Lys His Ala Asn Trp Thr Leu
                245                 250                 255

Thr Pro Leu Lys Ser Leu Asp Phe Asn Thr Leu Val Asp Asn Ile Ser
            260                 265                 270

Val Asp Pro Glu Thr Gly Asp Leu Trp Val Gly Cys His Pro Asn Gly
        275                 280                 285

Met Lys Ile Phe Phe Tyr Asp Ser Glu Asn Pro Pro Ala Ser Glu Val
290                 295                 300

Leu Arg Ile Gln Asn Ile Leu Thr Glu Glu Pro Lys Val Thr Gln Val
305                 310                 315                 320

Tyr Ala Glu Asn Gly Thr Val Leu Gln Gly Ser Thr Val Ala Ser Val
                325                 330                 335

Tyr Lys Gly Lys Leu Leu Ile Gly Thr Val Phe His Lys Ala Leu Tyr
            340                 345                 350

Cys Glu Leu
        355

<210> SEQ ID NO 32
<211> LENGTH: 354
<212> TYPE: PRT
<213> ORGANISM: Oryctolagus cuniculus
<220> FEATURE:
<221> NAME/KEY: SITE
<222> LOCATION: (242)..(242)
<223> OTHER INFORMATION: Xaa at this position can be any amino acid.

<400> SEQUENCE: 32

Met Gly Arg Leu Val Ala Val Ser Val Leu Gly Ile Ala Leu Ala Leu
1               5                   10                  15

Leu Gly Glu Arg Leu Leu Ala Leu Arg Asn Arg Leu Lys Ala Ser Arg
            20                  25                  30

Glu Ile Glu Ser Val Asp Leu Pro Asn Cys His Leu Ile Lys Gly Ile
        35                  40                  45

Glu Ala Gly Ser Glu Asp Ile Asp Ile Leu Pro Asn Gly Leu Ala Phe
    50                  55                  60

Phe Ser Val Gly Leu Lys Cys Pro Gly Leu His Ser Phe Ala Pro Asp
65                  70                  75                  80

Lys Pro Gly Gly Ile Leu Met Met Asp Leu Lys Glu Glu Arg Pro Arg
                85                  90                  95

Ala Leu Glu Leu Arg Ile Ser Arg Gly Phe Asp Leu Ala Ser Phe Asn
```

-continued

```
                     100                 105                 110
Pro His Gly Ile Ser Thr Phe Ile Asp Asp Asp Thr Ile Tyr Leu
            115                 120                 125

Phe Val Val Asn His Pro Glu Phe Lys Asn Thr Val Glu Ile Phe Lys
130                 135                 140

Phe Glu Glu Glu Asn Ser Leu Leu His Leu Lys Thr Ile Arg His
145                 150                 155                 160

Glu Leu Leu Pro Ser Val Asn Asp Val Ile Ala Val Gly Pro Ala His
                165                 170                 175

Phe Tyr Ala Thr Asn Asp His Tyr Phe Ser Asp Pro Phe Leu Lys Tyr
            180                 185                 190

Leu Glu Thr Tyr Leu Asn Leu His Trp Ala Asn Val Ile Tyr Tyr Ser
                195                 200                 205

Pro Asn Glu Val Lys Val Val Ala Asp Gly Phe Asp Ser Ala Asn Gly
            210                 215                 220

Ile Asn Ile Ser Pro Asp Lys Lys Tyr Ile Tyr Val Ala Asp Ile Leu
225                 230                 235                 240

Ala Xaa Glu Ile His Val Leu Asp Lys His Ser Asn Met Asn Leu Thr
                245                 250                 255

Gln Leu Lys Val Leu Gln Leu Asp Thr Leu Val Asp Asn Leu Ser Val
            260                 265                 270

Asp Pro Ser Ser Gly Asp Ile Trp Ala Gly Cys His Pro Asn Gly Gln
        275                 280                 285

Lys Val Tyr Val Tyr Asp Pro Asn Asn Pro Ser Ser Glu Val Leu
            290                 295                 300

Arg Ile Gln Asn Ile Leu Ser Glu Lys Pro Thr Val Thr Thr Val Tyr
305                 310                 315                 320

Ala Asn Asn Gly Ser Val Leu Gln Gly Ser Ser Val Ala Ser Val Tyr
                325                 330                 335

Asp Gly Lys Leu Leu Ile Gly Thr Leu Tyr His Arg Ala Leu Tyr Cys
            340                 345                 350

Glu Leu

<210> SEQ ID NO 33
<211> LENGTH: 354
<212> TYPE: PRT
<213> ORGANISM: Homo sapiens

<400> SEQUENCE: 33

Met Gly Ala Trp Val Gly Cys Gly Leu Ala Gly Asp Arg Ala Gly Phe
1               5                   10                  15

Leu Gly Glu Arg Leu Leu Ala Leu Arg Asn Arg Leu Lys Ala Ser Arg
            20                  25                  30

Glu Val Glu Ser Val Asp Leu Pro His Cys His Leu Ile Lys Gly Ile
        35                  40                  45

Glu Ala Gly Ser Glu Asp Ile Asp Ile Leu Pro Asn Gly Leu Ala Phe
    50                  55                  60

Phe Ser Val Gly Leu Lys Phe Pro Gly Leu His Ser Phe Ala Pro Asp
65                  70                  75                  80

Lys Pro Gly Gly Ile Leu Met Met Asp Leu Lys Glu Glu Lys Pro Arg
                85                  90                  95

Ala Arg Glu Leu Arg Ile Ser Arg Gly Phe Asp Leu Ala Ser Phe Asn
            100                 105                 110

Pro His Gly Ile Ser Thr Phe Ile Asp Asn Asp Asp Thr Val Tyr Leu
```

```
            115                 120                 125
Phe Val Val Asn His Pro Glu Phe Lys Asn Thr Val Glu Ile Phe Lys
    130                 135                 140

Phe Glu Glu Ala Glu Asn Ser Leu Leu His Leu Lys Thr Val Lys His
145                 150                 155                 160

Glu Leu Leu Pro Ser Val Asn Asp Ile Thr Ala Val Gly Pro Ala His
                165                 170                 175

Phe Tyr Ala Thr Asn Asp His Tyr Phe Ser Asp Pro Phe Leu Lys Tyr
            180                 185                 190

Leu Gly Thr Tyr Leu Asn Leu His Trp Ala Asn Val Val Tyr Tyr Ser
        195                 200                 205

Pro Asn Glu Val Lys Val Val Ala Glu Gly Phe Asp Ser Ala Asn Gly
    210                 215                 220

Ile Asn Ile Ser Pro Asp Asp Lys Tyr Ile Tyr Val Ala Asp Ile Leu
225                 230                 235                 240

Ala His Glu Ile His Val Leu Glu Lys His Thr Asn Met Asn Leu Thr
                245                 250                 255

Gln Leu Lys Val Leu Glu Leu Asp Thr Leu Val Asp Asn Leu Ser Ile
            260                 265                 270

Asp Pro Ser Ser Gly Asp Ile Trp Val Gly Cys His Pro Asn Gly Gln
        275                 280                 285

Lys Leu Phe Val Tyr Asp Pro Asn Asn Pro Ser Ser Glu Val Leu
    290                 295                 300

Arg Ile Gln Asn Ile Leu Cys Glu Lys Pro Thr Val Thr Thr Val Tyr
305                 310                 315                 320

Ala Asn Asn Gly Ser Val Leu Gln Gly Ser Ser Val Ala Ser Val Tyr
                325                 330                 335

Asp Gly Lys Leu Leu Ile Gly Thr Leu Tyr His Arg Ala Leu Tyr Cys
            340                 345                 350

Glu Leu

<210> SEQ ID NO 34
<211> LENGTH: 356
<212> TYPE: PRT
<213> ORGANISM: Homo sapiens

<400> SEQUENCE: 34

Met Gly Arg Leu Val Ala Val Gly Leu Leu Gly Ile Ala Leu Ala Leu
1               5                   10                  15

Leu Gly Glu Arg Leu Leu Ala Leu Arg Asn Arg Leu Lys Ala Ser Arg
            20                  25                  30

Glu Val Glu Ser Val Asp Leu Pro His Cys His Leu Ile Lys Gly Ile
        35                  40                  45

Glu Ala Gly Ser Glu Asp Ile Asp Ile Leu Pro Asn Gly Leu Ala Phe
    50                  55                  60

Leu Ser Val Gly Leu Lys Phe Pro Gly Leu His Ser Phe Ala Pro Asp
65                  70                  75                  80

Lys Pro Gly Gly Ile Leu Met Met Val Leu Lys Glu Ala Lys Pro Arg
                85                  90                  95

Gly Arg Glu Leu Arg Ile Ser Arg Gly Phe Asp Leu Ala Ser Phe Asn
            100                 105                 110

Pro His Gly Ile Ser Thr Phe Ile Asp Asn Asp Asp Thr Val Tyr Leu
        115                 120                 125

Leu Val Val Asn His Pro Glu Phe Lys Asn Thr Val Glu Ile Phe Asn
```

-continued

```
            130                 135                 140
Leu Glu Glu Ala Glu Asn Ser Leu Leu His Leu Lys Thr Val Lys His
145                 150                 155                 160

Glu Leu Leu Pro Ser Val Asn Asp Ile Thr Ala Val Gly Pro Ala His
                165                 170                 175

Phe Tyr Ala Thr Asn Asp His Tyr Phe Ser Asp Pro Phe Leu Lys Tyr
                180                 185                 190

Leu Glu Thr Tyr Leu Glu Leu His Trp Ala Asn Val Val Tyr Tyr Arg
                195                 200                 205

Pro Asn Glu Val Lys Gly Gly Ser Arg Lys Asp Leu Asp Ser Ala Asn
                210                 215                 220

Gly Ile Asn Ile Ser Pro Gly Trp Ile Ser Phe Ser Met Leu Ala Asp
225                 230                 235                 240

Ile Leu Ala His Glu Ile His Val Trp Gly Lys His Thr Asn Met Asn
                245                 250                 255

Leu Thr Gln Leu Lys Val Leu Glu Leu Asp Thr Leu Val Asp Asn Leu
                260                 265                 270

Ser Ile Asp Pro Ser Ser Gly Asp Ile Trp Val Gly Cys His Pro Asn
                275                 280                 285

Gly Gln Lys Leu Phe Val Tyr Asp Pro Asn Asn Pro Pro Ser Ser Glu
                290                 295                 300

Val Leu Arg Ile Gln Asn Ile Leu Ser Glu Lys Pro Thr Val Thr Thr
305                 310                 315                 320

Val Tyr Ala Asn Asn Gly Ser Val Leu Gln Gly Ser Ser Val Gly Ser
                325                 330                 335

Val Tyr Asp Gly Lys Leu Leu Ile Gly Thr Leu Tyr His Arg Ala Leu
                340                 345                 350

Tyr Cys Glu Leu
                355
```